US008541200B2

(12) United States Patent
Lorentsen et al.

(10) Patent No.: US 8,541,200 B2
(45) Date of Patent: Sep. 24, 2013

(54) CLEAVAGE OF FUSION PROTEINS USING GRANZYME B PROTEASE

(75) Inventors: Rikke Hoegh Lorentsen, Frederiksberg (DK); Charlotte Harkjaer Fynbo, Herlev (DK)

(73) Assignee: Hoffmann-La Roche Inc., Nutley, NJ (US)

( * ) Notice: Subject to any disclaimer, the term of this patent is extended or adjusted under 35 U.S.C. 154(b) by 1198 days.

(21) Appl. No.: 10/553,869

(22) PCT Filed: Apr. 23, 2004

(86) PCT No.: PCT/DK2004/000282
§ 371 (c)(1),
(2), (4) Date: Oct. 21, 2005

(87) PCT Pub. No.: WO2004/094478
PCT Pub. Date: Nov. 4, 2004

(65) Prior Publication Data
US 2006/0199251 A1    Sep. 7, 2006

Related U.S. Application Data

(60) Provisional application No. 60/464,663, filed on Apr. 23, 2003.

(30) Foreign Application Priority Data

Apr. 23, 2003  (DK) .................. 2003 00616

(51) Int. Cl.
*C12P 21/06* (2006.01)
(52) U.S. Cl.
USPC ....................................... 435/68.1
(58) Field of Classification Search
None
See application file for complete search history.

(56) References Cited

U.S. PATENT DOCUMENTS

| 4,543,329 A | 9/1985 | Daum et al. |
| 5,427,927 A | 6/1995 | Meyer et al. |
| 6,010,883 A | 1/2000 | Nagai et al. |
| 6,077,694 A * | 6/2000 | Medabalimi .................. 435/69.7 |

FOREIGN PATENT DOCUMENTS

| WO | WO 94/18227 | 8/1994 |
| WO | WO 98/56906 | 12/1998 |
| WO | WO 03/010204 | 2/2003 |

OTHER PUBLICATIONS

Harris et al, Definition and redesign of the extended substrate specificity of granzyme B. J Biol Chem. Oct. 16, 1998;273(42):27364-73.*
NiceZyme View of Enzyme: EC 3.4.21.79, printout Dec. 19, 2007.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Johnsen et al, Kinetic and structural characterization of a two-domain streptokinase: dissection of domain functionality. Biochemistry. May 30, 2000;39(21):6440-8.*
Pharmacia, Inc. Coupling Gels. In: Affinity Chromatography, Principles & Methods. 1986 p. 9.*
Parenti et al, A novel N-terminal motif for palmitoylation of G-protein alpha subunits. Biochem J. Apr. 15, 1993;291 ( Pt 2):349-53.*
Martin et al, The choline binding site of phospholipase C (*Bacillus cereus*): insights into substrate specificity. Biochemistry. Mar. 28, 2000;39(12):3410-5.*
Boyer et al, Rapid high level production and purification of recombinant murine and human interferons alpha from *Escherichia coli*.J Biol Regul Homeost Agents. Jul.-Sep. 1992;6(3):99-102.*
Braun et al, Oligonucleotide and plasmid DNA packaging into polyoma VP1 virus-like particles expressed in *Escherichia coli*. Biotechnol Appl Biochem. Feb. 1999;29 ( Pt 1):31-43.*
Ni-NTA Agarose product information sheet from Qiagen. Printed Dec. 19, 2007.*
Azad et al, Large-scale production and characterization of recombinant human immunodeficiency virus type 1 Nef. J Gen Virol. Mar. 1994;75 ( Pt 3):651-5.*
Boutin et al, Myristoylation. Cell Signal. Jan. 1997;9(1):15-35. Review.*
Sigma, Inc. Thrombin CleanCleav Kit Recom-T Product Information 1998.*
Deichaite et al, In vitro synthesis of pp60v-src: myristylation in a cell-free system. Mol Cell Biol. Oct. 1988;8(10):4295-301.*
Wan et al, Autoprocessing: an essential step for the activation of HIV-1 protease. Biochem J. Jun. 1, 1996;316 ( Pt 2):569-73.*
Bleackley et al, Isolation of two cDNA sequences which encode cytotoxic cell proteases. FEBS Lett. Jul. 4, 1988;234(1):153-9.*
Studier, et al., "Use of T7 RNA Polymerase to Direct Expression of Cloned Genes", Methods in Enzymology, vol. 185, p. 60-89, 1990.
Nykjaer, et al., "Purified α$_2$-Macroglobulin Receptor/LDL Receptor-related Protein Binds Urokinase Plasminogen Activator Inhibitor Type-1 Complex", The Journal of Biological Chemistry, vol. 267, No. 21, p. 14543-14546, Jul. 25, 1992.
Holtet, et al., "Tetranectin, a trimeric Plasminogen-binding C-type Lectin", Protein Science, vol. 6, p. 1511-1515, 1997.
Hochuli, et al., "Genetic Approach to Facilitate Purification of Recombinant Proteins with a Novel Metal Chelate Adsorbent", Biotechnology, p. 1321-1325, Nov. 1988.
Christensen, et al., "Sequence-Specific Binding of the N-Terminal Three-Finger Fragment of *Xenopus* Transcription Factor IIIA to the Internal Control Region of a 5S RNA Gene", Federation of European Biochemical Societies, vol. 281, No. 1-2, p. 181-184, Apr. 1991.
Casciola-Rosen, et al., "Cleavage by Granzyme B is Strongly Predictive of Autoantigen Status: Implications for Initiation of Autoimmunity", Journal of Experimental Medicine, vol. 190, No. 6, p. 815-825, Sep. 20, 1999.
Trapani, "Granzymes: a Family of Lymphocyte Granule Serine Proteases", Genome Biology, vol. 2, No. 12, 2001.

(Continued)

*Primary Examiner* — Sheridan Swope

(57) ABSTRACT

A method for the preparation of a polypeptide of interest in authentic form by enzymatic cleavage of fusion proteins using Granzyme B protease (EC 3.4.21.79). There is also provided fusion proteins comprising a polypeptide of interest and a fusion partner, wherein the junction region between the polypeptide of interest and the fusion partner comprises a Granzyme B protease cleavage site adjacent to the polypeptide of interest, and a human Granzyme B protease variant wherein the Cystein residue no. 228 (chymotrypsinogen numbering) is mutated to Phenylalanine.

24 Claims, 21 Drawing Sheets

(56) References Cited

OTHER PUBLICATIONS

Sun, et al. "Expression and Purification of Recombinant Human Granzyme B From *Pichia pastoris*", Biochemical and Biophysical Research Communications, vol. 261, p. 251-255, 1999.

Harris, et al., "Definition and Redesign of the Extended Substrate Specificity of Granzyme B", The Journal of Biological Chemistry, vol. 273, No. 42, p. 27364-27373, Oct. 16, 1998.

Sun, et al., "Importance of the P4' Residue in Human Granzyme B Inhibitors and Substrates Revealed by Scanning Mutagenesis of the Proteinase Inhibitor 9 Reactive Center Loop", The Journal of Biological Chemistry, vol. 276, No. 18, p. 15177-15184, May 4, 2001.

Rotonda, et al., "The Three-Dimensional Structure of Human Granzyme B Compared to Caspase-3, Key Mediators of Cell Death with Cleavage Specificity for Asparatic Acid in P1", Chemistry & Biology, vol. 8, p. 357-368, 2001.

Thornberry, et al., *A Combinatorial Approach Defines Specificities of Members of the Caspase Family and Granzyme B*, The Journal of Biological Chemistry, 272:17907-17911, 1997.

* cited by examiner (A)

(B)

(A)

(B)

SEQUENCE LISTING

<160> NUMBER OF SEQ ID NOS: 93

<210> SEQ ID NO 1
<211> LENGTH: 243
<212> TYPE: PRT
<213> ORGANISM: Artificial
<220> FEATURE:
<223> OTHER INFORMATION: Synthetic; pro-IEGR-GrB-H6

<400> SEQUENCE: 1

Met Gly Ser Ile Glu Gly Arg Ile Ile Gly Gly His Glu Ala Lys Pro
1               5                   10                  15

His Ser Arg Pro Tyr Met Ala Tyr Leu Met Ile Trp Asp Gln Lys Ser
            20                  25                  30

Leu Lys Arg Cys Gly Gly Phe Leu Ile Gln Asp Asp Phe Val Leu Thr
        35                  40                  45

Ala Ala His Cys Trp Gly Ser Ser Ile Asn Val Thr Leu Gly Ala His
    50                  55                  60

Asn Ile Lys Glu Gln Glu Pro Thr Gln Gln Phe Ile Pro Val Lys Arg
65                  70                  75                  80

Pro Ile Pro His Pro Ala Tyr Asn Pro Lys Asn Phe Ser Asn Asp Ile
                85                  90                  95

Met Leu Leu Gln Leu Glu Arg Lys Ala Lys Arg Thr Arg Ala Val Gln
            100                 105                 110

Pro Leu Arg Leu Pro Ser Asn Lys Ala Gln Val Lys Pro Gly Gln Thr
        115                 120                 125

Cys Ser Val Ala Gly Trp Gly Gln Thr Ala Pro Leu Gly Lys His Ser
    130                 135                 140

His Thr Leu Gln Glu Val Lys Met Thr Val Gln Glu Asp Arg Lys Cys
145                 150                 155                 160

Glu Ser Asp Leu Arg His Tyr Tyr Asp Ser Thr Ile Glu Leu Cys Val
                165                 170                 175

Gly Asp Pro Glu Ile Lys Lys Thr Ser Phe Lys Gly Asp Ser Gly Gly
            180                 185                 190

Pro Leu Val Cys Asn Lys Val Ala Gln Gly Ile Val Ser Tyr Gly Arg
        195                 200                 205

Asn Asn Gly Met Pro Pro Arg Ala Cys Thr Lys Val Ser Ser Phe Val
    210                 215                 220

His Trp Ile Lys Lys Thr Met Lys Arg Tyr Leu Asn Ser His His His
225                 230                 235                 240

His His His

<210> SEQ ID NO 2
<211> LENGTH: 243
<212> TYPE: PRT
<213> ORGANISM: Artificial
<220> FEATURE:
<223> OTHER INFORMATION: Synthetic; pro-IEPD-GrB-H6

<400> SEQUENCE: 2

Met Gly Ser Ile Glu Pro Asp Ile Ile Gly Gly His Glu Ala Lys Pro
1               5                   10                  15

His Ser Arg Pro Tyr Met Ala Tyr Leu Met Ile Trp Asp Gln Lys Ser
            20                  25                  30

Leu Lys Arg Cys Gly Gly Phe Leu Ile Gln Asp Asp Phe Val Leu Thr
        35                  40                  45

```
Ala Ala His Cys Trp Gly Ser Ser Ile Asn Val Thr Leu Gly Ala His
    50                  55                  60

Asn Ile Lys Glu Gln Glu Pro Thr Gln Gln Phe Ile Pro Val Lys Arg
 65                  70                  75                  80

Pro Ile Pro His Pro Ala Tyr Asn Pro Lys Asn Phe Ser Asn Asp Ile
                 85                  90                  95

Met Leu Gln Leu Glu Arg Lys Ala Lys Arg Thr Arg Ala Val Gln
                100                 105                 110

Pro Leu Arg Leu Pro Ser Asn Lys Ala Gln Val Lys Pro Gly Gln Thr
            115                 120                 125

Cys Ser Val Ala Gly Trp Gly Gln Thr Ala Pro Leu Gly Lys His Ser
    130                 135                 140

His Thr Leu Gln Glu Val Lys Met Thr Val Gln Glu Asp Arg Lys Cys
145                 150                 155                 160

Glu Ser Asp Leu Arg His Tyr Tyr Asp Ser Thr Ile Glu Leu Cys Val
                165                 170                 175

Gly Asp Pro Glu Ile Lys Lys Thr Ser Phe Lys Gly Asp Ser Gly Gly
            180                 185                 190

Pro Leu Val Cys Asn Lys Val Ala Gln Gly Ile Val Ser Tyr Gly Arg
        195                 200                 205

Asn Asn Gly Met Pro Pro Arg Ala Cys Thr Lys Val Ser Ser Phe Val
    210                 215                 220

His Trp Ile Lys Lys Thr Met Lys Arg Tyr Leu Asn Ser His His His
225                 230                 235                 240

His His His

<210> SEQ ID NO 3
<211> LENGTH: 243
<212> TYPE: PRT
<213> ORGANISM: Artificial
<220> FEATURE:
<223> OTHER INFORMATION: Synthetic; pro-IEAD-GrB-H6

<400> SEQUENCE: 3

Met Gly Ser Ile Glu Ala Asp Ile Ile Gly Gly His Glu Ala Lys Pro
  1               5                  10                  15

His Ser Arg Pro Tyr Met Ala Tyr Leu Met Ile Trp Asp Gln Lys Ser
                 20                  25                  30

Leu Lys Arg Cys Gly Gly Phe Leu Ile Gln Asp Asp Phe Val Leu Thr
            35                  40                  45

Ala Ala His Cys Trp Gly Ser Ser Ile Asn Val Thr Leu Gly Ala His
    50                  55                  60

Asn Ile Lys Glu Gln Glu Pro Thr Gln Gln Phe Ile Pro Val Lys Arg
 65                  70                  75                  80

Pro Ile Pro His Pro Ala Tyr Asn Pro Lys Asn Phe Ser Asn Asp Ile
                 85                  90                  95

Met Leu Leu Gln Leu Glu Arg Lys Ala Lys Arg Thr Arg Ala Val Gln
                100                 105                 110

Pro Leu Arg Leu Pro Ser Asn Lys Ala Gln Val Lys Pro Gly Gln Thr
            115                 120                 125

Cys Ser Val Ala Gly Trp Gly Gln Thr Ala Pro Leu Gly Lys His Ser
    130                 135                 140

His Thr Leu Gln Glu Val Lys Met Thr Val Gln Glu Asp Arg Lys Cys
145                 150                 155                 160

Glu Ser Asp Leu Arg His Tyr Tyr Asp Ser Thr Ile Glu Leu Cys Val
                165                 170                 175
```

```
Gly Asp Pro Glu Ile Lys Lys Thr Ser Phe Lys Gly Asp Ser Gly Gly
            180                 185                 190

Pro Leu Val Cys Asn Lys Val Ala Gln Gly Ile Val Ser Tyr Gly Arg
            195                 200                 205

Asn Asn Gly Met Pro Pro Arg Ala Cys Thr Lys Val Ser Ser Phe Val
210                 215                 220

His Trp Ile Lys Lys Thr Met Lys Arg Tyr Leu Asn Ser His His His
225                 230                 235                 240

His His His
```

<210> SEQ ID NO 4
<211> LENGTH: 243
<212> TYPE: PRT
<213> ORGANISM: Artificial
<220> FEATURE:
<223> OTHER INFORMATION: Synthetic; pro-IEPD-GrB-H6 C228S

<400> SEQUENCE: 4

```
Met Gly Ser Ile Glu Pro Asp Ile Ile Gly Gly His Glu Ala Lys Pro
1               5                   10                  15

His Ser Arg Pro Tyr Met Ala Tyr Leu Met Ile Trp Asp Gln Lys Ser
            20                  25                  30

Leu Lys Arg Cys Gly Gly Phe Leu Ile Gln Asp Asp Phe Val Leu Thr
        35                  40                  45

Ala Ala His Cys Trp Gly Ser Ser Ile Asn Val Thr Leu Gly Ala His
    50                  55                  60

Asn Ile Lys Glu Gln Glu Pro Thr Gln Gln Phe Ile Pro Val Lys Arg
65                  70                  75                  80

Pro Ile Pro His Pro Ala Tyr Asn Pro Lys Asn Phe Ser Asn Asp Ile
                85                  90                  95

Met Leu Leu Gln Leu Glu Arg Lys Ala Lys Arg Thr Arg Ala Val Gln
            100                 105                 110

Pro Leu Arg Leu Pro Ser Asn Lys Ala Gln Val Lys Pro Gly Gln Thr
        115                 120                 125

Cys Ser Val Ala Gly Trp Gly Gln Thr Ala Pro Leu Gly Lys His Ser
    130                 135                 140

His Thr Leu Gln Glu Val Lys Met Thr Val Gln Glu Asp Arg Lys Cys
145                 150                 155                 160

Glu Ser Asp Leu Arg His Tyr Tyr Asp Ser Thr Ile Glu Leu Cys Val
                165                 170                 175

Gly Asp Pro Glu Ile Lys Lys Thr Ser Phe Lys Gly Asp Ser Gly Gly
            180                 185                 190

Pro Leu Val Cys Asn Lys Val Ala Gln Gly Ile Val Ser Tyr Gly Arg
        195                 200                 205

Asn Asn Gly Met Pro Pro Arg Ala Ser Thr Lys Val Ser Ser Phe Val
    210                 215                 220

His Trp Ile Lys Lys Thr Met Lys Arg Tyr Leu Asn Ser His His His
225                 230                 235                 240

His His His
```

<210> SEQ ID NO 5
<211> LENGTH: 243
<212> TYPE: PRT
<213> ORGANISM: Artificial
<220> FEATURE:
<223> OTHER INFORMATION: Synthetic; pro-IEPD-GrB-H6 C228A

<400> SEQUENCE: 5

```
Met Gly Ser Ile Glu Pro Asp Ile Ile Gly Gly His Glu Ala Lys Pro
1               5                   10                  15

His Ser Arg Pro Tyr Met Ala Tyr Leu Met Ile Trp Asp Gln Lys Ser
            20                  25                  30

Leu Lys Arg Cys Gly Gly Phe Leu Ile Gln Asp Asp Phe Val Leu Thr
        35                  40                  45

Ala Ala His Cys Trp Gly Ser Ser Ile Asn Val Thr Leu Gly Ala His
    50                  55                  60

Asn Ile Lys Glu Gln Glu Pro Thr Gln Gln Phe Ile Pro Val Lys Arg
65                  70                  75                  80

Pro Ile Pro His Pro Ala Tyr Asn Pro Lys Asn Phe Ser Asn Asp Ile
                85                  90                  95

Met Leu Leu Gln Leu Glu Arg Lys Ala Lys Arg Thr Arg Ala Val Gln
            100                 105                 110

Pro Leu Arg Leu Pro Ser Asn Lys Ala Gln Val Lys Pro Gly Gln Thr
        115                 120                 125

Cys Ser Val Ala Gly Trp Gly Gln Thr Ala Pro Leu Gly Lys His Ser
    130                 135                 140

His Thr Leu Gln Glu Val Lys Met Thr Val Gln Glu Asp Arg Lys Cys
145                 150                 155                 160

Glu Ser Asp Leu Arg His Tyr Tyr Asp Ser Thr Ile Glu Leu Cys Val
                165                 170                 175

Gly Asp Pro Glu Ile Lys Lys Thr Ser Phe Lys Gly Asp Ser Gly Gly
            180                 185                 190

Pro Leu Val Cys Asn Lys Val Ala Gln Gly Ile Val Ser Tyr Gly Arg
        195                 200                 205

Asn Asn Gly Met Pro Pro Arg Ala Ala Thr Lys Val Ser Ser Phe Val
210                 215                 220

His Trp Ile Lys Lys Thr Met Lys Arg Tyr Leu Asn Ser His His His
225                 230                 235                 240

His His His
```

<210> SEQ ID NO 6
<211> LENGTH: 243
<212> TYPE: PRT
<213> ORGANISM: Artificial
<220> FEATURE:
<223> OTHER INFORMATION: Synthetic; pro-IEPD-GrB-H6 C228T

<400> SEQUENCE: 6

```
Met Gly Ser Ile Glu Pro Asp Ile Ile Gly Gly His Glu Ala Lys Pro
1               5                   10                  15

His Ser Arg Pro Tyr Met Ala Tyr Leu Met Ile Trp Asp Gln Lys Ser
            20                  25                  30

Leu Lys Arg Cys Gly Gly Phe Leu Ile Gln Asp Asp Phe Val Leu Thr
        35                  40                  45

Ala Ala His Cys Trp Gly Ser Ser Ile Asn Val Thr Leu Gly Ala His
    50                  55                  60

Asn Ile Lys Glu Gln Glu Pro Thr Gln Gln Phe Ile Pro Val Lys Arg
65                  70                  75                  80

Pro Ile Pro His Pro Ala Tyr Asn Pro Lys Asn Phe Ser Asn Asp Ile
                85                  90                  95

Met Leu Leu Gln Leu Glu Arg Lys Ala Lys Arg Thr Arg Ala Val Gln
            100                 105                 110
```

```
Pro Leu Arg Leu Pro Ser Asn Lys Ala Gln Val Lys Pro Gly Gln Thr
        115                 120                 125

Cys Ser Val Ala Gly Trp Gly Gln Thr Ala Pro Leu Gly Lys His Ser
    130                 135                 140

His Thr Leu Gln Glu Val Lys Met Thr Val Gln Glu Asp Arg Lys Cys
145                 150                 155                 160

Glu Ser Asp Leu Arg His Tyr Tyr Asp Ser Thr Ile Glu Leu Cys Val
                165                 170                 175

Gly Asp Pro Glu Ile Lys Lys Thr Ser Phe Lys Gly Asp Ser Gly Gly
                180                 185                 190

Pro Leu Val Cys Asn Lys Val Ala Gln Gly Ile Val Ser Tyr Gly Arg
            195                 200                 205

Asn Asn Gly Met Pro Pro Arg Ala Thr Thr Lys Val Ser Ser Phe Val
            210                 215                 220

His Trp Ile Lys Lys Thr Met Lys Arg Tyr Leu Asn Ser His His His
225                 230                 235                 240

His His His

<210> SEQ ID NO 7
<211> LENGTH: 243
<212> TYPE: PRT
<213> ORGANISM: Artificial
<220> FEATURE:
<223> OTHER INFORMATION: Synthetic; pro-IEPD-GrB-H6 C228V

<400> SEQUENCE: 7

Met Gly Ser Ile Glu Pro Asp Ile Ile Gly Gly His Glu Ala Lys Pro
1               5                   10                  15

His Ser Arg Pro Tyr Met Ala Tyr Leu Met Ile Trp Asp Gln Lys Ser
            20                  25                  30

Leu Lys Arg Cys Gly Gly Phe Leu Ile Gln Asp Asp Phe Val Leu Thr
        35                  40                  45

Ala Ala His Cys Trp Gly Ser Ser Ile Asn Val Thr Leu Gly Ala His
    50                  55                  60

Asn Ile Lys Glu Gln Glu Pro Thr Gln Gln Phe Ile Pro Val Lys Arg
65                  70                  75                  80

Pro Ile Pro His Pro Ala Tyr Asn Pro Lys Asn Phe Ser Asn Asp Ile
                85                  90                  95

Met Leu Leu Gln Leu Glu Arg Lys Ala Lys Arg Thr Arg Ala Val Gln
                100                 105                 110

Pro Leu Arg Leu Pro Ser Asn Lys Ala Gln Val Lys Pro Gly Gln Thr
        115                 120                 125

Cys Ser Val Ala Gly Trp Gly Gln Thr Ala Pro Leu Gly Lys His Ser
    130                 135                 140

His Thr Leu Gln Glu Val Lys Met Thr Val Gln Glu Asp Arg Lys Cys
145                 150                 155                 160

Glu Ser Asp Leu Arg His Tyr Tyr Asp Ser Thr Ile Glu Leu Cys Val
                165                 170                 175

Gly Asp Pro Glu Ile Lys Lys Thr Ser Phe Lys Gly Asp Ser Gly Gly
                180                 185                 190

Pro Leu Val Cys Asn Lys Val Ala Gln Gly Ile Val Ser Tyr Gly Arg
            195                 200                 205

Asn Asn Gly Met Pro Pro Arg Ala Val Thr Lys Val Ser Ser Phe Val
            210                 215                 220

His Trp Ile Lys Lys Thr Met Lys Arg Tyr Leu Asn Ser His His His
225                 230                 235                 240
```

His His His

<210> SEQ ID NO 8
<211> LENGTH: 243
<212> TYPE: PRT
<213> ORGANISM: Artificial
<220> FEATURE:
<223> OTHER INFORMATION: Synthetic; pro-IEPD-GrB-H6 C228F

<400> SEQUENCE: 8

Met Gly Ser Ile Glu Pro Asp Ile Ile Gly Gly His Glu Ala Lys Pro
1               5                   10                  15

His Ser Arg Pro Tyr Met Ala Tyr Leu Met Ile Trp Asp Gln Lys Ser
            20                  25                  30

Leu Lys Arg Cys Gly Gly Phe Leu Ile Gln Asp Asp Phe Val Leu Thr
        35                  40                  45

Ala Ala His Cys Trp Gly Ser Ser Ile Asn Val Thr Leu Gly Ala His
    50                  55                  60

Asn Ile Lys Glu Gln Glu Pro Thr Gln Gln Phe Ile Pro Val Lys Arg
65                  70                  75                  80

Pro Ile Pro His Pro Ala Tyr Asn Pro Lys Asn Phe Ser Asn Asp Ile
                85                  90                  95

Met Leu Leu Gln Leu Glu Arg Lys Ala Lys Arg Thr Arg Ala Val Gln
            100                 105                 110

Pro Leu Arg Leu Pro Ser Asn Lys Ala Gln Val Lys Pro Gly Gln Thr
        115                 120                 125

Cys Ser Val Ala Gly Trp Gly Gln Thr Ala Pro Leu Gly Lys His Ser
    130                 135                 140

His Thr Leu Gln Glu Val Lys Met Thr Val Gln Glu Asp Arg Lys Cys
145                 150                 155                 160

Glu Ser Asp Leu Arg His Tyr Tyr Asp Ser Thr Ile Glu Leu Cys Val
                165                 170                 175

Gly Asp Pro Glu Ile Lys Lys Thr Ser Phe Lys Gly Asp Ser Gly Gly
            180                 185                 190

Pro Leu Val Cys Asn Lys Val Ala Gln Gly Ile Val Ser Tyr Gly Arg
        195                 200                 205

Asn Asn Gly Met Pro Pro Arg Ala Phe Thr Lys Val Ser Ser Phe Val
    210                 215                 220

His Trp Ile Lys Lys Thr Met Lys Arg Tyr Leu Asn Ser His His His
225                 230                 235                 240

His His His

<210> SEQ ID NO 9
<211> LENGTH: 46
<212> TYPE: DNA
<213> ORGANISM: Artificial
<220> FEATURE:
<223> OTHER INFORMATION: Synthetic; H6 C-term fw

<400> SEQUENCE: 9
catggacgga agcttgaatt cacatcacca tcaccatcac taacgc        46

<210> SEQ ID NO 10
<211> LENGTH: 46
<212> TYPE: DNA
<213> ORGANISM: Artificial
<220> FEATURE:
<223> OTHER INFORMATION: Synthetic; H6 C-term rev

```
<400> SEQUENCE: 10
aattgcgtta gtgatggtga tggtgatgtg aattcaagct tccgct          46

<210> SEQ ID NO 11
<211> LENGTH: 40
<212> TYPE: DNA
<213> ORGANISM: Artificial
<220> FEATURE:
<223> OTHER INFORMATION: Synthetic; GrBfw primer

<400> SEQUENCE: 11
catgggatcc atcgagggta ggatcatcgg gggacatgag                  40

<210> SEQ ID NO 12
<211> LENGTH: 38
<212> TYPE: DNA
<213> ORGANISM: Artificial
<220> FEATURE:
<223> OTHER INFORMATION: Synthetic; GrBrev EcoRI primer

<400> SEQUENCE: 12
gcgtgaattc aggtaccgtt tcatggtttt ctttatcc                    38

<210> SEQ ID NO 13
<211> LENGTH: 715
<212> TYPE: DNA
<213> ORGANISM: Artificial
<220> FEATURE:
<223> OTHER INFORMATION: Synthetic; GrB EcoRI fragment

<400> SEQUENCE: 13
catgggatcc atcgagggta ggatcatcgg gggacatgag gccaagcccc actcccgccc    60
ctacatggct tatcttatga tctgggatca gaagtctctg aagaggtgcg gtggcttcct   120
gatacaagac gacttcgtgc tgacagctgc tcactgttgg ggaagctcca taaatgtcac   180
cttgggggcc cacaatatca agaacagga gccgacccag cagtttatcc ctgtgaaaag   240
acccatcccc catccagcct ataatcctaa gaacttctcc aacgacatca tgctactgca   300
gctggagaga aaggccaagc ggaccagagc tgtgcagccc tcaggctac ctagcaacaa   360 ggcccaggtg aagccagggc agacatgcag tgtggccggc tgggggcaga cggcccccct   420
gggaaaacac tcacacacac tacaagaggt gaagatgaca gtgcaggaag atcgaaagtg   480
cgaatctgac ttacgccatt attacgacag taccattgag ttgtgcgtgg gggacccaga   540
gattaaaaag acttccttta aggggactc tggaggccct cttgtgtgta acaaggtggc   600
ccagggcatt gtctcctatg acgaaacaa tggcatgcct ccacgagcct gcaccaaagt   660
ctcaagcttt gtacactgga taagaaaac catgaaacgg tacctgaatt cacgc        715

<210> SEQ ID NO 14
<211> LENGTH: 33
<212> TYPE: DNA
<213> ORGANISM: Artificial
<220> FEATURE:
<223> OTHER INFORMATION: Synthetic; GrB GR-PD fw

<400> SEQUENCE: 14
tccatcgagc cggatatcat cgggggacat gag                         33

<210> SEQ ID NO 15
<211> LENGTH: 34
<212> TYPE: DNA
<213> ORGANISM: Artificial
<220> FEATURE:
```

<223> OTHER INFORMATION: Synthetic; GrB GR-PD rev

<400> SEQUENCE: 15
ccccgatgat atccggctcg atggatccca tatg            34

<210> SEQ ID NO 16
<211> LENGTH: 33
<212> TYPE: DNA
<213> ORGANISM: Artificial
<220> FEATURE:
<223> OTHER INFORMATION: Synthetic; GrB GR-AD fw

<400> SEQUENCE: 16
tccatcgagg ctgatatcat cggggacat gag              33

<210> SEQ ID NO 17
<211> LENGTH: 34
<212> TYPE: DNA
<213> ORGANISM: Artificial
<220> FEATURE:
<223> OTHER INFORMATION: Synthetic; GrB GR-AD rev

<400> SEQUENCE: 17
ccccgatgat atcagcctcg atggatccca tatg            34

<210> SEQ ID NO 18
<211> LENGTH: 27
<212> TYPE: DNA
<213> ORGANISM: Artificial
<220> FEATURE:
<223> OTHER INFORMATION: Synthetic; GrB SAT fw

<400> SEQUENCE: 18
tccacgagca dccaccaaag tctcaag                    27

<210> SEQ ID NO 19
<211> LENGTH: 26
<212> TYPE: DNA
<213> ORGANISM: Artificial
<220> FEATURE:
<223> OTHER INFORMATION: Synthetic; GrB SAT rev

<400> SEQUENCE: 19
agactttggt gghggctcgt ggaggc                     26

<210> SEQ ID NO 20
<211> LENGTH: 27
<212> TYPE: DNA
<213> ORGANISM: Artificial
<220> FEATURE:
<223> OTHER INFORMATION: Synthetic; GrB VF fw

<400> SEQUENCE: 20
tccacgagcc ktcaccaaag tctcaag                    27

<210> SEQ ID NO 21
<211> LENGTH: 26
<212> TYPE: DNA
<213> ORGANISM: Artificial
<220> FEATURE:
<223> OTHER INFORMATION: Synthetic; GrB VF rev

<400> SEQUENCE: 21
agactttggt gamggctcgt ggaggc                     26

<210> SEQ ID NO 22

```
<211> LENGTH: 150
<212> TYPE: PRT
<213> ORGANISM: Artificial
<220> FEATURE:
<223> OTHER INFORMATION: Synthetic; H6-TripUB IEPDSP

<400> SEQUENCE: 22

Met Gly Ser His His His His His Gly Ser Gly Ser Gly Ser Ile
1               5                   10                  15

Glu Pro Asp Ser Pro Gly Thr Glu Pro Thr Gln Lys Pro Lys Lys
                20                  25                  30

Ile Val Asn Ala Lys Lys Asp Val Val Asn Thr Lys Met Phe Glu Glu
                35                  40                  45

Leu Lys Ser Arg Leu Asp Thr Leu Ala Gln Glu Val Ala Leu Leu Lys
    50                  55                  60

Glu Gln Gln Ala Leu Gln Thr Val Gly Ser Gln Ile Phe Val Lys Thr
65                  70                  75                  80

Leu Thr Gly Lys Thr Ile Thr Leu Glu Val Glu Pro Ser Asp Thr Ile
                85                  90                  95

Glu Asn Val Lys Ala Lys Ile Gln Asp Lys Glu Gly Ile Pro Pro Asp
                100                 105                 110

Gln Gln Arg Leu Ile Phe Ala Gly Lys Gln Leu Glu Asp Gly Arg Thr
            115                 120                 125

Leu Ser Asp Tyr Asn Ile Gln Lys Glu Ser Thr Leu His Leu Val Leu
    130                 135                 140

Arg Leu Arg Gly Gly Ser
145                 150

<210> SEQ ID NO 23
<211> LENGTH: 338
<212> TYPE: PRT
<213> ORGANISM: Artificial
<220> FEATURE:
<223> OTHER INFORMATION: Synthetic; H6-IEPD-RAP

<400> SEQUENCE: 23

Met Gly Ser His His His His His Gly Ser Ile Glu Pro Asp Tyr
1               5                   10                  15

Ser Arg Glu Lys Asn Gln Pro Lys Pro Ser Pro Lys Arg Glu Ser Gly
                20                  25                  30

Glu Glu Phe Arg Met Glu Lys Leu Asn Gln Leu Trp Glu Lys Ala Gln
            35                  40                  45

Arg Leu His Leu Pro Pro Val Arg Leu Ala Glu His Ala Asp Leu
    50                  55                  60

Lys Ile Gln Glu Arg Asp Glu Leu Ala Trp Lys Lys Leu Lys Leu Asp
65                  70                  75                  80

Gly Leu Asp Glu Asp Gly Glu Lys Glu Ala Arg Leu Ile Arg Asn Leu
                85                  90                  95

Asn Val Ile Leu Ala Lys Tyr Gly Leu Asp Gly Lys Lys Asp Ala Arg
                100                 105                 110

Gln Val Thr Ser Asn Ser Leu Ser Gly Thr Gln Glu Asp Gly Leu Asp
            115                 120                 125

Asp Pro Arg Leu Glu Lys Leu Trp His Lys Ala Lys Thr Ser Gly Lys
    130                 135                 140

Phe Ser Gly Glu Glu Leu Asp Lys Leu Trp Arg Glu Phe Leu His His
145                 150                 155                 160

Lys Glu Lys Val His Glu Tyr Asn Val Leu Leu Glu Thr Leu Ser Arg
                165                 170                 175
```

```
Thr Glu Glu Ile His Glu Asn Val Ile Ser Pro Ser Asp Leu Ser Asp
            180                 185                 190

Ile Lys Gly Ser Val Leu His Ser Arg His Thr Glu Leu Lys Glu Lys
        195                 200                 205

Leu Arg Ser Ile Asn Gln Gly Leu Asp Arg Leu Arg Arg Val Ser His
    210                 215                 220

Gln Gly Tyr Ser Thr Glu Ala Glu Phe Glu Glu Pro Arg Val Ile Asp
225                 230                 235                 240

Leu Trp Asp Leu Ala Gln Ser Ala Asn Leu Thr Asp Lys Glu Leu Glu
                245                 250                 255

Ala Phe Arg Glu Glu Leu Lys His Phe Glu Ala Lys Ile Glu Lys His
            260                 265                 270

Asn His Tyr Gln Lys Gln Leu Glu Ile Ala His Glu Lys Leu Arg His
        275                 280                 285

Ala Glu Ser Val Gly Asp Gly Glu Arg Val Ser Arg Ser Arg Glu Lys
    290                 295                 300

His Ala Leu Leu Glu Gly Arg Thr Lys Glu Leu Gly Tyr Thr Val Lys
305                 310                 315                 320

Lys His Leu Gln Asp Leu Ser Gly Arg Ile Ser Arg Ala Arg His Asn
                325                 330                 335

Glu Leu

<210> SEQ ID NO 24
<211> LENGTH: 336
<212> TYPE: PRT
<213> ORGANISM: Artificial
<220> FEATURE:
<223> OTHER INFORMATION: Synthetic; H6Ubi-IEPD-ApoA1

<400> SEQUENCE: 24

Met Gly Ser His His His His His Gly Ser Gln Ile Phe Val Lys
1               5                   10                  15

Thr Leu Thr Gly Lys Thr Ile Thr Leu Glu Val Glu Pro Ser Asp Thr
            20                  25                  30

Ile Glu Asn Val Lys Ala Lys Ile Gln Asp Lys Glu Gly Ile Pro Pro
        35                  40                  45

Asp Gln Gln Arg Leu Ile Phe Ala Gly Lys Gln Leu Glu Asp Gly Arg
    50                  55                  60

Thr Leu Ser Asp Tyr Asn Ile Gln Lys Glu Ser Thr Leu His Leu Val
65                  70                  75                  80

Leu Arg Leu Arg Gly Gly Ser Ile Glu Pro Asp Gly Gly Asp Glu Pro
                85                  90                  95

Pro Gln Ser Pro Trp Asp Arg Val Lys Asp Leu Ala Thr Val Tyr Val
            100                 105                 110

Asp Val Leu Lys Asp Ser Gly Arg Asp Tyr Val Ser Gln Phe Glu Gly
        115                 120                 125

Ser Ala Leu Gly Lys Gln Leu Asn Leu Lys Leu Leu Asp Asn Trp Asp
    130                 135                 140

Ser Val Thr Ser Thr Phe Ser Lys Leu Arg Glu Gln Leu Gly Pro Val
145                 150                 155                 160

Thr Gln Glu Phe Trp Asp Asn Leu Glu Lys Thr Glu Gly Leu Arg
                165                 170                 175

Gln Glu Met Ser Lys Asp Leu Glu Glu Val Lys Ala Lys Val Gln Pro
            180                 185                 190

Tyr Leu Asp Asp Phe Gln Lys Lys Trp Gln Glu Glu Met Glu Leu Tyr
```

```
            195                 200                 205
Arg Gln Lys Val Glu Pro Leu Arg Ala Glu Leu Gln Glu Gly Ala Arg
        210                 215                 220

Gln Lys Leu His Glu Leu Gln Glu Lys Leu Ser Pro Leu Gly Glu Glu
225                 230                 235                 240

Met Arg Asp Arg Ala Arg Ala His Val Asp Ala Leu Arg Thr His Leu
                245                 250                 255

Ala Pro Tyr Ser Asp Glu Leu Arg Gln Arg Leu Ala Ala Arg Leu Glu
            260                 265                 270

Ala Leu Lys Glu Asn Gly Gly Ala Arg Leu Ala Glu Tyr His Ala Lys
        275                 280                 285

Ala Thr Glu His Leu Ser Thr Leu Ser Glu Lys Ala Lys Pro Ala Leu
    290                 295                 300

Glu Asp Leu Arg Gln Gly Leu Leu Pro Val Leu Glu Ser Phe Lys Val
305                 310                 315                 320

Ser Phe Leu Ser Ala Leu Glu Glu Tyr Thr Lys Lys Leu Asn Thr Gln
                325                 330                 335

<210> SEQ ID NO 25
<211> LENGTH: 197
<212> TYPE: PRT
<213> ORGANISM: Artificial
<220> FEATURE:
<223> OTHER INFORMATION: Synthetic; H6-IEPD-TN123

<400> SEQUENCE: 25

Met Gly Ser His His His His His His Gly Ser Ile Glu Pro Asp Gly
1               5                   10                  15

Glu Pro Pro Thr Gln Lys Pro Lys Lys Ile Val Asn Ala Lys Lys Asp
            20                  25                  30

Val Val Asn Thr Lys Met Phe Glu Glu Leu Lys Ser Arg Leu Asp Thr
        35                  40                  45

Leu Ala Gln Glu Val Ala Leu Leu Lys Glu Gln Gln Ala Leu Gln Thr
    50                  55                  60

Val Cys Leu Lys Gly Thr Lys Val His Met Lys Cys Phe Leu Ala Phe
65                  70                  75                  80

Thr Gln Thr Lys Thr Phe His Glu Ala Ser Glu Asp Cys Ile Ser Arg
                85                  90                  95

Gly Gly Thr Leu Ser Thr Pro Gln Thr Gly Ser Glu Asn Asp Ala Leu
            100                 105                 110

Tyr Glu Tyr Leu Arg Gln Ser Val Gly Asn Glu Ala Glu Ile Trp Leu
        115                 120                 125

Gly Leu Asn Asp Met Ala Ala Glu Gly Thr Trp Val Asp Met Thr Gly
    130                 135                 140

Ala Arg Ile Ala Tyr Lys Asn Trp Glu Thr Glu Ile Thr Ala Gln Pro
145                 150                 155                 160

Asp Gly Gly Lys Thr Glu Asn Cys Ala Val Leu Ser Gly Ala Ala Asn
                165                 170                 175

Gly Lys Trp Phe Asp Lys Arg Cys Arg Asp Gln Leu Pro Tyr Ile Cys
            180                 185                 190

Gln Phe Gly Ile Val
        195

<210> SEQ ID NO 26
<211> LENGTH: 150
<212> TYPE: PRT
<213> ORGANISM: Artificial
```

<220> FEATURE:
<223> OTHER INFORMATION: Synthetic; H6-TripUB IQADSP

<400> SEQUENCE: 26

Met Gly Ser His His His His His Gly Ser Gly Ser Gly Ser Ile
1               5                   10                  15

Gln Ala Asp Ser Pro Gly Thr Glu Pro Pro Thr Gln Lys Pro Lys Lys
            20                  25                  30

Ile Val Asn Ala Lys Lys Asp Val Val Asn Thr Lys Met Phe Glu Glu
        35                  40                  45

Leu Lys Ser Arg Leu Asp Thr Leu Ala Gln Glu Val Ala Leu Leu Lys
    50                  55                  60

Glu Gln Gln Ala Leu Gln Thr Val Gly Ser Gln Ile Phe Val Lys Thr
65                  70                  75                  80

Leu Thr Gly Lys Thr Ile Thr Leu Glu Val Glu Pro Ser Asp Thr Ile
                85                  90                  95

Glu Asn Val Lys Ala Lys Ile Gln Asp Lys Glu Gly Ile Pro Pro Asp
            100                 105                 110

Gln Gln Arg Leu Ile Phe Ala Gly Lys Gln Leu Glu Asp Gly Arg Thr
        115                 120                 125

Leu Ser Asp Tyr Asn Ile Gln Lys Glu Ser Thr Leu His Leu Val Leu
    130                 135                 140

Arg Leu Arg Gly Gly Ser
145                 150

<210> SEQ ID NO 27
<211> LENGTH: 150
<212> TYPE: PRT
<213> ORGANISM: Artificial
<220> FEATURE:
<223> OTHER INFORMATION: Synthetic; H6-TripUB IQADSG

<400> SEQUENCE: 27

Met Gly Ser His His His His His Gly Ser Gly Ser Gly Ser Ile
1               5                   10                  15

Gln Ala Asp Ser Gly Gly Thr Glu Pro Pro Thr Gln Lys Pro Lys Lys
            20                  25                  30

Ile Val Asn Ala Lys Lys Asp Val Val Asn Thr Lys Met Phe Glu Glu
        35                  40                  45

Leu Lys Ser Arg Leu Asp Thr Leu Ala Gln Glu Val Ala Leu Leu Lys
    50                  55                  60

Glu Gln Gln Ala Leu Gln Thr Val Gly Ser Gln Ile Phe Val Lys Thr
65                  70                  75                  80

Leu Thr Gly Lys Thr Ile Thr Leu Glu Val Glu Pro Ser Asp Thr Ile
                85                  90                  95

Glu Asn Val Lys Ala Lys Ile Gln Asp Lys Glu Gly Ile Pro Pro Asp
            100                 105                 110

Gln Gln Arg Leu Ile Phe Ala Gly Lys Gln Leu Glu Asp Gly Arg Thr
        115                 120                 125

Leu Ser Asp Tyr Asn Ile Gln Lys Glu Ser Thr Leu His Leu Val Leu
    130                 135                 140

Arg Leu Arg Gly Gly Ser
145                 150

<210> SEQ ID NO 28
<211> LENGTH: 150
<212> TYPE: PRT
<213> ORGANISM: Artificial

```
<220> FEATURE:
<223> OTHER INFORMATION: Synthetic; H6-TripUB VGPDSP

<400> SEQUENCE: 28

Met Gly Ser His His His His His Gly Ser Gly Ser Gly Ser Val
1               5                   10                  15

Gly Pro Asp Ser Pro Gly Thr Glu Pro Pro Thr Gln Lys Pro Lys Lys
            20                  25                  30

Ile Val Asn Ala Lys Lys Asp Val Val Asn Thr Lys Met Phe Glu Glu
                35                  40                  45

Leu Lys Ser Arg Leu Asp Thr Leu Ala Gln Glu Val Ala Leu Leu Lys
        50                  55                  60

Glu Gln Gln Ala Leu Gln Thr Val Gly Ser Gln Ile Phe Val Lys Thr
65                  70                  75                  80

Leu Thr Gly Lys Thr Ile Thr Leu Glu Val Glu Pro Ser Asp Thr Ile
                85                  90                  95

Glu Asn Val Lys Ala Lys Ile Gln Asp Lys Glu Gly Ile Pro Pro Asp
                100                 105                 110

Gln Gln Arg Leu Ile Phe Ala Gly Lys Gln Leu Glu Asp Gly Arg Thr
            115                 120                 125

Leu Ser Asp Tyr Asn Ile Gln Lys Glu Ser Thr Leu His Leu Val Leu
        130                 135                 140

Arg Leu Arg Gly Gly Ser
145                 150

<210> SEQ ID NO 29
<211> LENGTH: 150
<212> TYPE: PRT
<213> ORGANISM: Artificial
<220> FEATURE:
<223> OTHER INFORMATION: Synthetic; H6-TripUB VGPDFG

<400> SEQUENCE: 29

Met Gly Ser His His His His His Gly Ser Gly Ser Gly Ser Val
1               5                   10                  15

Gly Pro Asp Phe Gly Gly Thr Glu Pro Pro Thr Gln Lys Pro Lys Lys
            20                  25                  30

Ile Val Asn Ala Lys Lys Asp Val Val Asn Thr Lys Met Phe Glu Glu
                35                  40                  45

Leu Lys Ser Arg Leu Asp Thr Leu Ala Gln Glu Val Ala Leu Leu Lys
        50                  55                  60

Glu Gln Gln Ala Leu Gln Thr Val Gly Ser Gln Ile Phe Val Lys Thr
65                  70                  75                  80

Leu Thr Gly Lys Thr Ile Thr Leu Glu Val Glu Pro Ser Asp Thr Ile
                85                  90                  95

Glu Asn Val Lys Ala Lys Ile Gln Asp Lys Glu Gly Ile Pro Pro Asp
                100                 105                 110

Gln Gln Arg Leu Ile Phe Ala Gly Lys Gln Leu Glu Asp Gly Arg Thr
            115                 120                 125

Leu Ser Asp Tyr Asn Ile Gln Lys Glu Ser Thr Leu His Leu Val Leu
        130                 135                 140

Arg Leu Arg Gly Gly Ser
145                 150

<210> SEQ ID NO 30
<211> LENGTH: 143
<212> TYPE: PRT
<213> ORGANISM: Artificial
```

```
<220> FEATURE:
<223> OTHER INFORMATION: Synthetic; H6-TripUB IEPDTQ

<400> SEQUENCE: 30

Met Gly Ser His His His His His Gly Ser Gly Ser Gly Ser Ile
1               5                   10                  15

Glu Pro Asp Thr Gln Lys Pro Lys Ile Val Asn Ala Lys Lys Asp
                20                  25                  30

Val Val Asn Thr Lys Met Phe Glu Glu Leu Lys Ser Arg Leu Asp Thr
            35                  40                  45

Leu Ala Gln Glu Val Ala Leu Leu Lys Glu Gln Gln Ala Leu Gln Thr
        50                  55                  60

Val Gly Ser Gln Ile Phe Val Lys Thr Leu Thr Gly Lys Thr Ile Thr
65                  70                  75                  80

Leu Glu Val Glu Pro Ser Asp Thr Ile Glu Asn Val Lys Ala Lys Ile
                85                  90                  95

Gln Asp Lys Glu Gly Ile Pro Pro Asp Gln Gln Arg Leu Ile Phe Ala
            100                 105                 110

Gly Lys Gln Leu Glu Asp Gly Arg Thr Leu Ser Asp Tyr Asn Ile Gln
        115                 120                 125

Lys Glu Ser Thr Leu His Leu Val Leu Arg Leu Arg Gly Gly Ser
    130                 135                 140

<210> SEQ ID NO 31
<211> LENGTH: 137
<212> TYPE: PRT
<213> ORGANISM: Artificial
<220> FEATURE:
<223> OTHER INFORMATION: Synthetic; H6-TripUB IEPDIV

<400> SEQUENCE: 31

Met Gly Ser His His His His His Gly Ser Gly Ser Gly Ser Ile
1               5                   10                  15

Glu Pro Asp Ile Val Asn Ala Lys Lys Asp Val Val Asn Thr Lys Met
                20                  25                  30

Phe Glu Glu Leu Lys Ser Arg Leu Asp Thr Leu Ala Gln Glu Val Ala
            35                  40                  45

Leu Leu Lys Glu Gln Gln Ala Leu Gln Thr Val Gly Ser Gln Ile Phe
        50                  55                  60

Val Lys Thr Leu Thr Gly Lys Thr Ile Thr Leu Glu Val Glu Pro Ser
65                  70                  75                  80

Asp Thr Ile Glu Asn Val Lys Ala Lys Ile Gln Asp Lys Glu Gly Ile
                85                  90                  95

Pro Pro Asp Gln Gln Arg Leu Ile Phe Ala Gly Lys Gln Leu Glu Asp
            100                 105                 110

Gly Arg Thr Leu Ser Asp Tyr Asn Ile Gln Lys Glu Ser Thr Leu His
        115                 120                 125

Leu Val Leu Arg Leu Arg Gly Gly Ser
    130                 135

<210> SEQ ID NO 32
<211> LENGTH: 150
<212> TYPE: PRT
<213> ORGANISM: Artificial
<220> FEATURE:
<223> OTHER INFORMATION: Synthetic; H6-TripUB IEPDEP

<400> SEQUENCE: 32

Met Gly Ser His His His His His Gly Ser Gly Ser Gly Ser Ile
```

```
                1               5                   10                  15
Glu Pro Asp Glu Pro Gly Thr Glu Pro Pro Thr Gln Lys Pro Lys Lys
            20                  25                  30

Ile Val Asn Ala Lys Lys Asp Val Val Asn Thr Lys Met Phe Glu Glu
            35                  40                  45

Leu Lys Ser Arg Leu Asp Thr Leu Ala Gln Glu Val Ala Leu Leu Lys
            50                  55                  60

Glu Gln Gln Ala Leu Gln Thr Val Gly Ser Gln Ile Phe Val Lys Thr
65                  70                  75                  80

Leu Thr Gly Lys Thr Ile Thr Leu Glu Val Glu Pro Ser Asp Thr Ile
                85                  90                  95

Glu Asn Val Lys Ala Lys Ile Gln Asp Lys Glu Gly Ile Pro Pro Asp
                100                 105                 110

Gln Gln Arg Leu Ile Phe Ala Gly Lys Gln Leu Glu Asp Gly Arg Thr
                115                 120                 125

Leu Ser Asp Tyr Asn Ile Gln Lys Glu Ser Thr Leu His Leu Val Leu
                130                 135                 140

Arg Leu Arg Gly Gly Ser
145                 150

<210> SEQ ID NO 33
<211> LENGTH: 150
<212> TYPE: PRT
<213> ORGANISM: Artificial
<220> FEATURE:
<223> OTHER INFORMATION: Synthetic; H6-TripUB IEPDEG

<400> SEQUENCE: 33

Met Gly Ser His His His His His Gly Ser Gly Ser Gly Ser Ile
1               5                   10                  15

Glu Pro Asp Glu Gly Gly Thr Glu Pro Pro Thr Gln Lys Pro Lys Lys
            20                  25                  30

Ile Val Asn Ala Lys Lys Asp Val Val Asn Thr Lys Met Phe Glu Glu
            35                  40                  45

Leu Lys Ser Arg Leu Asp Thr Leu Ala Gln Glu Val Ala Leu Leu Lys
            50                  55                  60

Glu Gln Gln Ala Leu Gln Thr Val Gly Ser Gln Ile Phe Val Lys Thr
65                  70                  75                  80

Leu Thr Gly Lys Thr Ile Thr Leu Glu Val Glu Pro Ser Asp Thr Ile
                85                  90                  95

Glu Asn Val Lys Ala Lys Ile Gln Asp Lys Glu Gly Ile Pro Pro Asp
                100                 105                 110

Gln Gln Arg Leu Ile Phe Ala Gly Lys Gln Leu Glu Asp Gly Arg Thr
                115                 120                 125

Leu Ser Asp Tyr Asn Ile Gln Lys Glu Ser Thr Leu His Leu Val Leu
                130                 135                 140

Arg Leu Arg Gly Gly Ser
145                 150

<210> SEQ ID NO 34
<211> LENGTH: 37
<212> TYPE: DNA
<213> ORGANISM: Artificial
<220> FEATURE:
<223> OTHER INFORMATION: Synthetic; TripUB GrB fw primer

<400> SEQUENCE: 34
gtggatccat cgagcctgac tctcctggta ccgagcc                              37
```

<210> SEQ ID NO 35
<211> LENGTH: 38
<212> TYPE: DNA
<213> ORGANISM: Artificial
<220> FEATURE:
<223> OTHER INFORMATION: Synthetic; TripUB GrB rev primer

<400> SEQUENCE: 35
ggtaccagga gagtcaggct cgatggatcc actaccac                                    38

<210> SEQ ID NO 36
<211> LENGTH: 34
<212> TYPE: DNA
<213> ORGANISM: Artificial
<220> FEATURE:
<223> OTHER INFORMATION: Synthetic; RAP GrB fw primer

<400> SEQUENCE: 36
cggatccatc gagcctgact actcgcggga gaag                                        34

<210> SEQ ID NO 37
<211> LENGTH: 34
<212> TYPE: DNA
<213> ORGANISM: Artificial
<220> FEATURE:
<223> OTHER INFORMATION: Synthetic; RAP GrB rev primer

<400> SEQUENCE: 37
cccgcgagta gtcaggctcg atggatccgt gatg                                        34

<210> SEQ ID NO 38
<211> LENGTH: 42
<212> TYPE: DNA
<213> ORGANISM: Artificial
<220> FEATURE:
<223> OTHER INFORMATION: Synthetic; Mut-GrB fw

<400> SEQUENCE: 38
cgtggtggat ccatcgagcc ggacggtgga gatgaacccc cc                               42

<210> SEQ ID NO 39
<211> LENGTH: 42
<212> TYPE: DNA
<213> ORGANISM: Artificial
<220> FEATURE:
<223> OTHER INFORMATION: Synthetic;  Mut-GrB rw

<400> SEQUENCE: 39 gggggggttca tctccaccgt ccggctcgat ggatccacca cg                              42

<210> SEQ ID NO 40
<211> LENGTH: 33
<212> TYPE: DNA
<213> ORGANISM: Artificial
<220> FEATURE:
<223> OTHER INFORMATION: Synthetic; TN GrB fw primer

<400> SEQUENCE: 40
ggatccatcg agcctgacgg cgagccacca acc                                         33

<210> SEQ ID NO 41
<211> LENGTH: 33
<212> TYPE: DNA
<213> ORGANISM: Artificial
<220> FEATURE:
<223> OTHER INFORMATION: Synthetic; TN GrB rev primer

```
<400> SEQUENCE: 41
ggctcgccgt caggctcgat ggatccgtga tgg                           33

<210> SEQ ID NO 42
<211> LENGTH: 33
<212> TYPE: DNA
<213> ORGANISM: Artificial
<220> FEATURE:
<223> OTHER INFORMATION: Synthetic; PC7TripUB GR-AD fw

<400> SEQUENCE: 42
ggatccatcc aggcagactc tcctggtacc gag                           33

<210> SEQ ID NO 43
<211> LENGTH: 34
<212> TYPE: DNA
<213> ORGANISM: Artificial
<220> FEATURE:
<223> OTHER INFORMATION: Synthetic; PC7TripUB GR-AD rev

<400> SEQUENCE: 43
gtaccaggag agtctgcctg gatggatcca ctac                          34

<210> SEQ ID NO 44
<211> LENGTH: 37
<212> TYPE: DNA
<213> ORGANISM: Artificial
<220> FEATURE:
<223> OTHER INFORMATION: Synthetic; PC7TripUB P-G fw

<400> SEQUENCE: 44
ggatccatcc aggcagactc tggtggtacc gagccac                       37

<210> SEQ ID NO 45
<211> LENGTH: 38
<212> TYPE: DNA
<213> ORGANISM: Artificial
<220> FEATURE:
<223> OTHER INFORMATION: Synthetic; PC7TripUB P-G rev

<400> SEQUENCE: 45
ctcggtacca ccagagtctg cctggatgga tccactac                      38

<210> SEQ ID NO 46
<211> LENGTH: 34
<212> TYPE: DNA
<213> ORGANISM: Artificial
<220> FEATURE:
<223> OTHER INFORMATION: Synthetic; DNATrip IE-VG fw

<400> SEQUENCE: 46
gtagtggatc agtcgggcct gactctcctg gtac                          34

<210> SEQ ID NO 47
<211> LENGTH: 34
<212> TYPE: DNA
<213> ORGANISM: Artificial
<220> FEATURE:
<223> OTHER INFORMATION: Synthetic; DNATrip IE-VG rev

<400> SEQUENCE: 47
gagagtcagg cccgactgat ccactaccac tacc                          34

<210> SEQ ID NO 48
<211> LENGTH: 31
```

```
<212> TYPE: DNA
<213> ORGANISM: Artificial
<220> FEATURE:
<223> OTHER INFORMATION: Synthetic; DNATrip SP-FG fw

<400> SEQUENCE: 48
ggcctgactt tggtggtacc gagccaccaa c                              31

<210> SEQ ID NO 49
<211> LENGTH: 31
<212> TYPE: DNA
<213> ORGANISM: Artificial
<220> FEATURE:
<223> OTHER INFORMATION: Synthetic; DNATrip SP-FG rev

<400> SEQUENCE: 49
ggctcggtac caccaaagtc aggcccgact g                              31

<210> SEQ ID NO 50
<211> LENGTH: 52
<212> TYPE: DNA
<213> ORGANISM: Artificial
<220> FEATURE:
<223> OTHER INFORMATION: Synthetic; Trip IEPD-TQ

<400> SEQUENCE: 50
gggaaaggat ccatcgagcc tgacacccag aagcccaaga agattgtaaa tg        52

<210> SEQ ID NO 51
<211> LENGTH: 54
<212> TYPE: DNA
<213> ORGANISM: Artificial
<220> FEATURE:
<223> OTHER INFORMATION: Synthetic; Trip IEPD-IV

<400> SEQUENCE: 51
gggaaaggat ccatcgagcc tgacattgta aatgccaaga agatgttgt gaac       54

<210> SEQ ID NO 52
<211> LENGTH: 39
<212> TYPE: DNA
<213> ORGANISM: Artificial
<220> FEATURE:
<223> OTHER INFORMATION: Synthetic; UB3

<400> SEQUENCE: 52
cgcaagcttg catgcttagg atccaccacg aagtctcaa                      39

<210> SEQ ID NO 53
<211> LENGTH: 29
<212> TYPE: DNA
<213> ORGANISM: Artificial
<220> FEATURE:
<223> OTHER INFORMATION: Synthetic;  TripUB EP fw

<400> SEQUENCE: 53
cgagcctgac gagcctggta ccgagccac                                 29

<210> SEQ ID NO 54
<211> LENGTH: 30
<212> TYPE: DNA
<213> ORGANISM: Artificial
<220> FEATURE:
<223> OTHER INFORMATION: Synthetic; TripUB EP rev

<400> SEQUENCE: 54
cggtaccagg ctcgtcaggc tcgatggatc                                30
```

<210> SEQ ID NO 55
<211> LENGTH: 29
<212> TYPE: DNA
<213> ORGANISM: Artificial
<220> FEATURE:
<223> OTHER INFORMATION: Synthetic; TripUB EG fw

<400> SEQUENCE: 55
cctgacgagg gtggtaccga gccaccaac                                29

<210> SEQ ID NO 56
<211> LENGTH: 29
<212> TYPE: DNA
<213> ORGANISM: Artificial
<220> FEATURE:
<223> OTHER INFORMATION: Synthetic; TripUB EG rev

<400> SEQUENCE: 56
gctcggtacc accctcgtca ggctcgatg                                29

<210> SEQ ID NO 57
<211> LENGTH: 227
<212> TYPE: PRT
<213> ORGANISM: Artificial
<220> FEATURE:
<223> OTHER INFORMATION: Synthetic; GrB variant C228F

<400> SEQUENCE: 57

Ile Ile Gly Gly His Glu Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Gln Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Pro Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Phe Thr Lys Val Ser Ser Phe Val His Trp Ile Lys Lys Thr Met
    210                 215                 220

Lys Arg Tyr
225

```
<210> SEQ ID NO 58
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is one or more amino acid (s)
<220> FEATURE:
<221> NAME/KEY: MISC_FEATURE
<222> LOCATION: (3)..(3)
<223> OTHER INFORMATION: Xaa is any amino acid

<400> SEQUENCE: 58

Xaa Pro Xaa Pro
1

<210> SEQ ID NO 59
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is either Ile or Val
<220> FEATURE:
<221> NAME/KEY: MISC_FEATURE
<222> LOCATION: (2)..(2)
<223> OTHER INFORMATION: Xaa is Glu or Gln or Met
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Asp

<400> SEQUENCE: 59

Xaa Xaa Xaa Xaa
1

<210> SEQ ID NO 60
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ile or Val
<220> FEATURE:
<221> NAME/KEY: MISC_FEATURE
<222> LOCATION: (2)..(2)
<223> OTHER INFORMATION: Xaa is Glu or Gln or Met
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Asp
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
```

<223> OTHER INFORMATION: Xaa is any amino acid

<400> SEQUENCE: 60

Xaa Xaa Xaa Xaa Xaa Xaa
1               5

<210> SEQ ID NO 61
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 61

Ile Cys Pro Asp
1

<210> SEQ ID NO 62
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 62

Ile Glu Ala Asp
1

<210> SEQ ID NO 63
<211> LENGTH: 4
<212> TYPE: PRT
<213> ORGANISM: Artificial
<220> FEATURE:
<223> OTHER INFORMATION: Synthetic; Grb protease recoginition site

<400> SEQUENCE: 63

Ile Glu Pro Asp
1

<210> SEQ ID NO 64
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 64

Ile Glu Thr Asp
1

<210> SEQ ID NO 65
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 65

Ile Gln Ala Asp
1

<210> SEQ ID NO 66
<211> LENGTH: 4
<212> TYPE: PRT
<213> ORGANISM: Artificial
<220> FEATURE:
<223> OTHER INFORMATION: Synthetic; GrB protease recognition site

```
<400> SEQUENCE: 66

Ile Ser Ala Asp
1

<210> SEQ ID NO 67
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 67

Ile Ser Ser Asp
1

<210> SEQ ID NO 68
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 68

Ile Thr Pro Asp
1

<210> SEQ ID NO 69
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 69

Val Ala Pro Asp
1

<210> SEQ ID NO 70
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 70

Val Ala Thr Asp
1

<210> SEQ ID NO 71
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 71

Val Cys Thr Asp
1

<210> SEQ ID NO 72
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 72
```

```
Val Asp Pro Asp
1

<210> SEQ ID NO 73
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 73

Val Asp Ser Asp
1

<210> SEQ ID NO 74
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 74

Val Glu Lys Asp
1

<210> SEQ ID NO 75
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 75

Val Glu Gln Asp
1

<210> SEQ ID NO 76
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 76

Val Gly Pro Asp
1

<210> SEQ ID NO 77
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 77

Val Glu Ile Asp
1

<210> SEQ ID NO 78
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 78

Val Arg Pro Asp
1
```

```
<210> SEQ ID NO 79
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 79

Val Thr Pro Asp
1

<210> SEQ ID NO 80
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 80

Leu Glu Glu Asp
1

<210> SEQ ID NO 81
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 81

Leu Glu Ile Asp
1

<210> SEQ ID NO 82
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 82

Leu Gly Asn Asp
1

<210> SEQ ID NO 83
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 83

Leu Gly Pro Asp
1

<210> SEQ ID NO 84
<211> LENGTH: 4
<212> TYPE: PRT
<213> ORGANISM: Artificial
<220> FEATURE:
<223> OTHER INFORMATION: Synthetic; GrB protease recognition site

<400> SEQUENCE: 84

Ala Gln Pro Asp
1
```

```
<210> SEQ ID NO 85
<211> LENGTH: 6
<212> TYPE: PRT
<213> ORGANISM: Artificial
<220> FEATURE:
<223> OTHER INFORMATION: Synthetic

<400> SEQUENCE: 85

Ile Glu Pro Asp Ser Pro
1               5

<210> SEQ ID NO 86
<211> LENGTH: 6
<212> TYPE: PRT
<213> ORGANISM: Artificial
<220> FEATURE:
<223> OTHER INFORMATION: Synthetic

<400> SEQUENCE: 86

Ile Glu Pro Asp Glu Gly
1               5

<210> SEQ ID NO 87
<211> LENGTH: 6
<212> TYPE: PRT
<213> ORGANISM: Artificial
<220> FEATURE:
<223> OTHER INFORMATION: Synthetic

<400> SEQUENCE: 87

Ile Glu Pro Asp Glu Pro
1               5

<210> SEQ ID NO 88
<211> LENGTH: 7
<212> TYPE: PRT
<213> ORGANISM: Artificial
<220> FEATURE:
<223> OTHER INFORMATION: Synthetic; sequence containing blood clotting
      fact Xa recognition sequence

<400> SEQUENCE: 88

Met Gly Ser Ile Glu Gly Arg
1               5

<210> SEQ ID NO 89
<211> LENGTH: 4
<212> TYPE: PRT
<213> ORGANISM: Artificial
<220> FEATURE:
<223> OTHER INFORMATION: Synthetic

<400> SEQUENCE: 89

Ile Glu Gly Arg
1

<210> SEQ ID NO 90
<211> LENGTH: 4
<212> TYPE: PRT
<213> ORGANISM: Artificial
<220> FEATURE:
<223> OTHER INFORMATION: Synthetic

<400> SEQUENCE: 90

Ile Gln Gly Arg
1

<210> SEQ ID NO 91
```

-continued

```
<211> LENGTH: 6
<212> TYPE: PRT
<213> ORGANISM: Artificial
<220> FEATURE:
<223> OTHER INFORMATION: Synthetic

<400> SEQUENCE: 91

Ile Gln Ala Asp Ser Pro
1               5

<210> SEQ ID NO 92
<211> LENGTH: 6
<212> TYPE: PRT
<213> ORGANISM: Artificial
<220> FEATURE:
<223> OTHER INFORMATION: Synthetic

<400> SEQUENCE: 92

Ile Gln Ala Asp Ser Gly
1               5

<210> SEQ ID NO 93
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ile or Val
<220> FEATURE:
<221> NAME/KEY: MISC_FEATURE
<222> LOCATION: (2)..(2)
<223> OTHER INFORMATION: Xaa is Glu or Gln or Met
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Asp
<220> FEATURE:
<221> NAME/KEY: MISC_FEATURE
<222> LOCATION: (5)..(8)
<223> OTHER INFORMATION: Xaa is any amino acid

<400> SEQUENCE: 93

Xaa Xaa Xaa Xaa Xaa Xaa Xaa Xaa
1               5
```

CLEAVAGE OF FUSION PROTEINS USING GRANZYME B PROTEASE

CROSS-REFERENCE TO RELATED APPLICATIONS

This application is a national stage application of International Application No. PCT/DK2004/000282, filed 23 Apr. 2004, which claims benefit of Denmark Patent Application No. PA 2003 00616, filed 23 Apr. 2003 and U.S. Provisional Patent Application No. 60/464,663, filed 23 Apr. 2003. The entire contents of all the above-identified applications are incorporated herein by reference.

FIELD OF THE INVENTION

The present invention relates to a method for the preparation of a polypeptide of interest in authentic form by enzymatic cleavage of recombinantly produced fusion proteins by the use of Granzyme B protease. Furthermore, the invention pertains to fusion proteins comprising a Granzyme B cleavage site and to a human Granzyme B variant.

BACKGROUND OF THE INVENTION AND PRIOR ART

The production and purification of recombinant polypeptides such as pharmaceutical proteins in a highly purified and well-characterized form, has become a major task within the area of protein engineering in general, and in the pharmaceutical industry in particular.

The preparation of such recombinant polypeptides relies frequently on techniques which involve the production of the polypeptides as fusion proteins or hybrid proteins, wherein a protein or polypeptide of interest is fused to a carrier or a fusion partner such as a polypeptide or a protein.

The presence of a fusion partner or carrier which is fused to the polypeptide of interest has the advantages that it may render the fusion protein more resistant to proteolytic degradation, may facilitate enhanced expression and secretion, improve solubility and allow for subsequent affinity purification of the fusion protein. Also by fusion protein expression, potentially bio-hazardous materials, such as peptide hormones, may be produced in an inactive form which can then be activated subsequently in vitro by cleaving off the fusion partner.

However, such fusion proteins themselves are not normally suitable as end products as the fusion partner e.g. may affect the biological activity or stability of the polypeptide of interest and, if the protein is to be used clinically, may cause antigenicity problems. Therefore it is necessary to cleave the fusion protein to release the polypeptide of interest.

In principle this can be achieved by chemical or biochemical methods such as enzymatic cleavage. However, it is important that the cleavage is highly specific and only takes place in a cleavage sequence between the polypeptide of interest and the fusion partner, i.e. the junction region, but preferably not within the polypeptide of interest itself, as this may e.g. severely affect the bioactivity of the polypeptide of interest. Such methods employ agents that act by hydrolysis of peptide bonds and the specificity of the cleavage agent is determined by the identity of the amino acid residue at or near the peptide bond which is cleaved.

Biochemical methods for cleavage of fusion proteins are based on the use of proteases (proteolytic enzymes). However, enzymatic cleavage of fusion proteins is limited in that the amino acid(s) which are specific for the cleavage site can at the same time also occur in the polypeptide of interest itself. Therefore, enzymes are particularly suitable which, in order to cleave, not only recognises one amino acid but rather a sequence of amino acids, since the probability that a particular amino acid sequence is present once again in the polypeptide of interest in addition to the cleavage site between the polypeptide of interest and the fusion partner is less the larger the number of amino acids necessary for the recognition and cleavage of the cleavage sequence.

Up till now, a number of proteases have been used for enzymatic cleavage of fusion proteins by contacting the fusion protein with a protease under appropriate conditions.

WO 03/010204 relates to a process for separating a polypeptide of interest from a fusion protein by the use of ubiquitin cleavage enzyme, which according to this document is an enzyme that cleaves a peptide bond next to the amino acid sequence RGG at the C-terminus of proteins such as ubiquitin.

U.S. Pat. No. 6,010,883 disclose a method wherein blood clotting factor Xa (EC 3.4.21.6; a S1 serine-type peptidase formed from the proenzyme factor X by limited proteolysis) is used for cleaving off a fusion partner from a fusion protein. This protease specifically cleaves after the amino acid sequence X-Y-Gly-Arg, wherein X is Ile, Leu, Pro or Ala, and Y is Glu, Asp, Gln or Asn. Factor Xa preferably cuts after the cleavage sequence Ile-Glu-Gly-Arg.

Other prior art enzymes which have been suggested and used in methods for specific cleavage of fusion proteins include tobacco etch virus NIa proteinase, collagenase, enterokinase, subtilisin and thrombin.

However, several problems may be encountered when using proteolytic cleavage in fusion protein systems. One major problem is the occurrence of non-specific proteolytic attack of the fusion protein which results in cleavage at several locations and consequently product loss and generation of contaminating fragments. Also problems with inefficient or incomplete cleavage of the fusion protein frequently occur with the presently known enzymes. Such inefficient cleavage reduces the yield and may also introduce heterogeneity to the purified protein resulting in the recovery of only a small fraction of the desired protein.

A further problem that is associated with several of the presently applied enzymes for fusion protein cleavage is that spurious or extraneous amino acids are frequently attached to the cleaved polypeptide product (the polypeptide of interest). These amino acids are typically present when a linker is cleaved, and the unrelated amino acid residues may have an effect on the properties of the resulting polypeptide of interest. This may be critical for proteins produced for human therapeutics. Therefore, it is highly desirable to be able to produce pure authentic polypeptides free of extraneous amino acid short sequences or residues.

The problem with extraneous amino acids remaining on the polypeptide of interest after cleavage is illustrated in U.S. Pat. No. 4,543,329 which describes a process for selectively cleaving a fusion protein by the use of collagenase. However, the use of this enzyme produces a polypeptide of interest with the extraneous amino acid sequence Gly-Pro at its N-terminal. In order to obtain the polypeptide of interest in authentic form, these extraneous amino acids (Gly and Pro) must subsequently be removed in a further reaction step by the use of one or more different amino peptidases (such as aminoacylproline amino peptidase and proline amino peptidase).

The problem is also illustrated in U.S. Pat. No. 5,427,927 which describes a process for sequence specific cleavage of fusion proteins by the use of IgA protease, wherein a IgA protease recognition site is inserted in the junction region of a fusion protein which is subsequently cleaved with IgA protease. The recognition site for the IgA protease is the amino acid sequence Y-Pro↓X-Pro (SEQ ID NO: 58), in which X can be any amino acid, Y can be one or several arbitrary amino acids, and ↓ denotes the cleavage site. However, the proteins of interest which are formed after cleavage by IgA protease, are characterised by having an X-Pro extraneous amino sequence at its N-terminal, i.e. the resulting polypeptide of interest is not in its native or authentic form.

Presently, the most widely used proteolytic enzymes for fusion protein cleavage are the serine proteases factor Xa and thrombin. However, both enzymes are known to perform non-specific cleavage of fusion proteins. In addition, factor Xa has to be isolated from bovine serum and as a consequence when it is used to cleave proteins for therapeutic applications an extensive purification and analysis is necessary afterwards in order to detect pathogenic factors such as viruses and prions which may be present (e.g. prions causing bovine spongiform encephalopathy). Furthermore, these enzymes are rather expensive.

In view of these prior art shortcomings and drawbacks, it is therefore an object of the present invention to provide an improved method for enzymatic cleavage of fusion proteins.

It has been found by the present inventors, that the above technical problems may be overcome by using Granzyme B protease (EC 3.4.21.79) for enzymatic cleavage of fusion proteins. Thus, it has surprisingly been found that Granzyme B protease allows for highly efficient cleavage of fusion proteins having a Granzyme B protease cleavage site with a high degree of cleavage specificity. In particular Granzyme B protease has proven to perform more specific fusion protein cleavage than the presently and widely used protease factor Xa. It has furthermore been found that Granzyme B cleavage of fusion proteins that contain a Granzyme B recognition sequence positioned between an N-terminal fusion partner and a C-terminal polypeptide of interest, wherein the cleavage site is adjacent to the polypeptide of interest, results in a polypeptide of interest that have no extraneous amino acids derived from the cleavage site, i.e. a polypeptide in authentic form. Thus, recombinant proteins of interest with native amino acid sequence may be produced as a result of fusion protein cleavage by Granzyme B. Also, the Granzyme B protease has the advantage that it can be produced recombinantly. Finally, it has been found that by substituting the Cysteine amino acid no. 228 (chymotrypsinogen numbering) with Phenylalanine in human Granzyme B, a higher final protein recovery can be obtained when producing recombinant human Granzyme B.

SUMMARY OF THE INVENTION

Accordingly, the present invention relates in a first aspect to a method for the preparation of a polypeptide of interest in authentic form. The method comprises the steps of: (i) providing a fusion protein comprising, from its N-terminal to its C-terminal (a) a fusion partner, (b) a Granzyme B protease recognition site comprising a Granzyme B protease cleavage site, (c) a polypeptide of interest, wherein said cleavage site being adjacent to the polypeptide of interest, and (ii) contacting the fusion protein with Granzyme B protease (EC 3.4.21.79) to cleave it at the cleavage site to yield the polypeptide of interest in authentic form.

In a further aspect there is provided a fusion protein comprising, from its N-terminal to its C-terminal, (a) a fusion partner, (b) a Granzyme B protease recognition site comprising a Granzyme B protease cleavage site, and (c) a polypeptide of interest, wherein said cleavage site being adjacent to the polypeptide of interest.

There is also provided a human Granzyme B protease variant wherein the Cystein residue no. 228 (chymotrypsinogen numbering) is mutated to Phenylalanine.

In still further aspects there is provided an isolated nucleic acid sequence encoding such a fusion protein or human Granzyme B protease variant, a recombinant vector comprising the isolated nucleic acid sequence, a host cell transformed with such a vector, and a method for the production of the fusion protein or the human Granzyme B protease variant which comprises the steps of (i) providing such a recombinant vector which is operatively linked to a promotor, (ii) transforming a host cell with the recombinant vector, (iii) culturing the host cell under conditions to express the fusion protein, and (iv) optionally isolating the fusion protein or the human Granzyme B protease variant.

DETAILED DISCLOSURE OF THE INVENTION

In one aspect the present invention relates to a method for preparing a polypeptide of interest in authentic form by enzymatic cleavage of fusion proteins. Accordingly, the method comprises, as is mentioned above, a step of providing a fusion protein comprising from its N-terminal to its C-terminal, a fusion partner, a Granzyme B protease recognition site comprising a Granzyme B protease cleavage site and a polypeptide of interest, wherein the cleavage site is placed adjacent to the polypeptide of interest. The fusion protein is subsequently contacted with Granzyme B protease to cleave the fusion protein at the Granzyme B protease cleavage site to yield the polypeptide of interest in authentic form. The term "fusion protein" as used herein, refers to a polypeptide which comprises protein domains from at least two different proteins.

In accordance with the present invention there is provided a method for producing polypeptides of interest in authentic form. As used herein, the term "authentic form" refers to a polypeptide which comprises the amino acid sequence thereof without any additional amino acid residues. As described above, a major problem associated with several of the presently applied enzymes for fusion protein cleavage is that spurious or extraneous amino acids frequently remains attached to the cleaved polypeptide product, i.e. resulting in a polypeptide which is not in an "authentic form". Thus, in the present context the polypeptide of interest in authentic form refers to a polypeptide having the same primary amino acid sequence as that encoded by the native gene sequence coding for the polypeptide of interest, i.e. it does not contain any non-native amino acids. The term "native gene sequence" is not necessarily a gene sequence that occurs in nature, but it may also be partly or completely artificial. Likewise it will be appreciated that a polypeptide of interest in authentic form not necessarily is a polypeptide that occurs in nature, but it may also be partially or completely artificial. In contrast, a "non-authentic" polypeptide contains at least one amino acid which is not encoded for by the native gene sequence coding for the polypeptide of interest.

In accordance with the invention, the junction region between the polypeptide of interest and the fusion partner comprises a Granzyme B protease recognition site which has a Granzyme B protease cleavage site. Such a recognition site refers to a defined amino acid sequence that allows Granzyme B to recognize and to cleave the junction region between the fusion partner and the polypeptide of interest. The cleavage site is thus to be understood as the site between two amino acids of an amino acid sequence at which the cleavage of the fusion protein takes place. The junction region may be in the form of a linker sequence of any suitable length which is not part of the polypeptide of interest. However, in order to obtain the polypeptide of interest in authentic form, the Granzyme B cleavage site is positioned adjacent to the N-terminus of the polypeptide of interest in order to allow for specific cleavage of the fusion protein at its N-terminus without resulting in spurious or extraneous amino acids remaining attached to the resulting polypeptide of interest. Hence, the term "adjacent to" imply that the Granzyme B recognition sequence, which in some embodiments may be preceded by or be a part of a linker sequence, is positioned such that the Granzyme B cleavage site is flanking the N-terminus of the polypeptide of interest.

Granzymes are granule-stored serine proteases that are implicated in T cell and natural killer cell-mediated cytotoxic defence reactions after target cell recognition. The principal function of granzymes is to induce the death of virus-infected and other potentially harmful cells. Granzyme B is one type of granzymes, and upon target cell contact it is directionally exocytosed and enters target cells assisted by perforin (a cytolytic protein expressed by cytotoxic T cells and natural killer cells). Granzyme B processes and activates various pro-caspases, thereby inducing apoptosis in the target cell. In accordance with the invention, the term "Granzyme B protease" (also referred to herein as GrB) includes enzymes which are or may be classified under the Enzyme Commission number EC 3.4.21.79 in Enzyme nomenclature database available on the website of Expasy, Release 34, February 2004. Thus, in accordance with the invention any suitable Granzyme B protease may be used including human Granzyme B protease, mouse Granzyme B protease and rat Granzyme B protease. It is generally preferred to use human Granzyme B, when the method in accordance with invention is used for the preparation of human therapeutic protein products. Human Granzyme B protease occurs in most human tissues where its biological function is well known. Therefore, the presence of trace amounts of residual Granzyme B protease in the final therapeutic protein product exhibit a minimal risk for the patient to whom the therapeutic protein product is administered. Thus, it is known that if active Granzyme B protease is injected into the human blood stream it is swiftly trapped by alpha-2-macroglobulin and the complex is cleared via the LRP scavenging receptor. Granzyme B protease is also known under the alternative name "Cytotoxic t-lymphocyte proteinase 2".

Granzyme B protease is known to have a preference for cleaving after aspartate residues (D), and Granzyme B is the only mammalian serine protease known to have this P1-proteolytic specificity. Hence, in accordance with the invention it is contemplated that the Granzyme B cleavage site in useful embodiments at least comprises an aspartate residue at the P1 position located N-terminally to the cleavage site. Some of the presently known Granzyme B protease recognition sites are disclosed in Harris et al (1998). Thus, in useful embodiments, the recognition site has an amino acid sequence of the general formula: P4 P3 P2 P1↓ (SEQ ID NO: 59) located N-terminally to the cleavage site, wherein P4 preferably is amino acid I or V, P3 preferably is amino acid E, Q or M, P2 is X, where X denotes any amino acid, P1 preferably is amino acid D, and ↓ is the cleavage site for the Granzyme B protease.

It was found by the present inventors, that Granzyme B protease is capable of cleaving off polypeptides of interest from a fusion protein, without leaving any non-native amino acids on the polypeptide of interest. In particular it was surprisingly found that Granzyme B would recognise and cleave off polypeptides from a fusion protein after the P1 position without any strict requirements for specific amino acid residues at the P1'-P4' positions, i.e. the amino acid positions following the cleavage site. This is contrary to the findings in the prior art. In e.g. Sun et al. (2001) it is concluded that the P1'-P4' residues of Granzyme B substrates are important for substrate binding, and that highest affinity for the substrate is observed when an acidic P4' residue is present (i.e. either aspartate or glutamic acid). Furthermore, Harris et al. (1998) concluded that Granzyme B has a strong preference for glycine residue at the P2' position. Despite these prior art findings, it has now been established that Granzyme B protease may be generally used for cleaving off polypeptides of interest from fusion proteins, without the need for specific amino acid residues at the P1'-P4' positions.

As mentioned above, a further particular advantage of the present invention is the finding that Granzyme B protease allows for highly efficient cleavage of fusion proteins having a Granzyme B protease cleavage site positioned N-terminally to the polypeptide of interest with a high degree of cleavage specificity. In particular it has been found that Granzyme B protease perform more specific fusion protein cleavage than the presently and widely used protease for fusion protein cleavage, namely factor Xa. Thus, as will be apparent from the below examples, it was found that when five different fusion proteins previously made as factor Xa cleavable fusion proteins, were cleaved by Granzyme B protease, it resulted in a cleavage performance that was as specific as or even more specific than that found with factor Xa. This may e.g. be seen from Example 8 and the accompanying FIG. 11 illustrating an extended time course PAGE analysis of the digestion of the fusion proteins H6-IEGR-RAP and H6-IEPD-RAP (SEQ ID NO: 23) with factor Xa and Granzyme B, respectively. It is clearly seen from this experiment that after 30 min. there was an essentially complete cleavage of the fusion proteins with both proteases. However, more breakdown products were produced by the use of factor Xa as compared to Granzyme B. This clearly shows that Granzyme B is highly specific, and even more specific than the widely used protease factor Xa. The high versatility and great flexibility of Granzyme B is further substantiated herein by the findings that Granzyme B is both capable of cleaving off relatively short N-terminal tags such as a hexa-His tail from a polypeptide of interest, and to cleave between a fusion partner and a polypeptide of interest which are very closely connected by a short linker sequence.

Although not necessary, it may in certain embodiments be advantageous to select the polypeptide of interest such that the polypeptide of interest, when it is a part of the fusion protein, N-terminally comprises the amino acids P1' and P2' resulting in the general Granzyme B recognition site formula P4 P3 P2 P1↓P2' (SEQ ID NO: 60) wherein P1' is X, where X denotes any amino, and P2' is G. Although Granzyme B protease has no strict amino acid selectivity for the P1' position, there is a general preference for large hydrophobic amino acids at this position including Trp (T), Leu (L), Phe (F) and Ile (I). Thus, in one useful embodiment the amino acid at position P1' is selected from T, L, F and I. It may in certain embodiments by advantageous not to include Pro (P) at the P2' position. It may in a further aspect of the invention be advantageous that the polypeptide of interest is selected such that it, when being part of the fusion protein, N-terminally comprises an acidic amino acid at the P4' position, such as D or E.

In the present context the terms "amino acid" and "amino acid residues" refer to all naturally occurring L-alpha-amino acids. This definition is meant to include norleucine, ornithine, and homocysteine. The amino acids are identified by either the three-letter or single-letter designations:
Asp, D: aspartic acid Ile, I: isoleucine
Thr, T: threonine Leu, L: leucine
Ser, S: serine Tyr, Y: tyrosine
Glu, E: glutamic acid Phe, F: phenylalanine
Pro, P: proline His, H: histidine
Gly, G: glycine Lys, K: lysine
Ala, A: alanine Arg, R: arginine
Cys, C: cysteine Trp, W: tryptophan
Val, V: valine Gln, Q: glutamine
Met, M: methionine Asn, N: asparagine
Nle, J: norleucine Orn, O: ornithine
Hcy, U: homocysteine Xxx, X: any L-alpha-amino acid.

In further useful embodiments, the Granzyme B protease recognition site has an amino acid sequence which is selected from ICPD↓ (SEQ ID NO: 61), IEAD↓ (SEQ ID NO: 62), IEPD↓ (SEQ ID NO: 63), IETD↓ (SEQ ID NO: 64), IQAD↓ (SEQ ID NO: 65), ISAD↓ (SEQ ID NO: 66), ISSD↓ (SEQ ID NO: 67), ITPD↓ (SEQ ID NO: 68), VAPD↓ (SEQ ID NO: 69), VATD↓ (SEQ ID NO: 70), VCTD↓ (SEQ ID NO: 71), VDPD↓ (SEQ ID NO: 72), VDSD↓ SEQ ID NO: 73), VEKD↓ SEQ ID NO: 74), VEQD↓ (SEQ ID NO: 75), VGPD↓ SEQ ID NO: 76), VEID↓ (SEQ ID NO: 77), VRPD↓ (SEQ ID NO: 78), VTPD↓ (SEQ ID NO: 79), LEED↓ SEQ ID NO: 80), LEID↓ (SEQ ID NO: 81), LGND↓ (SEQ ID NO: 82), LGPD↓ (SEQ ID NO: 83), AQPD↓ (SEQ ID NO: 84), where ↓ is the cleavage site for Granzyme B. These recognition and cleavage sites have previously been described by Casciola-Rosen et al. (1999).

In accordance with the invention the terms "polypeptide of interest" or "desired polypeptide" refer to the polypeptide whose expression is desired within the fusion protein. As used herein, the term "polypeptide" should not necessarily indicate a limit on the size of the desired polypeptide of interest. Thus, this term is to be interpreted in its broadest sense, and hence includes peptides on the order of up to 50 or more amino acids, including oligopeptides such as di-, tri, tetra-, penta-, and hexa-peptides, polypeptides and proteins. The polypeptide of interest may by an intermediate product or a final product which can for example be used in the field of medicine, in research, in environmental protection, or in industrial processes or products. As previously described, in the fusion protein the polypeptide of interest is joined or fused with another protein or protein domain, the fusion partner, to allow for e.g. enhanced stability of the polypeptide of interest and ease of purification of the fusion protein. In useful embodiments the polypeptide of interest is a protein such as a secreted protein. Secreted proteins have various industrial applications, including as pharmaceuticals, and diagnostics. Most protein drugs available at present, such as thrombolytic agents, interferons, interleukins, erythropoietins, colony stimulating factors, and various other cytokines, are secreted proteins. In useful embodiments the polypeptide of interest is a polypeptide hormone such as somatotrophin, glucagon, insulin or interferon, a single chain antibody variable region fragment (scfv), or an apolipoprotein such as apolipoprotein a-i (apoA-I), apolipoprotein A-II, or apolipoprotein A-IV.

In a further aspect of the invention the polypeptide of interest is an enzyme, such as Granzyme B. Thus, by providing a fusion protein in accordance with the invention and selecting Granzyme B protease as the polypeptide of interest, there is provided a self-activating Granzyme B protease which offers the possibility of providing inactive pro-Granzyme B which subsequently may be activated, in principle, by the addition of a single molecule of active Granzyme B protease. Thereby, there is provided pro-Granzyme B which is not dependent on the addition of e.g. external activator biologicals for its activation. As will be apparent from the following examples, the Granzyme B self activation was found to progress quantitatively to completion, and self activating samples of Granzyme B protease subjected to further incubation for several days were found to retain stable activity levels and produce minimal amounts of autolysis products. This clearly demonstrates that self-activating Granzyme B protease has the advantage of being highly stable to autolysis (cannibalism), as shown in Example 5 and FIG. 3.

The fusion partner may, in accordance with the invention, be of any suitable kind provided that it is a peptide, oligopeptide, polypeptide or protein, including a tetra-peptide, penta-peptide and a hexa-peptide. It may be selected such that it renders the fusion protein more resistant to proteolytic degradation, facilitate enhanced expression and secretion of the fusion protein, improve solubility, and allow for subsequent affinity purification of the fusion protein.

The fusion protein of the present invention may in useful embodiments comprise a fusion partner which is an affinity-tag. Such an affinity-tag may e.g. be an affinity domain which permits the purification of the fusion protein on an affinity resin. The affinity-tag may also be a polyhistidine-tag including hexahis-tag, a polyarginine-tag, a FLAG-tag, a Strep-tag, a c-myc-tag, a S-tag, a calmodulin-binding peptide, a cellulose-binding peptide, a chitin-binding domain, a glutathione S-transferase-tag, or a maltose binding protein.

As mentioned above, any suitable Granzyme B protease may be used in accordance with the invention including human Granzyme B protease, mouse Granzyme B protease and rat Granzyme B protease. However, as will be apparent from the following Examples, it was found that by substituting the Cystein residue no. 228 (chymotrypsinogen numbering) with Phenylalanine in human Granzyme B protease, there is provided a human Granzyme B protease variant which results in a higher final protein yield when producing human Granzyme B, even without affecting the cleavage specificity or activity of the resulting Granzyme B to any noticeable degree. This finding is contrary to what would have been expected, as the amino acid Phenylalanine (aromatic amino acid) is chemically very different from Cysteine (hydrophilic amino acid) and would therefore not normally be the choice for a Cysteine substitution. Thus, in a presently preferred embodiment the Granzyme B protease according to the invention is a human Granzyme B protease variant wherein the Cystein residue no. 228 (chymotrypsinogen numbering) is mutated to Phenylalanine. It will be appreciated that the term "human Granzyme B protease variant" also includes variants which in addition to the Cystein residue no. 228 (chymotrypsinogen numbering) mutation, have further variations in the full-length sequence of native human Granzyme B protease or in various domains, e.g. Granzyme B protease variants wherein one or more amino acid residues are added, or deleted, at the N- or C-terminus of the full-length native Granzyme B amino acid sequence. Such further variations can be made, for example, using any of the techniques and guidelines for conservative and non-conservative mutations known in the art. Variations may be a substitution, deletion or insertion of one or more codons encoding the human Granzyme B protease that results in a change in the amino acid sequence of the human Granzyme B protease as compared with the native sequence of human Granzyme B protease preferably without adversely affecting the human Granzyme B protease specificity and/or activity. Also fragments of the full-length native Granzyme B amino acid sequence, such as the activated form, having a Cystein residue no. 228 mutation is included in the meaning of "human Granzyme B protease variant". In a useful embodiment the Granzyme B protease variant is the variant shown in SEQ ID NO 57.

In general the fusion partner will typically be selected on the basis of characteristics contributing to ease isolation, most desirable being those that are readily secreted by the microorganisms producing the fusion protein. Polyhistidine sequences, glutathione S-transferase and maltose binding protein, for example, are generally preferred as there are readily available affinity columns to which they can be bound and eluted from.

The method according to the invention may in useful embodiments include a subsequent isolation step for isolating the polypeptide of interest which is formed by the enzymatic cleavage of the fusion protein. This isolation step can be performed by any suitable means known in the art for protein isolation, including the use of ion exchange, fractionation by size and affinity purification, the choice of which depending on the character of the polypeptide of interest. Thus the polypeptide of interest may for the purpose of affinity purification e.g. further comprise a C-terminally linked affinity-tag in to order to provide for isolation of the resulting polypeptide of interest using e.g. the above mentioned affinity-tag systems.

In accordance with the invention the fusion protein is contacted with Granzyme B protease to cleave the fusion protein at the Granzyme B protease cleavage site adjacent to the polypeptide of interest to yield the polypeptide of interest in authentic form. This reaction may be carried out batchwise using free Granzyme B, or it may be carried out by using Granzyme B protease in an immobilised form, e.g. via adsorption, covalent binding, entrapment or membrane confinement. Suitable carriers for immobilised Granzyme B protease include conventional carriers such as polyacrylamide, chitin, dextran, kappa carrageenan, celite and cellulose. Immobilisation of enzymes by their covalent coupling to insoluble matrices is an extensively used technique. Lysine residues are found to be the most generally useful groups for covalent bonding of enzymes to insoluble supports due to their widespread surface exposure and high reactivity. Thus, in useful embodiments the Granzyme B protease is immobilised via a lysine amino acid residue. In a further aspect the Granzyme B protease is immobilised via its C-terminus, e.g. by means of a polyhistidine-tag, including a hexa-histidine-tag. The reaction may also be conducted by using a free Granzyme B protease in combination with a membrane-type bioreactor, or using a continuous type bioreactor together with an immobilised Granzyme B protease.

As will be apparent from the following examples, it has surprisingly been found that the time required for the cleavage of free fusion proteins (i.e. not immobilised) which comprises a polyhistidine fusion partner such as hexa-histidine, may be decreased dramatically if the fusion protein is contacted with Granzyme B protease in the presence of $Ni^{2+}$ ions and Nitrilotriacetic Acid (NTA). It is contemplated that the main reason for this remarkable increase in cleavage speed, is that the $Ni^{2+}$ ions bind the N-terminal polyhistidine fusion partner of the fusion protein and facilitate access for the Granzyme B protease to the cleavage site. Additionally it is also considered that the addition of NTA will shield the $Ni^{2+}$ ions in solution in a similar fashion as on a $Ni^{2+}$-NTA agarose column, and thereby avoid precipitation of both the fusion protein and the resulting protein. When performing such a cleavage process, it is generally preferred that the concentration of $Ni^{2+}$ is in the range of 1-20 mM, and the concentration of NTA is in the range of 1-20 mM. Furthermore, the temperature is preferably in the range of 15-50° C., including the range of 20-45° C. In a preferred embodiment, the temperature is in the range of 20-30° C., such as about 23° C. In another slightly less preferred embodiment, the temperature is in the range of 30-45° C., such as about 37° C. The optimal temperature range, though, must be determined for each fusion protein, since it depends in part on the stability of the fusion protein at the different temperatures.

In accordance with the invention there is as already described above, also provided a fusion protein comprising, from its N-terminal to its C-terminal, (a) a fusion partner, (b) a Granzyme B protease recognition site comprising a Granzyme B protease cleavage site, and (c) a polypeptide of interest, wherein the cleavage site being adjacent to the polypeptide of interest. In useful embodiments, the polypeptide of interest is Granzyme B, which thereby provides for a self-activating Granzyme B protease. In particular there is provided self-activating human pro-Granzyme B fusion proteins comprising from the N-terminal to the C-terminal, a seven amino acid residue pro-sequence having a Granzyme B recognition site and cleavage site followed by the amino acid sequence for activated human Granzyme B, and finally a hexa-Histidine tag (H6) fused to the C-terminal of the Granzyme B. Thus, the Granzyme B cleavage site is located adjacent to the Ile16 (chymotrysinogen numbering) of the amino acid sequence for activated Granzyme B. More particular there is provided the human self-activating Granzyme B fusion proteins pro-IEPD-GrB-H6 (SEQ ID NO 2) and pro-IEAD-GrB-H6 (SEQ ID NO 3). As also previously described, it was found to be advantageous, to substitute the Cystein residue no. 228 (chymotrypsinogen numbering) with alanine (A), threonine (T), valine (V), or phenylalanine (F) by site-directed mutation. Thus, in further useful embodiments there is provided self-activating fusion proteins selected from the group consisting of pro-IEPD-GrB-H6 C228A (SEQ ID NO 5), pro-IEPD-GrB-H6 C228T (SEQ ID NO 6), pro-IEPD-GrB-H6 C228V (SEQ ID NO 7), and pro-IEPD-GrB-H6 C228F (SEQ ID NO 8).

The fusion protein or the Granzyme B protease variant of the present invention may be expressed in any suitable standard protein expression system by culturing a host transformed with a vector encoding the fusion protein under such conditions that the fusion protein is expressed. Preferably, the expression system is a system from which the desired fusion protein may readily be isolated and refolded in vitro. As a general matter, prokaryotic expression systems are preferred since high yields of protein can be obtained and efficient purification and refolding strategies are available. However, numerous host cells may be selected as appropriate for transformation and expression of the described fusion protein, including mammalian insect, fungal and bacterial host cells which are particularly desirable. Commonly used bacterial strains include *Bacillus* and *Escherichia*, including *E. coli*. Thus, it is well within the abilities and discretion of the skilled artisan, without undue experimentation, to choose an appropriate or favourite host and expression system. Similarly, once the primary amino acid sequence for the fusion protein of the present invention is chosen, one of ordinary skill in the art can easily design appropriate recombinant nucleic acid sequence or DNA constructs encoding the fusion proteins or the Granzyme B protease variant of the invention, taking into consideration such factors as codon biases in the chosen host, the need for secretion signal sequences in the host, the introduction of proteinase cleavage sites within the signal sequence, and the like. These recombinant DNA constructs may be inserted in-frame into any of a number of expression vectors appropriate to the chosen host. The choice of an appropriate or favourite expression vector is, again, a matter well within the ability and discretion of the skilled practitioner. Preferably, the expression vector will include a strong promoter to drive expression of the recombinant constructs.

Finally, there is provided a method for the production of a fusion protein or the Granzyme B protease variant according to invention which comprises the steps of (i) providing a recombinant vector comprising the isolated nucleic acid sequence encoding the fusion protein or the Granzyme B protease variant of the invention which is operatively linked to a promotor, (ii) transforming a host cell with this recombinant vector, (iii) culturing the host cell under conditions to express the fusion protein, and (iv) optionally isolating the fusion protein or the Granzyme B protease variant.

The invention will now be described by way of illustration in the following non-limiting examples and figures.

Description of lanes A-N:
A: Molecular weight marker
B: GrB-H6 C228F, before incubation
C: GrB-H6 C228F incubated at 4° C. for 1 day
D: GrB-H6 C228F incubated at 4° C. for 3 days
E: GrB-H6 C228F incubated at 4° C. for 6 days
F: GrB-H6 C228F incubated at 4° C. for 15 days
G: GrB-H6 C228F incubated at 23° C. for 1 day
H: GrB-H6 C228F incubated at 23° C. for 3 days
I: GrB-H6 C228F incubated at 23° C. for 6 days
J: GrB-H6 C228F incubated at 23° C. for 15 days
K: GrB-H6 C228F incubated at 37° C. for 1 day
L: GrB-H6 C228F incubated at 37° C. for 3 days
M: GrB-H6 C228F incubated at 37° C. for 6 days
N: GrB-H6 C228F incubated at 37° C. for 15 days Lane B shows the intact GrB-H6 C228F. This band of intact protease can be seen in all lanes (1). In lanes I-N another band appears (2), which must be a degradation product of the protease, possibly arisen by auto cleavage between Asp50 and Phe51 in the sequence IQDD↓FV.

Figure 3:
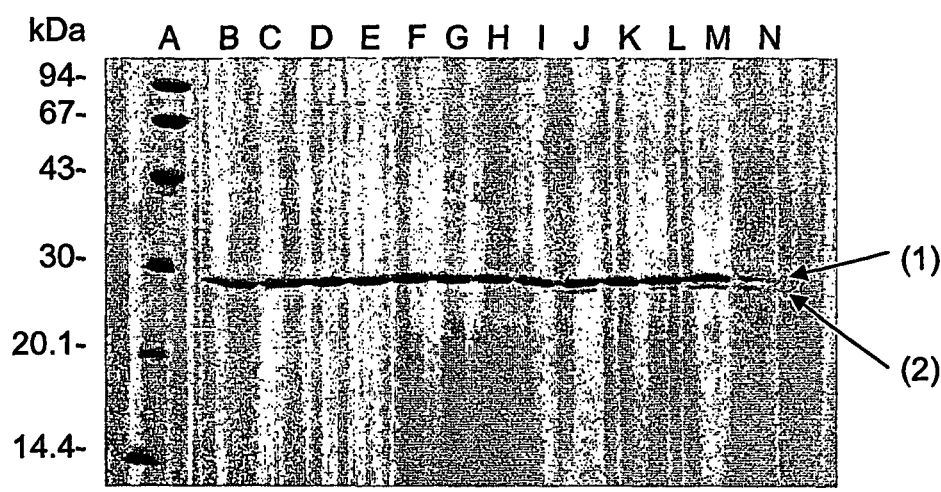
FIG. 3, panel (A) shows the SDS PAGE of samples from the incubation of GrB-H6 C228F in 100 mM HEPES pH 7.4 at 4° C., 23° C., and 37° C.
Figure 3:
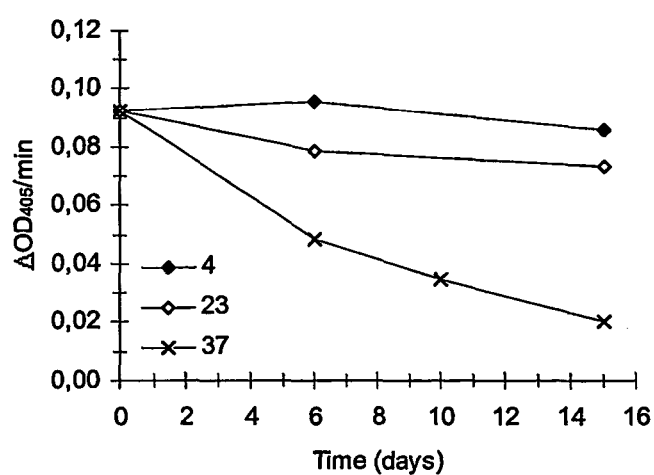

FIG. 3, Panel (B) shows the activity of the samples of GrB-H6 C228F incubated in 100 mM HEPES pH 7.4 at 4° C., 23° C., and 37° C. measured after 0, 6, (10), and 15 days. The activity was measured in 500 µl 100 mM HEPES pH 7.4 and 400 µM Ac-IEPD-pNA with 0.2 µg GrB-H6 C228F from the incubations added for each measurement.

Figure 4:
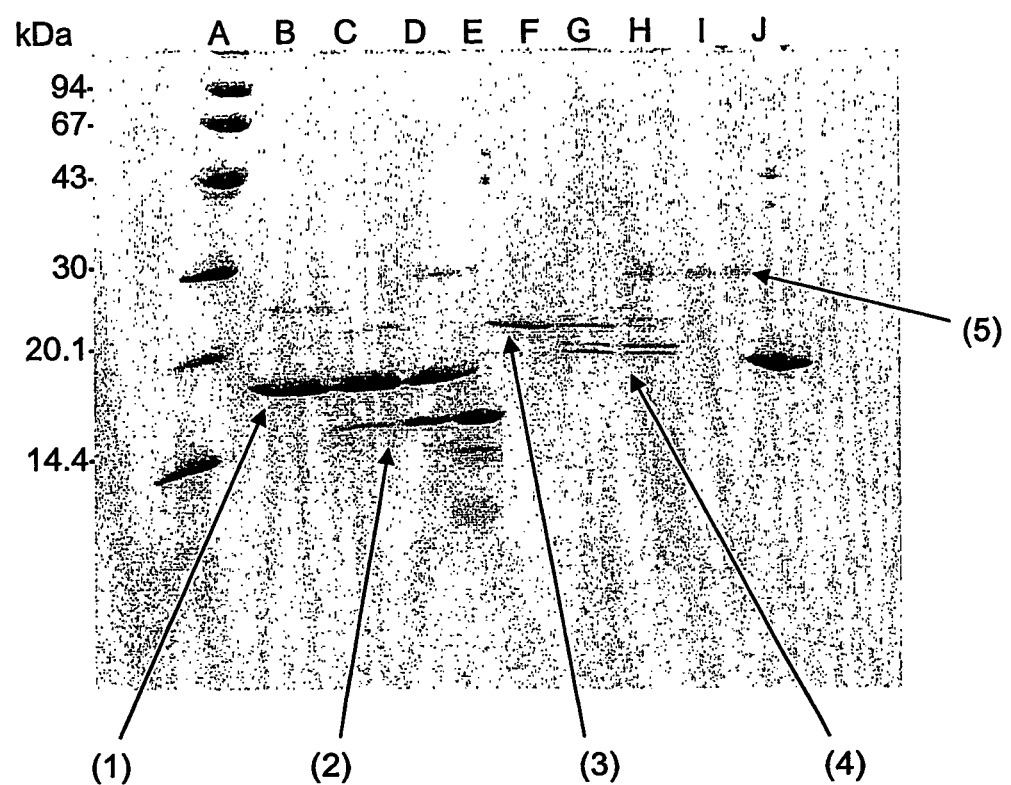

FIG. 4 shows the SDS PAGE of samples from the H6-TripUB IEPD↓SP (SEQ ID NO: 22) and H6-IEPD-TN123 (SEQ ID NO: 25) incubations after 12 hours incubation with GrB-H6.

Description of the lanes A-J:
A: Molecular weight marker
B: H6-TripUB IEPD↓SP (SEQ ID NO: 22) alone after 12 hours incubation
C: 200 µl H6-TripUB IEPD↓SP (SEQ ID NO: 22)+1 µl GrB-H6 after 12 hours incubation
D: 200 µl H6-TripUB IEPD↓SP (SEQ ID NO: 22)+10 µl GrB-H6 after 12 hours incubation
E: H6-FX-TripUB incubated with $FX_a$
F: H6-IEPD-TN123 (SEQ ID NO: 25) alone after 12 hours incubation
G: 200 µl H6-IEPD-TN123 (SEQ ID NO: 25)+1 µl GrB-H6 after 12 hours incubation
H: 200 µl H6-IEPD-TN123 (SEQ ID NO: 25)+10 µl GrB-H6 after 12 hours incubation
I: GrB-H6 alone in the same concentration as in lanes D and H
J: Murine H6-FX-TN123 cleaved with $FX_a$ Lane B shows non-cleaved H6-TripUB IEPD↓SP (SEQ ID NO: 22) (1), where no GrB-H6 was added, while lanes C and D show the two incubations with 1 and 10 µl GrB-H6 added. In both these lanes the product of the cleavage reaction; correctly cleaved H6-TripUB IEPD↓SP (SEQ ID NO: 22) (2) is seen in addition to the non-cleaved fusion protein. In lane E the construct H6-FX-TripUB, containing the $FX_a$ recognition site IQGR in place of the GrB recognition site IEPD, is cleaved by $FX_a$ giving a product of the same size as the GrB-H6 cleaved H6-TripUB IEPD↓SP (SEQ ID NO: 22).

Lanes F-J show the GrB-H6+H6-IEPD-TN123 (SEQ ID NO: 25) incubations after 12 hours. In lane F is shown non-cleaved H6-IEPD-TN123 (SEQ ID NO: 25) (3). Lanes G and H show how H6-IEPD-TN123 (SEQ ID NO: 25) is cleaved by GrB-H6 when no $Ca^{2+}$ is present (4). The band pattern is explained in FIG. 12. In lane J the murine H6-FX-TN123 construct has been cleaved by $FX_a$ showing the size of the correctly cleaved product.

Marked by (5) in the figure is the position of GrB-H6 with the same concentration as in the samples with 10 µl GrB-H6 added.

Figure 5:
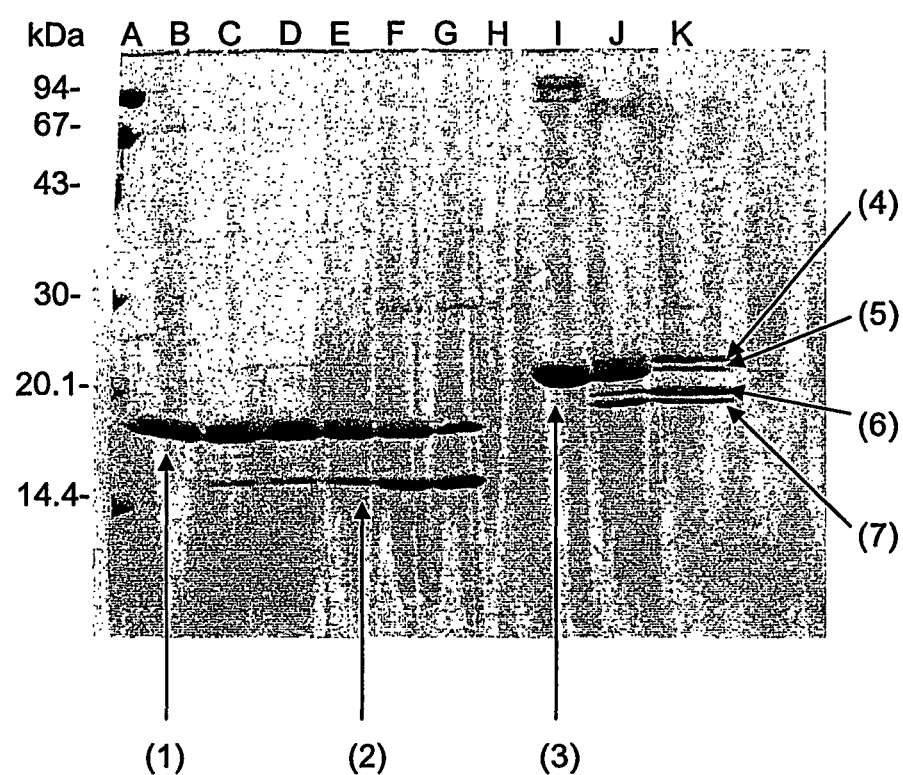

FIG. 5 shows the SDS PAGE of the samples from the GrB-H6+H6-TripUB IEPD↓SP (SEQ ID NO: 22) incubations after 12, 19 and 24 hours of incubation, as well as the samples from the GrB-H6+H6-IEPD-TN123 (SEQ ID NO: 25) incubations.

Description of the lanes A-K:
A: Molecular weight marker
B: H6-TripUB IEPD↓SP (SEQ ID NO: 22) alone after 12 hours incubation
C: 200 µl H6-TripUB IEPD↓SP (SEQ ID NO: 22)+1 µl GrB-H6 after 12 hours incubation
D: 200 µl H6-TripUB IEPD↓SP (SEQ ID NO: 22)+1 µl GrB-H6 after 19 hours incubation
E: 200 µl H6-TripUB IEPD↓SP (SEQ ID NO: 22)+1 µl GrB-H6 after 24 hours incubation
F: 200 µl H6-TripUB IEPD↓SP (SEQ ID NO: 22)+10 µl GrB-H6 after 19 hours incubation
G: 200 µl H6-TripUB IEPD↓SP (SEQ ID NO: 22)+10 µl GrB-H6 after 24 hours incubation
H: GrB-H6 alone diluted as in F and G
I: H6-IEPD-TN123 (SEQ ID NO: 25) alone after 12 hours incubation
J: 200 µl H6-IEPD-TN123 (SEQ ID NO: 25)+1 µl GrB-H6 after 12 hours incubation K: 200 μl H6-IEPD-TN123 (SEQ ID NO: 25)+10 μl GrB-H6 after 12 hours incubation Lane B shows non-cleaved H6-TripUB IEPD↓SP (SEQ ID NO: 22) (1). In lanes C-E the correctly cleaved product appears in all lanes, marked by (2) in the figure. The more GrB-H6 added and the longer the incubation time, the more cleavage product appears in the lanes.

Figure 2:
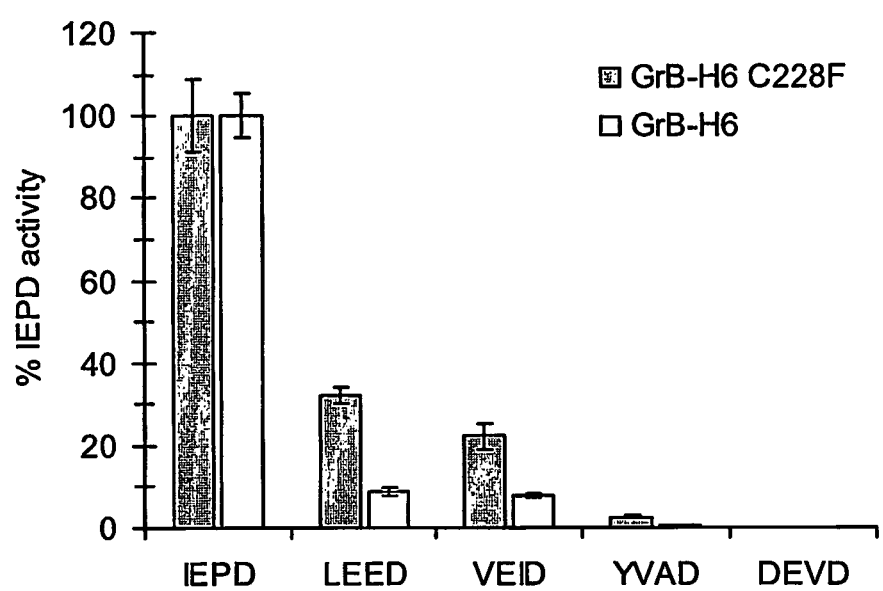
FIG. 2 shows the activity of both GrB-H6 and GrB-H6 C228F towards several chromogenic substrates: Ac-IEPD-pNA, Ac-LEED-pNA, Ac-VEID-pNA, Ac-YVAD-pNA, and Ac-DEVD-pNA. The activity assay was carried out in 500 µl 100 mM HEPES pH 7.75 with a substrate concentration of 400 µM and 1 µg protease added for each measurement. All measurements were done at 23° C. and in triplicate, and the activities obtained were normalized by setting the activity measured on Ac-IEPD-pNA to 100%.

Lanes I, J, and K in FIG. 3 are identical to lanes F, G, and H in FIG. 2 with the H6-IEPD-TN123 (SEQ ID NO: 25)+GrB-H6 incubations, though a larger sample has been run on the gel in FIG. 3. The bands are therefore much clearer than in FIG. 2. The band marked with (3) is non-cleaved H6-IEPD-TN123 (SEQ ID NO: 25) and the band pattern marked with (4), (5), (6) and (7) is explained in FIG. 12.

Figure 6:

FIG. 6 explains the simple band pattern observed in FIGS. 2 and 3. When no GrB-H6 is added, no cleavage occurs and only the band from the non-cleaved fusion protein is seen in the gel. When GrB-H6 is added, the small N-terminal sequence is cleaved off and the correctly cleaved product appears on the gel in addition to the remaining non-cleaved fusion protein. The small N-terminal sequence cleaved off by GrB-H6 is too small to be visualized on the SDS gel.

Figure 7:
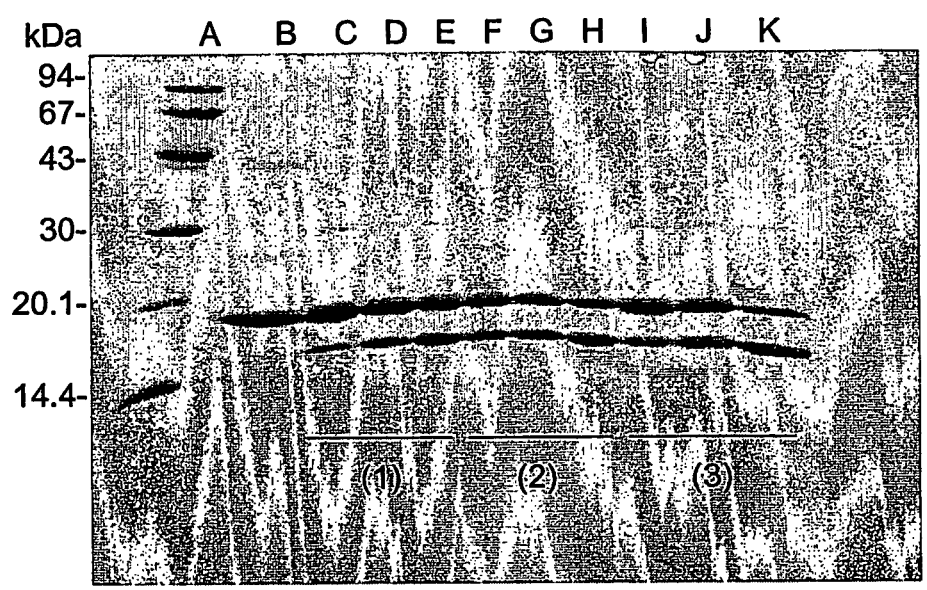
Figure 8:
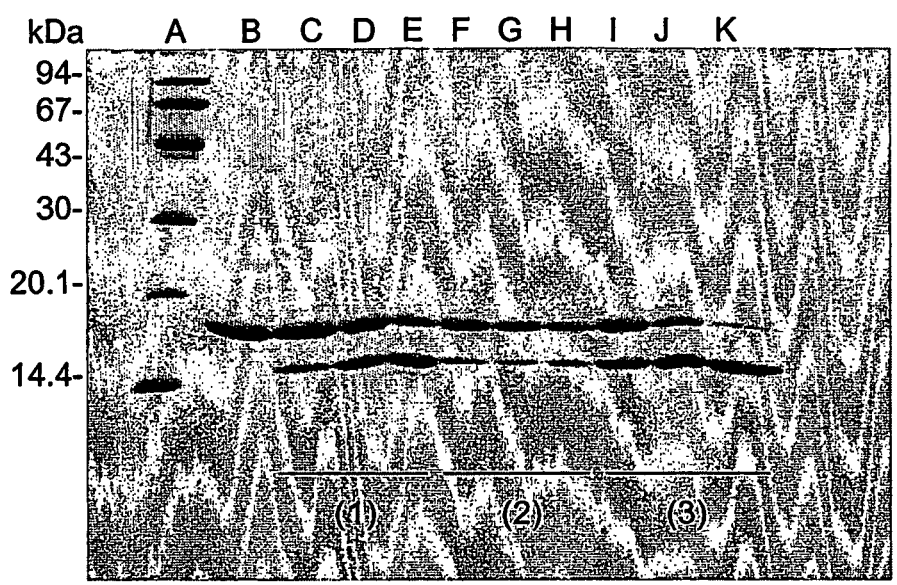
Figure 9:
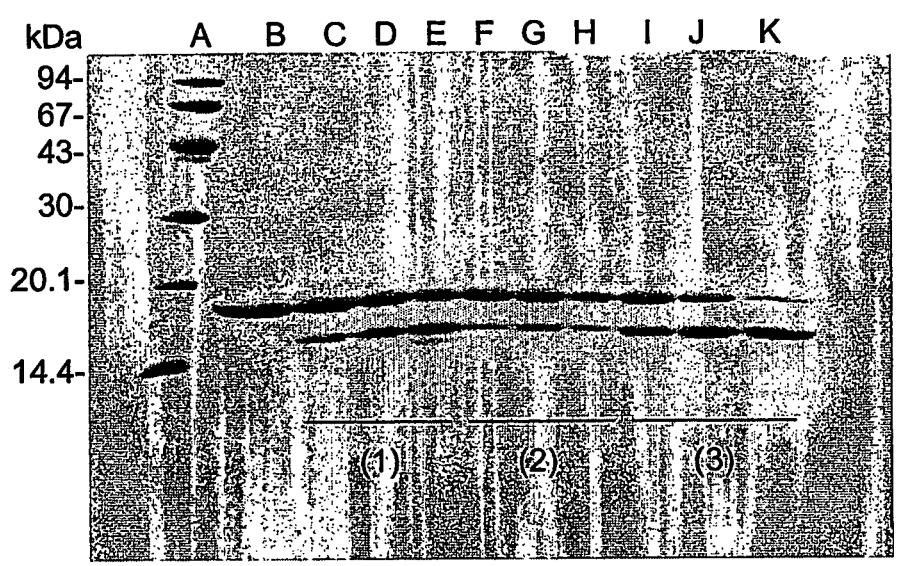

FIGS. 7, 8 and 9 show the SDS PAGE of the samples from the H6-TripUB IEPD↓SP (SEQ ID NO: 22)+GrB-H6 incubations at 23° C. (FIG. 5), 37° C. (FIG. 6) and 42° C. (FIG. 7) with no addition (1), addition of 4.2 mM Ni$^{2+}$ (2) and addition of 4.2 mM Ni$^{2+}$+5 mM NTA (3). Description of the lanes A-K (same for all temperatures):

A: Molecular weight marker
B: Non-cleaved H6-TripUB IEPD↓SP
C: 200 μl H6-TripUB IEPD↓SP (SEQ ID NO: 22)+5 μl GrB-H6, no addition
D: 200 μl H6-TripUB IEPD↓SP (SEQ ID NO: 22)+5 μl GrB-H6, no addition
E: 200 μl H6-TripUB IEPD↓SP (SEQ ID NO: 22)+5 μl GrB-H6, no addition
F: 200 μl H6-TripUB IEPD↓SP (SEQ ID NO: 22)+5 μl GrB-H6, 4.2 mM Ni$^{2+}$
G: 200 μl H6-TripUB IEPD↓SP (SEQ ID NO: 22)+5 μl GrB-H6, 4.2 mM Ni$^{2+}$
H: 200 μl H6-TripUB IEPD↓SP (SEQ ID NO: 22)+5 μl GrB-H6, 4.2 mM Ni$^{2+}$
I: 200 μl H6-TripUB IEPD↓SP (SEQ ID NO: 22)+5 μl GrB-H6, 4.2 mM Ni$^{2+}$ and 5 mM NTA
J: 200 μl H6-TripUB IEPD↓SP (SEQ ID NO: 22)+5 μl GrB-H6, 4.2 mM Ni$^{2+}$ and 5 mM NTA
K: 200 μl H6-TripUB IEPD↓SP (SEQ ID NO: 22)+5 μl GrB-H6, 4.2 mM Ni$^{2+}$ and 5 mM NTA In lanes C-E (1) in all three figures where no Ni$^{2+}$ or NTA was added, the H6-TripUB IEPD↓SP (SEQ ID NO: 22) fusion protein is cleaved at different rates for different temperatures. After 22 hours at 23° C. approximately 40% of the fusion protein has been cleaved. At 37° C. and 42° C. more was cleaved after 22 hours than at 23° C., approximately 60% at 37° C. and 50% at 42° C.

Because of the precipitation of protein observed at 37° C. and 42° C. with 4.2 mM Ni$^{2+}$ no further cleavage of the fusion protein after 2 hours incubation was seen in the gel.

Therefore less protein was seen in lanes F-H (2) in FIGS. 6 (37° C.) and 7 (42° C.) than in lanes F-H (2) in FIG. 5 (23° C.). In FIG. 5, lanes F-H (2), approximately 50% of the fusion protein was cleaved to product after 22 hours incubation, which is more than was cleaved with no addition of Ni$^{2+}$.

No precipitation was observed with 4.2 mM Ni$^{2+}$+5 mM NTA added to the incubations. In FIG. 5 lanes I-K (3) more product is seen than in lanes C-E (1) and F-H (2), so after 22 hours incubation at 23° C. with both Ni$^{2+}$ and NTA present approximately 60% of the fusion protein has been cleaved compared to only about 40% with no addition and 50% with Ni$^{2+}$ alone.

By further increasing the temperature to 37° C. (FIG. 6 lanes I-K (3)) and 42° C. (FIG. 7 lane I-K (3)) an even greater increase in the rate of cleavage is seen. After 22 hours of incubation at 37° C. almost all the fusion protein is cleaved to the correct product. A little less is cleaved at 42° C. after 22 hours.

Figure 10:
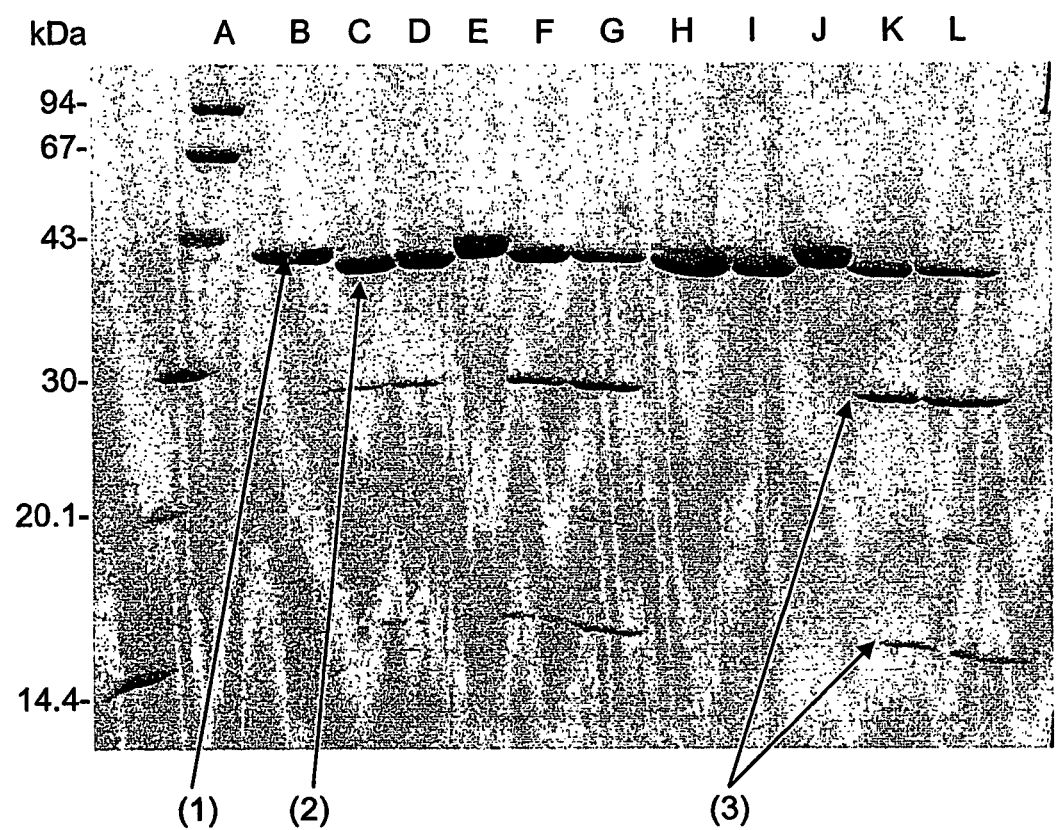

FIG. 10 shows the SDS PAGE of the samples from the H6-IEPD-RAP (SEQ ID NO: 23) incubations with 1 or 10 μl GrB-H6. Description of the lanes (A-L):

A: Molecular weight marker
B: H6-IEPD-RAP (SEQ ID NO: 23) alone after 5 hours incubation
C: 200 μl H6-IEPD-RAP (SEQ ID NO: 23)+1 μl GrB-H6 after 5 hours incubation
D: 200 μl H6-IEPD-RAP (SEQ ID NO: 23)+10 μl GrB-H6 after 5 hours incubation
E: H6-IEPD-RAP (SEQ ID NO: 23) alone after 23 hours incubation
F: 200 μl H6-IEPD-RAP (SEQ ID NO: 23)+1 μl GrB-H6 after 23 hours incubation
G: 200 μl H6-IEPD-RAP (SEQ ID NO: 23)+10 μl GrB-H6 after 23 hours incubation
H: H6-IEGR-RAP cut partly with FX$_a$, purified
I: H6-IEGR-RAP cut almost completely with FX$_a$, purified
J: H6-IEPD-RAP (SEQ ID NO: 23) alone after 26 hours incubation
K: 200 μl H6-IEPD-RAP (SEQ ID NO: 23)+1 μl GrB-H6 after 26 hours incubation
L: 200 μl H6-IEPD-RAP (SEQ ID NO: 23)+10 μl GrB-H6 after 26 hours incubation Non-cleaved H6-IEPD-RAP (SEQ ID NO: 23) (1) is shown in lanes B, E, and J. In lanes C and D it is clear that all the H6-IEPD-RAP (SEQ ID NO: 23) has been cleaved to give the final product (2) after only 5 hours incubation with either 1 or 10 μl GrB-H6 as described above. It is also clear that there is at least one internal cleavage site in RAP giving rise to the two lower bands appearing in these lanes, i.e. the final product is cleaved into two pieces both visible on the gel (3). Lanes F and G and lanes K and L show essentially the same as lanes C and D, though the samples were taken later, after 23 and 26 hours of incubation with GrB-H6 giving rise to more cleavage in the apparent internal site in RAP.

In lanes H and I is shown purified samples of H6-IEGR-RAP cleaved partly (lane H) or completely (lane I) by FX$_a$ to give the final RAP product. In these lanes the degradation products from any internal cleavage by FX$_a$ has been removed by purification.

Figure 11:
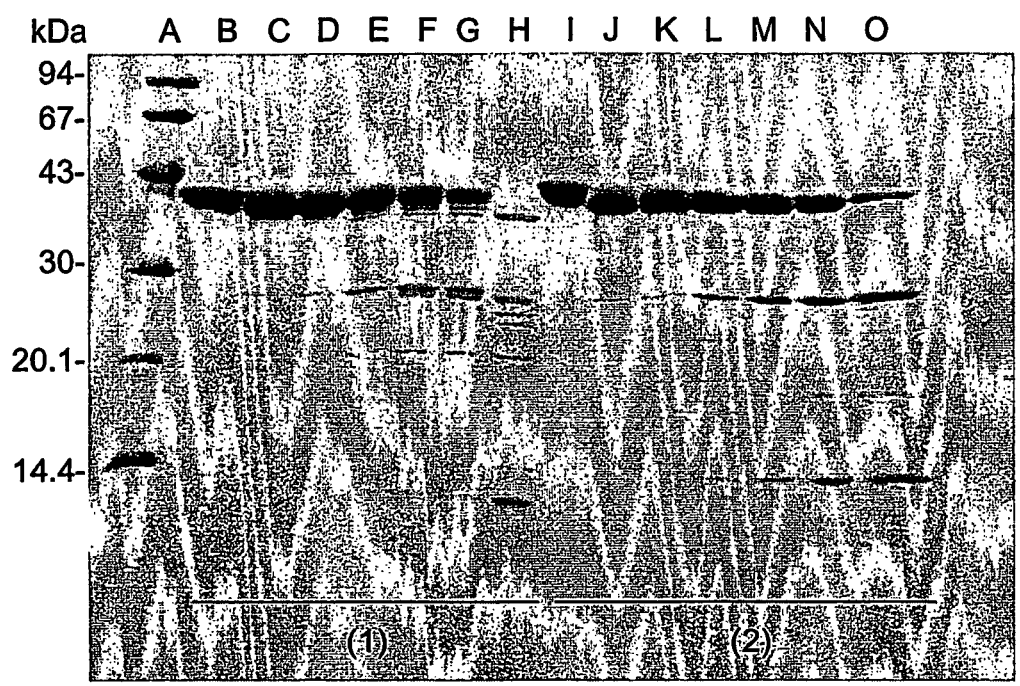

FIG. 11 shows the SDS PAGE of the samples from the H6-IEPD-RAP (SEQ ID NO: 23)+GrB-H6 and the H6-IEGR-RAP+FX$_a$ incubations. Description of the lanes (A-O):

A: Molecular weight marker
B: H6-IEGR-RAP alone after 27 hours incubation
C: 400 μl H6-IEGR-RAP+1 μl FX$_a$ after ½ hour incubation
D: 400 μl H6-IEGR-RAP+1 μl FX$_a$ after 1 hour incubation
E: 400 μl H6-IEGR-RAP+1 μl FX$_a$ after 3 hours incubation
F: 400 μl H6-IEGR-RAP+1 μl FX$_a$ after 5 hours incubation
G: 400 μl H6-IEGR-RAP+1 μl FX$_a$ after 7 hours incubation
H: 400 μl H6-IEGR-RAP+1 μl FX$_a$ after 27 hours incubation
I: H6-IEPD-RAP (SEQ ID NO: 23) alone after 27 hours incubation J: 400 μl H6-IEPD-RAP (SEQ ID NO: 23)+2 μl GrB-H6 after ½ hour incubation K: 400 μl H6-IEPD-RAP (SEQ ID NO: 23)+2 μl GrB-H6 after 1 hour incubation L: 400 μl H6-IEPD-RAP (SEQ ID NO: 23)+2 μl GrB-H6 after 3 hours incubation M: 400 μl H6-IEPD-RAP (SEQ ID NO: 23)+2 μl GrB-H6 after 5 hours incubation N: 400 μl H6-IEPD-RAP (SEQ ID NO: 23)+2 μl GrB-H6 after 7 hours incubation O: 400 μl H6-IEPD-RAP (SEQ ID NO: 23)+2 μl GrB-H6 after 27 hours incubation In lanes B-H are the samples from the H6-IEGR-RAP incubation (1), where lane B shows non-cleaved H6-IEGR-RAP. Lane C-H shows that after only ½ hour almost all of the fusion protein has been cleaved by $FX_a$ to give the correct product. In lanes D-G some degradation products show up, and in lane H after 27 hours of incubation all of the fusion protein has been degraded to give a variety of smaller pieces, and there is no correctly cleaved product left.

Lanes I-O shows the samples from the H6-IEPD-RAP (SEQ ID NO: 23) incubation (2).

Lane I shows non-cleaved H6-IEPD-RAP (SEQ ID NO: 23), and as for H6-IEGR-RAP nearly all the H6-IEPD-RAP (SEQ ID NO: 23) has been cleaved correctly after only ½ hour incubation with GrB-H6, as is seen in lane J. In lanes K-N degradation products show up, but not nearly as many as for the H6-IEGR-RAP incubation. In lane O after 27 hours of incubation there is still quite a lot of correctly cleaved product left.

Figure 12:
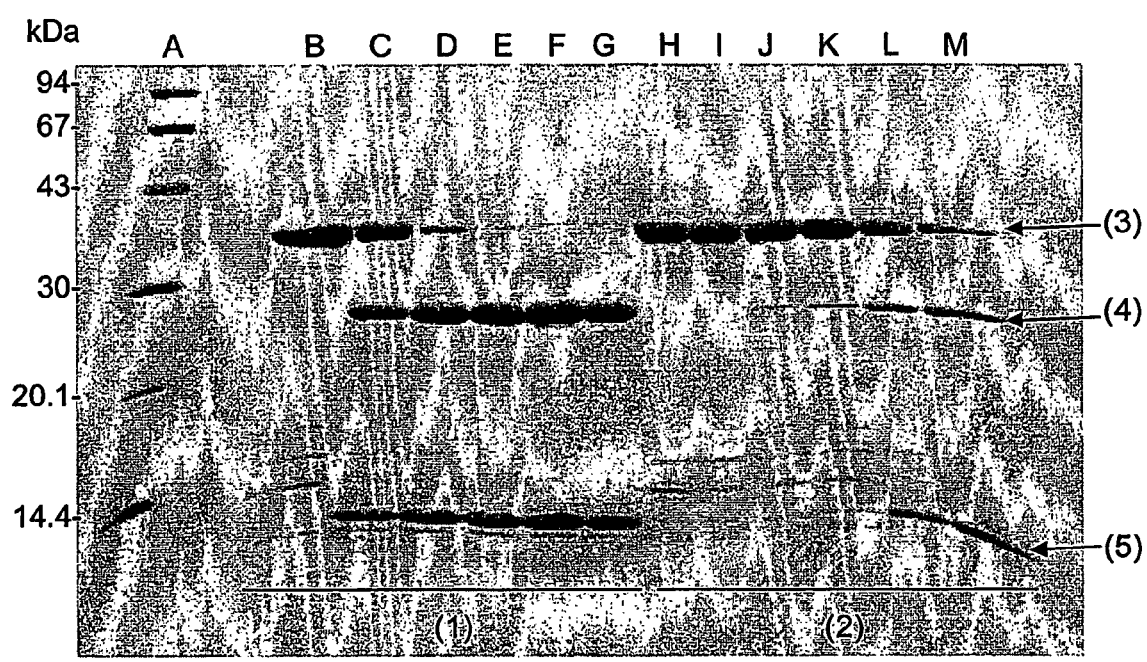

FIG. 12 shows the SDS PAGE of the samples from the H6Ubi-IEPD-ApoA1 (SEQ ID NO: 24)+GrB-H6 C228F and the H6Ubi-IEGR-ApoA1+$FX_a$ incubations. Description of the lanes (A-M):

A: Molecular weight marker

B: H6Ubi-IEPD-ApoA1 (SEQ ID NO: 24) alone, 0 hours incubation

C: 400 μg H6Ubi-IEPD-ApoA1 (SEQ ID NO: 24)+0.4 μg GrB-H6 C228F, 1 hour incubation D: 400 μg H6Ubi-IEPD-ApoA1 (SEQ ID NO: 24)+0.4 μg GrB-H6 C228F, 3 hour incubation E: 400 μg H6Ubi-IEPD-ApoA1 (SEQ ID NO: 24)+0.4 μg GrB-H6 C228F, 6 hours incubation F: 400 μg H6Ubi-IEPD-ApoA1 (SEQ ID NO: 24)+0.4 μg GrB-H6 C228F, 24 hours incubation G: 400 μg H6Ubi-IEPD-ApoA1 (SEQ ID NO: 24)+0.4 μg GrB-H6 C228F, 48 hours incubation H: H6Ubi-IEGR-ApoA1 alone, 0 hours incubation I: 350 μg H6Ubi-IEGR-ApoA1+0.35 μg $FX_a$, 1 hour incubation J: 350 μg H6Ubi-IEGR-ApoA1+0.35 μg $FX_a$, 3 hour incubation K: 350 μg H6Ubi-IEGR-ApoA1+0.35 μg $FX_a$, 6 hours incubation L: 350 μg H6Ubi-IEGR-ApoA1+0.35 μg $FX_a$, 24 hours incubation M: 350 μg H6Ubi-IEGR-ApoA1+0.35 μg $FX_a$, 48 hours incubation In lanes B-G are the samples from the H6Ubi-IEPD-ApoA1 (SEQ ID NO: 24) incubation (1), where lane B shows the non-cleaved H6Ubi-IEPD-ApoA1 (SEQ ID NO: 24) preparation. Lanes H-M shows the samples from the H6Ubi-IEGR-ApoA1 incubation (2), where lane H shows the non-cleaved H6Ubi-IEGR-ApoA1 preparation. The position of the intact, non-cleaved fusion proteins is indicated by (3). The bands marked by (4) is the correctly cleaved ApoA1 product, whereas the bands marked with (5) H6Ubi fusion partner.

Figure 13:
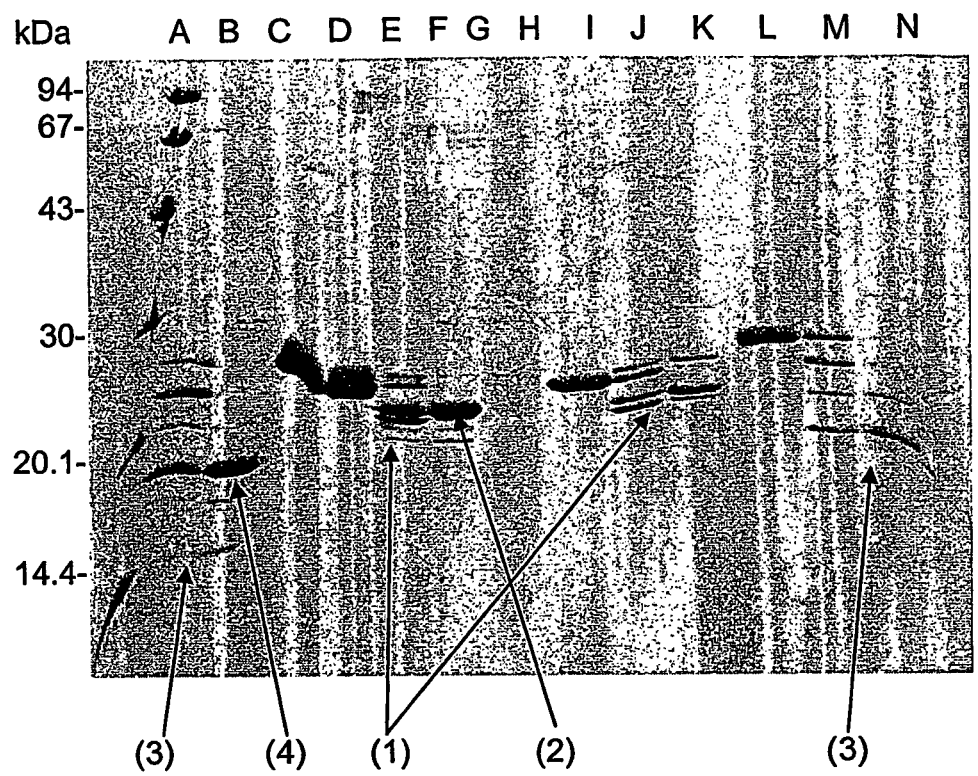

FIG. 13 shows the SDS PAGE of the samples from the H6-IEPD-TN123 (SEQ ID NO: 25)+GrB-H6 incubation after 12 hours and 5 days without addition of $Ca^{2+}$. Some samples have been reduced. Description of the lanes (A-N):

A: Molecular weight marker

B: 200 μl H6-IEPD-TN123 (SEQ ID NO: 25)+1 μl GrB-H6 after 5 days incubation, sample reduced C: 200 μl H6-IEPD-TN123 (SEQ ID NO: 25)+10 μl GrB-H6 after 5 days incubation, sample reduced D+E: H6-IEPD-TN123 (SEQ ID NO: 25) alone after 5 days incubation F: 200 μl H6-IEPD-TN123 (SEQ ID NO: 25)+1 μl GrB-H6 after 5 days incubation G: 200 μl H6-IEPD-TN123 (SEQ ID NO: 25)+10 μl GrB-H6 after 5 days incubation H: GrB-H6 alone diluted as in C and G I: H6-IEPD-TN123 (SEQ ID NO: 25) alone after 12 hours incubation J: 200 μl H6-IEPD-TN123 (SEQ ID NO: 25)+1 μl GrB-H6 after 12 hours incubation K: 200 μl H6-IEPD-TN123 (SEQ ID NO: 25)+10 μl GrB-H6 after 12 hours incubation L: H6-IEPD-TN123 (SEQ ID NO: 25) alone after 12 hours incubation, sample reduced M: 200 μl H6-IEPD-TN123 (SEQ ID NO: 25)+1 μl GrB-H6 after 12 hours incubation, sample reduced N: 200 μl H6-IEPD-TN123 (SEQ ID NO: 25)+10 μl GrB-H6 after 12 hours incubation, sample reduced Lanes I-K are identical to lanes F-H in FIG. 2 and I-K in FIG. 3, i.e. samples after 12 hours incubation with either 0, 0.2 or 2 μg GrB-H6. Here the band pattern (1) indicates an internal cleavage site in the TN123 part of H6-IEPD-TN123 (SEQ ID NO: 25), and the pattern is further explained in FIG. 12. Lanes D-G show the incubations after 5 days, and here most of the fusion protein has been cleaved. In lane G (10 μl GrB-H6 added) almost all of the fusion protein has been cleaved twice (2); at the IEPD↓ sequence as well as at the internal site in TN123 with the sequence AQPD↓.

Lanes L-N and lanes B-D show the same samples after 12 hours and after 5 days, respectively, but here the samples are reduced. This band pattern (3) is also explained in FIG. 12 and again almost all of the fusion protein has been cleaved twice after 5 days with 10 μl GrB-H6, lane C (4).

Figure 14:
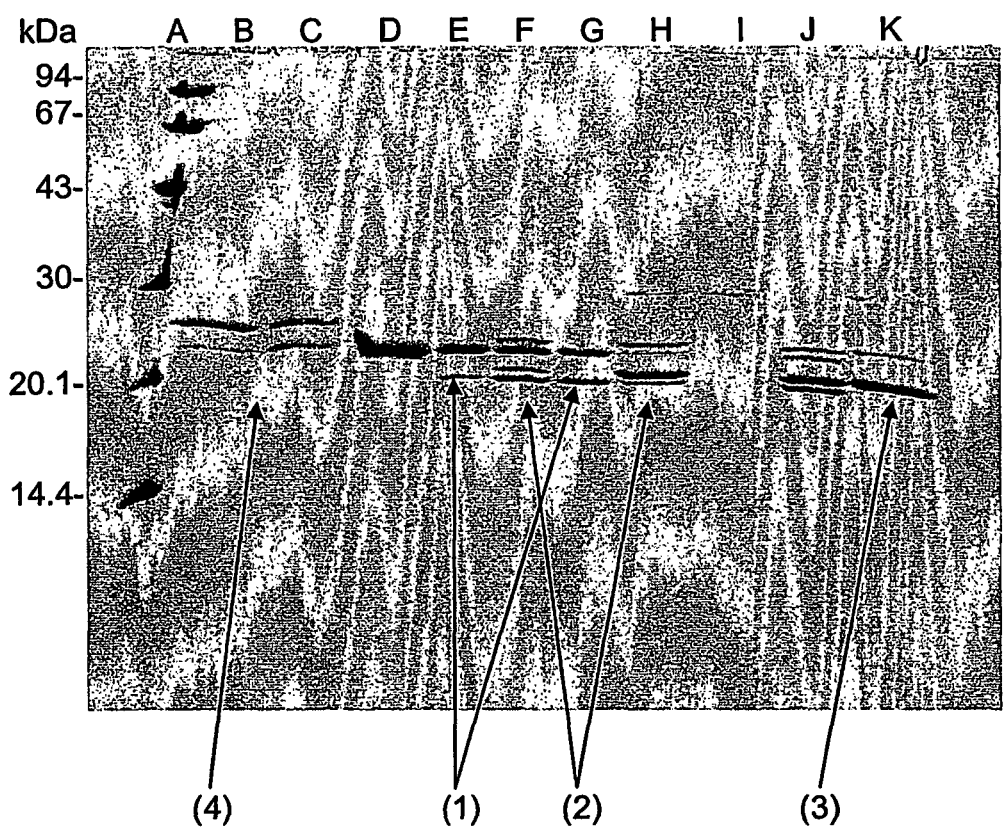

FIG. 14 shows the SDS PAGE of the samples from the H6-IEPD-TN123 (SEQ ID NO: 25)+GrB-H6 incubation after 12 hours and 2 days with the addition of 5 mM $Ca^{2+}$. Some samples have been reduced. Description of the lanes (A-K):

A: Molecular weight marker

B: 200 μl H6-IEPD-TN123 (SEQ ID NO: 25)+1 μl GrB-H6 and 5 mM $CaCl_2$, sample reduced C: 200 μl H6-IEPD-TN123 (SEQ ID NO: 25)+10 μl GrB-H6 and 5 mM $CaCl_2$, sample reduced D: H6-IEPD-TN123 (SEQ ID NO: 25) alone E: 200 μl H6-IEPD-TN123 (SEQ ID NO: 25)+1 μl GrB-H6 and 5 mM $CaCl_2$ F: 200 μl H6-IEPD-TN123 (SEQ ID NO: 25)+1 μl GrB-H6 and no $CaCl_2$ G: 200 μl H6-IEPD-TN123 (SEQ ID NO: 25)+10 μl GrB-H6 and 5 mM $CaCl_2$ H: 200 μl H6-IEPD-TN123 (SEQ ID NO: 25)+10 μl GrB-H6 and no $CaCl_2$ I: GrB-H6 alone diluted as in G and H J: 200 μl H6-IEPD-TN123 (SEQ ID NO: 25)+1 μl GrB-H6 and no $CaCl_2$ after 2 days incubation K: 200 μl H6-IEPD-TN123 (SEQ ID NO: 25)+10 μl GrB-H6 and no $CaCl_2$ after 2 days incubation Lanes B-H and J-K show the incubations of H6-IEPD-TN123 (SEQ ID NO: 25) with GrB-H6 after 12 hours and 2 days, respectively.

Lane D shows non-cleaved H6-IEPD-TN123. Comparing lane E and G (+5 mM Ca$^{2+}$) with lane F and H (no Ca$^{2+}$) only two bands appear with 5 mM Ca$^{2+}$ present (1), while four bands appear (2) when no Ca$^{2+}$ in present, as described for FIGS. 2, 3, 10 and 12. After 12 hours incubation with 10 µl GrB-H6 approximately 40% of the fusion protein has been correctly cleaved when Ca$^{2+}$ is present (lane G), while the cleavage of the two sites when no Ca$^{2+}$ is present happens a bit faster (lane H after 12 hours and K after 2 days). In lane K almost all the fusion protein has been cleaved twice (3). The samples in lanes B and C are reduced and still only two bands appear (4); the non-cleaved H6-IEPD-TN123 and the correctly cleaved product, where the H6 is removed.

Figure 15:
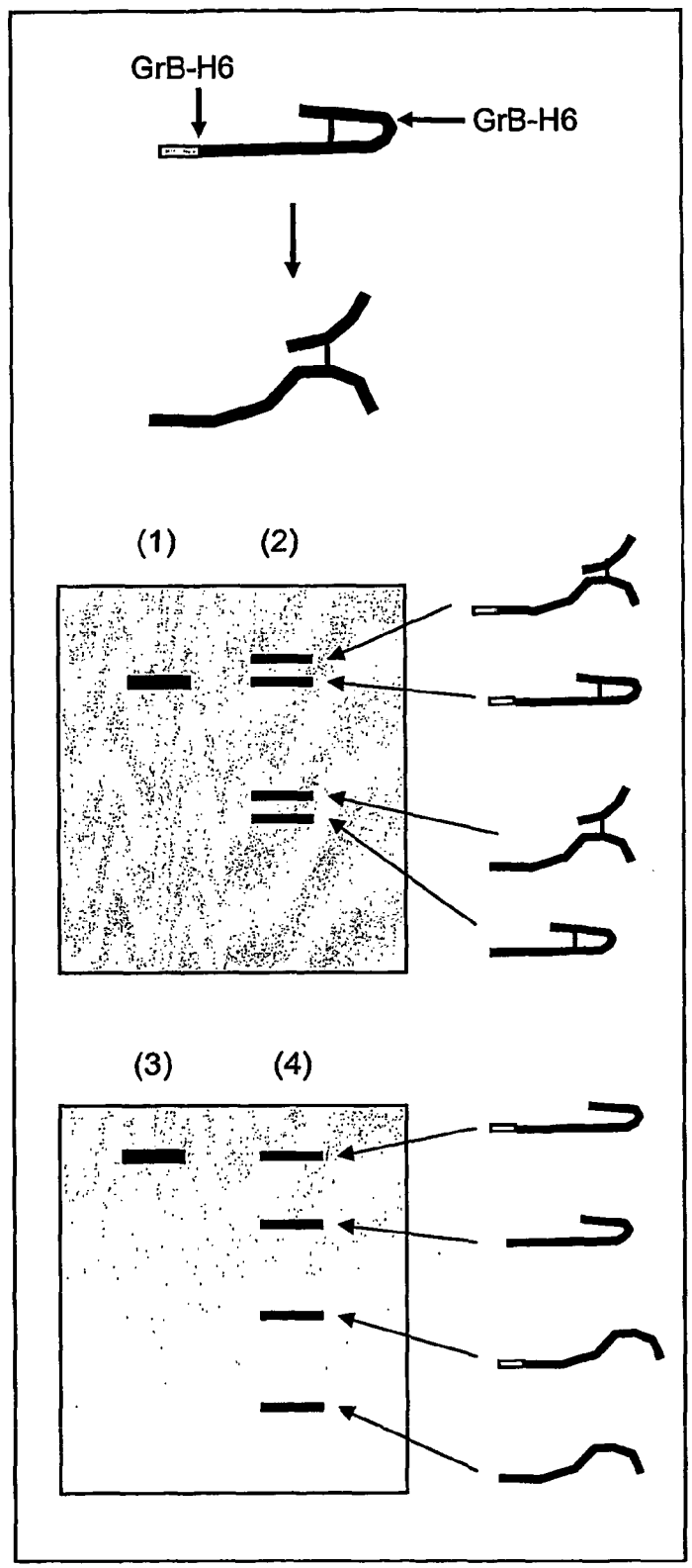
Figure 15:
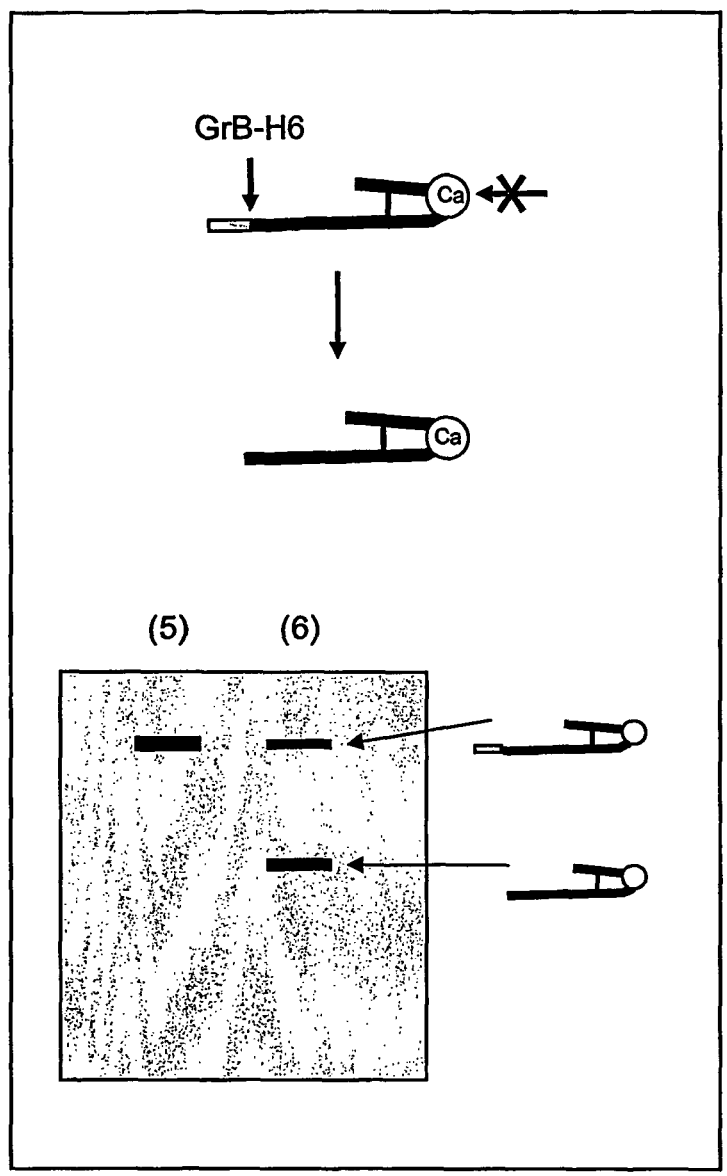

FIG. 15 shows a schematic representation of the band pattern observed on the SDS PAGE gels in FIGS. 2, 3, 10 and 11.

(A): When no Ca$^{2+}$ is present the H6-IEPD-TN123 (SEQ ID NO: 25) construct is cleaved at two different sites indicated by "GrB-H6→". The small N-terminal part cleaved off is too small to be visualized on the gel. The resulting molecule consists of two polypeptide chains held together by a disulfide bond.

(1) and (2): In a non-reducing gel the band pattern in (2) is obtained when the cleavage is not complete. (1) is the non-cleaved H6-IEPD-TN123 (SEQ ID NO: 25), and in (2) the remaining non-cleaved fusion protein is the second band from the top. The top band in (2) is H6-IEPD-TN123 (SEQ ID NO: 25) cleaved at the internal site, AQPD↓ (SEQ ID NO: 84), giving a molecule of the same size as non-cleaved H6-IEPD-TN123, but less compact. The band at the bottom is the correctly cleaved fusion protein, whereas the third band from the top is the fusion protein cleaved twice; both at the correct IEPD↓ (SEQ ID NO: 63) site and at the internal AQPD↓ site (SEQ ID NO: 84). When cleaved at the internal site the molecule is less compact and therefore migrates shorter in the gel than the correctly cleaved fusion protein.

(3) and (4): If the samples are reduced the band pattern in (4) is observed. Here any disulfide bonds are broken, so only single polypeptide chains are seen in the gel. (3) shows the position of the non-cleaved, reduced H6-IEPD-TN123 (SEQ ID NO: 25). The top band in (4) is the remaining non-cleaved H6-IEPD-TN123 (SEQ ID NO: 25), while the second band from the top is the correctly cleaved and reduced H6-IEPD-TN123 (SEQ ID NO: 25). Under the reducing conditions the molecules cleaved at the internal site are no longer held together by any disulfide bonds, and only the larger one of the two polypeptides after internal cleavage can be seen in the gel. Therefore the third band from the top is the larger part of the internally cleaved fusion protein, and the bottom band is this larger part after cleavage at both the internal site and at the correct IEPD↓ (SEQ ID NO: 63) site.

(B): When 5 mM Ca$^{2+}$ is added to the incubations, no internal cleavage is observed. Ca$^{2+}$ ions bind to the H6-IEPD-TN123 (SEQ ID NO: 25) molecule in a way preventing GrB-H6 from cleaving the fusion protein at the internal AQPD↓ site. With the AQPD↓ (SEQ ID NO: 84) site rendered inaccessible cleavage only occurs at the correct IEPD↓ (SEQ ID NO: 63) site.

(5) and (6): When only cleavage at the correct IEPD↓ (SEQ ID NO: 63) site occurs the band pattern in (6) is seen. The position of the non-cleaved H6-IEPD-TN123 (SEQ ID NO: 25) is shown in (5), and so the top band in (6) is the remaining non-cleaved H6-IEPD-TN123 (SEQ ID NO: 25). The bottom band is the fusion protein cleaved only once at the correct site. The small N-terminal peptide is too small to be visualized in the gel.

Figure 16:
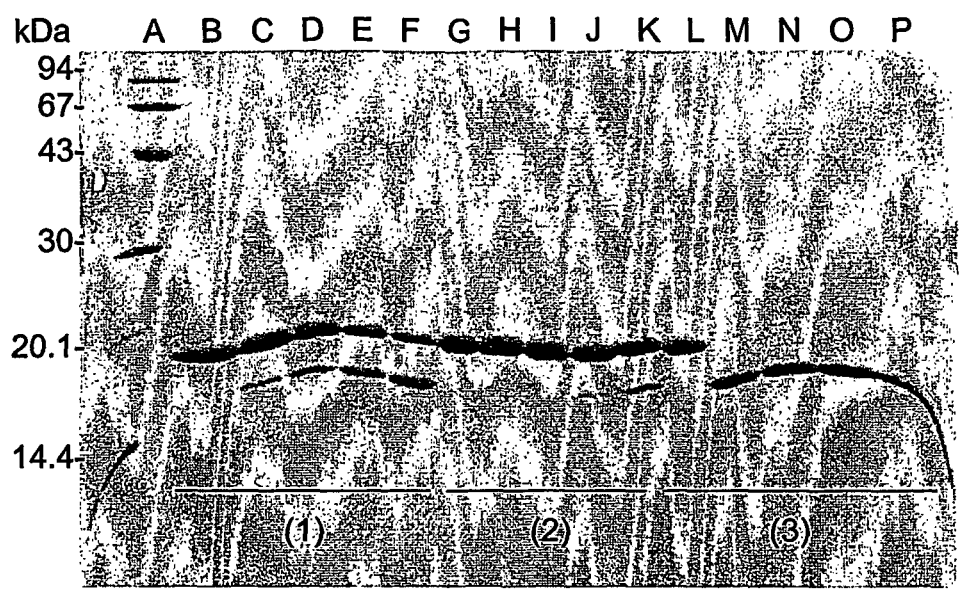

FIG. 16 shows samples from the incubations of three of the five H6-TripUB variants with GrB-H6. The three variants are H6-TripUB IEPD↓SP (SEQ ID NO: 22), H6-TripUB IQAD↓SP (SEQ ID NO: 26) and H6-TripUB IQAD↓SG (SEQ ID NO: 27). Description of the lanes (A-P):

A: Molecular weight marker

B: H6-TripUB IEPD↓SP (SEQ ID NO: 22) alone after 24 hours incubation

C: 200 µl H6-TripUB IEPD↓SP (SEQ ID NO: 22)+5 µl GrB-H6 after 2 hours incubation D: 200 µl H6-TripUB IEPD↓SP (SEQ ID NO: 22)+5 µl GrB-H6 after 6 hours incubation E: 200 µl H6-TripUB IEPD↓SP (SEQ ID NO: 22)+5 µl GrB-H6 after 24 hours incubation F: 200 µl H6-TripUB IEPD↓SP (SEQ ID NO: 22)+5 µl GrB-H6 after 48 hours incubation G: H6-TripUB IQAD↓SP (SEQ ID NO: 26) alone after 24 hours incubation H: 200 µl H6-TripUB IQAD↓SP (SEQ ID NO: 26)+5 µl GrB-H6 after 2 hours of incubation I: 200 µl H6-TripUB IQAD↓SP (SEQ ID NO: 26)+5 µl GrB-H6 after 6 hours of incubation J: 200 µl H6-TripUB IQAD↓SP (SEQ ID NO: 26)+5 µl GrB-H6 after 24 hours of incubation K: 200 µl H6-TripUB IQAD↓SP (SEQ ID NO: 26)+5 µl GrB-H6 after 48 hours of incubation L: H6-TripUB IQAD↓SG (SEQ ID NO: 27) alone after 24 hours incubation M: 200 µl H6-TripUB IQAD↓SG (SEQ ID NO: 27)+5 µl GrB-H6 after 2 hours incubation N: 200 µl H6-TripUB IQAD↓SG (SEQ ID NO: 27)+5 µl GrB-H6 after 6 hours incubation O: 200 µl H6-TripUB IQAD↓SG (SEQ ID NO: 27)+5 µl GrB-H6 after 24 hours incubation P: 200 µl H6-TripUB IQAD↓SG (SEQ ID NO: 27)+5 µl GrB-H6 after 48 hours incubation In lane B is shown non-cleaved H6-TripUB IEPD↓SP (SEQ ID NO: 22), while more and more correctly cleaved product appear in lanes C-F after incubation with GrB-H6. In lane F after 48 hours incubation approximately ⅔ of the original amount of non-cleaved H6-TripUB IEPD↓SP (SEQ ID NO: 22) has been correctly cleaved. In lanes G-K is shown the H6-TripUB IQAD↓SP (SEQ ID NO: 26) samples giving more or less the same picture as for H6-TripUB IEPD↓SP (SEQ ID NO: 22) with non-cleaved H6-TripUB IQAD↓SP (SEQ ID NO: 26) in lane G and an increasing amount of correctly cleaved product in lanes H-K. The cleavage, though, is much slower than cleavage of the IEPD↓SP (SEQ ID NO: 85) sequence and only a small amount has been cleaved after 48 hours incubation. For the H6-TripUB IQAD↓SG (SEQ ID NO: 27) samples in lanes L-P it is evident that the cleavage is very much faster than for both H6-TripUB IEPD↓SP (SEQ ID NO: 22) and H6-TripUB IQAD↓SP (SEQ ID NO: 26). Lane L shows the non-cleaved H6-TripUB IQAD↓SG (SEQ ID NO: 27) and already after only 2 hours incubation the majority of the fusion protein has been cleaved to give the correct product.

Figure 17:
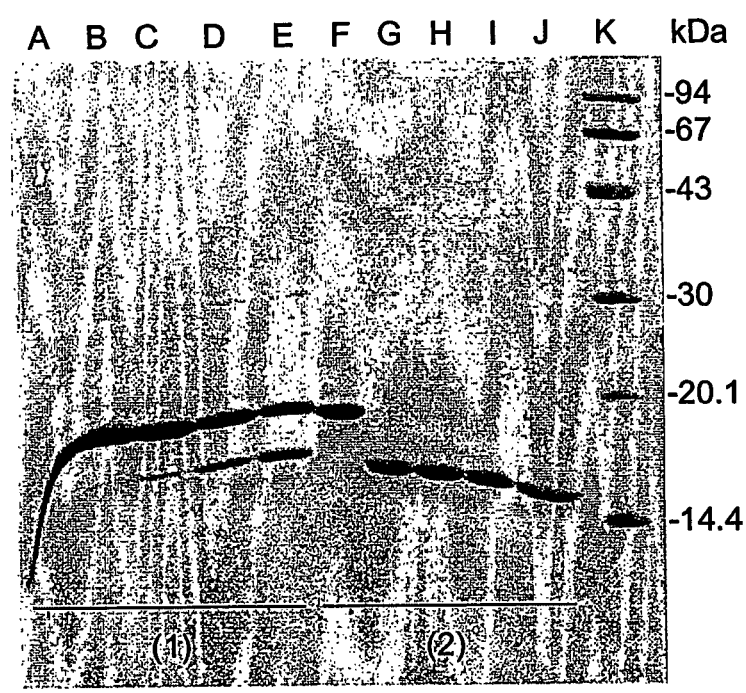

FIG. 17 shows samples from the incubations of two of the five H6-TripUB variants with GrB-H6. The two remaining variants are H6-TripUB VGPD↓SP (SEQ ID NO: 28) and H6-TripUB VGPD↓FG (SEQ ID NO: 29). Description of the lanes (A-K):

A: H6-TripUB VGPD↓SP (SEQ ID NO: 28) alone after 24 hours incubation

B: 200 µl H6-TripUB VGPD↓SP (SEQ ID NO: 28)+5 µl GrB-H6 after 2 hours incubation C: 200 µl H6-TripUB VGPD↓SP (SEQ ID NO: 28)+5 µl GrB-H6 after 6 hours incubation D: 200 µl H6-TripUB VGPD↓P (SEQ ID NO: 28)+5 µl GrB-H6 after 24 hours incubation E: 200 µl H6-TripUB VGPD↓SP (SEQ ID NO: 28)+5 µl GrB-H6 after 48 hours incubation F: H6-TripUB VGPD↓FG (SEQ ID NO: 29) alone after 24 hours incubation G: 200 µl H6-TripUB VGPD↓FG (SEQ ID NO: 29)+5 µl GrB-H6 after 2 hours incubation H: 200 µl H6-TripUB VGPD↓FG (SEQ ID NO: 29)+5 µl GrB-H6 after 6 hours incubation I: 200 µl H6-TripUB VGPD↓FG (SEQ ID NO: 29)+5 µl GrB-H6 after 24 hours incubation J: 200 µl H6-TripUB VGPD↓FG (SEQ ID NO: 29)+5 µl GrB-H6 after 48 hours incubation K: Molecular weight marker In lane A is non-cleaved H6-TripUB VGPD↓SP (SEQ ID NO: 28) and in lanes B-E more and more correctly cleaved product appears as seen for H6-TripUB IEPD↓SP (SEQ ID NO: 28) (lanes B-F FIG. 16). Approximately half the amount of fusion protein has been cleaved after 48 hours. In lane F non-cleaved H6-TripUB VGPD↓FG (SEQ ID NO: 29) is shown and in lanes G-J the correctly cleaved product of H6-TripUB VGPD↓FG (SEQ ID NO: 29) appears. After only 2 hours incubation all the fusion protein has been correctly cleaved.

Figure 18:
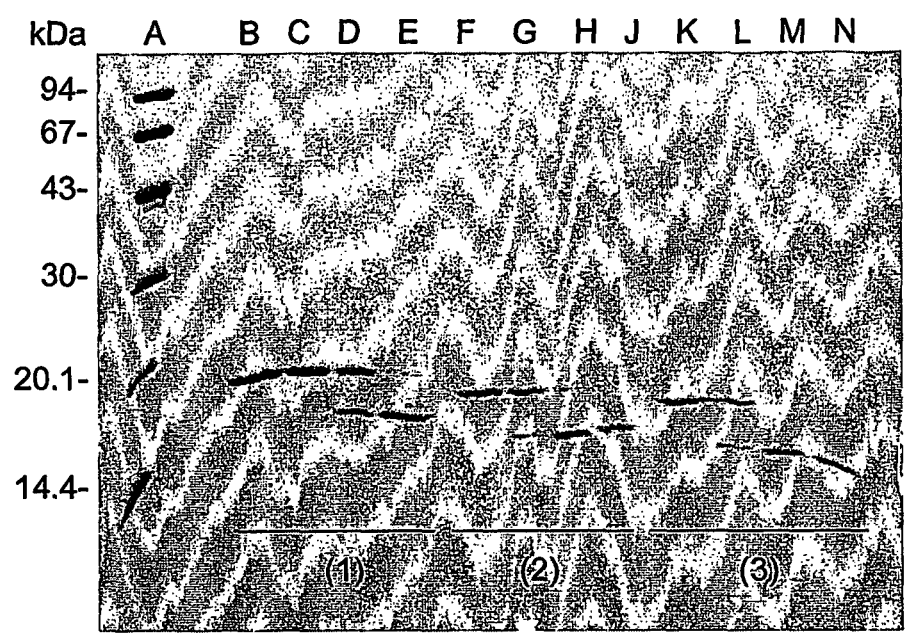

FIG. 18 shows samples from the incubations of H6-TripUB IEPD↓SP (SEQ ID NO: 22), H6-TripUB IEPD↓TQ (SEQ ID NO: 30) and H6-TripUB IEPD↓IV (SEQ ID NO: 31) with GrB-H6 C228F in the protease:fusion protein ratio of 1:500 at 23° C.

Description of lanes A-M:

A: Molecular weight marker

B: H6-TripUB IEPD↓SP (SEQ ID NO: 22), 0 hours incubation

C: 250 µl H6-TripUB IEPD↓SP (SEQ ID NO: 22)+1 µl GrB-H6 C228F, 4 hours incubation D: 250 µl H6-TripUB IEPD↓SP (SEQ ID NO: 22)+1 µl GrB-H6 C228F, 24 hours incubation E: 250 µl H6-TripUB IEPD↓SP (SEQ ID NO: 22)+1 µl GrB-H6 C228F, 96 hours incubation F: H6-TripUB IEPD↓TQ (SEQ ID NO: 30), 0 hours incubation G: 250 µl H6-TripUB IEPD↓TQ (SEQ ID NO: 30)+1 µl GrB-H6 C228F, 4 hours incubation H: 250 µl H6-TripUB IEPD↓TQ (SEQ ID NO: 30)+1 µl GrB-H6 C228F, 24 hours incubation I: 250 µl H6-TripUB IEPD↓TQ (SEQ ID NO: 30)+1 µl GrB-H6 C228F, 96 hours incubation J: H6-TripUB IEPD↓IV (SEQ ID NO: 31), 0 hours incubation K: 250 µl H6-TripUB IEPD↓IV (SEQ ID NO: 31)+1 µl GrB-H6 C228F, 4 hours incubation L: 250 µl H6-TripUB IEPD↓IV (SEQ ID NO: 31)+1 µl GrB-H6 C228F, 24 hours incubation M: 250 µl H6-TripUB IEPD↓IV (SEQ ID NO: 31)+1 µl GrB-H6 C228F, 96 hours incubation In lanes B-E the cleavage of H6-TripUB IEPD↓SP (SEQ ID NO: 22) is shown (1), where the cleavage is almost 100% complete after 96 hours. Lanes F-I are the cleavage of H6-TripUB IEPD↓TQ (SEQ ID NO: 30) (2), and this is app. 100% completed after only 24 hours. This is also the case for the cleavage of H6-TripUB IEPD↓IV (SEQ ID NO: 31) (3) shown in lanes J-M. The bands for the intact and cleaved H6-TripUB IEPD↓TQ (SEQ ID NO: 30) are all positioned slightly lower in the gel, than the bands for H6-TripUB IEPD↓SP (SEQ ID NO: 22), since H6-TripUB IEPD↓TQ (SEQ ID NO: 30) is a deletion mutant of H6-TripUB IEPD↓SP (SEQ ID NO: 22). The bands for H6-TripUB IEPD↓IV (SEQ ID NO: 31), another deletion mutant, are positioned even lower, since the deletion is larger than the one in H6-TripUB IEPD↓TQ (SEQ ID NO: 30).

Figure 19:
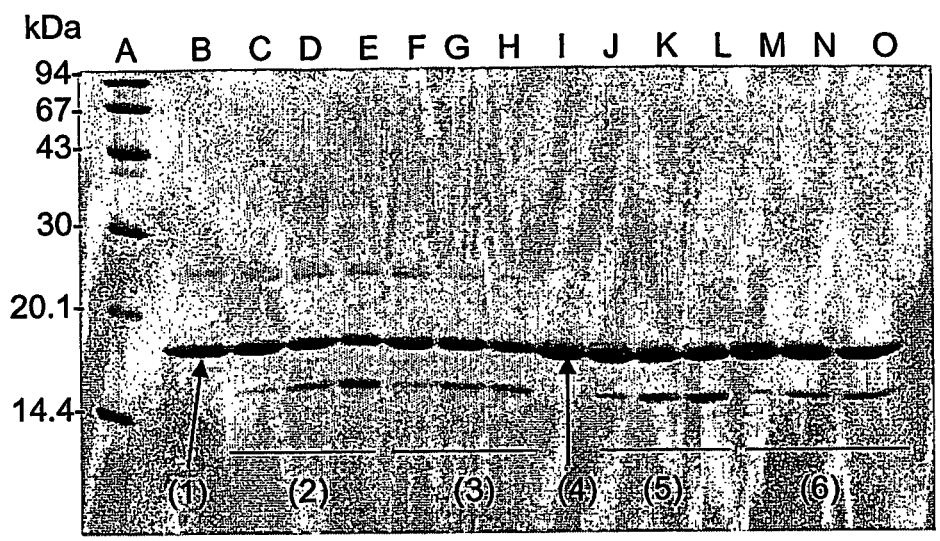
Figure 19:
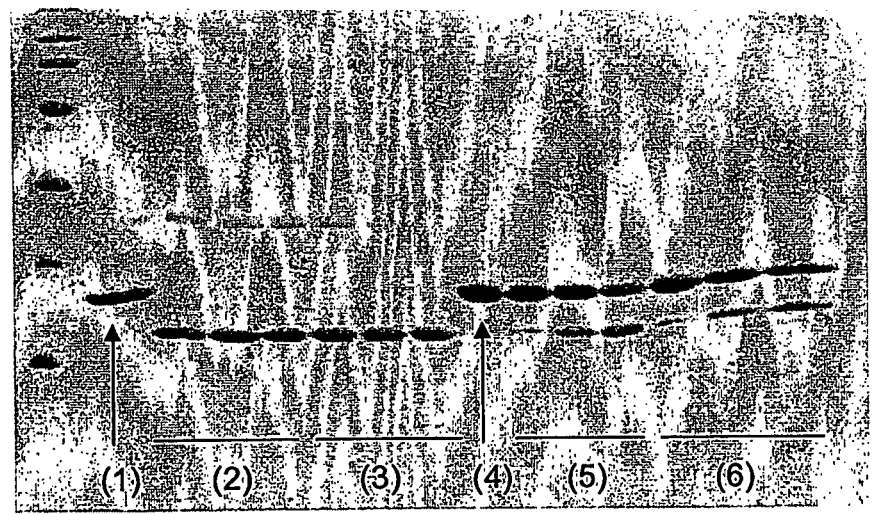

FIG. 19, Panel A shows samples from the incubations of H6-TripUB IEPD↓SP (SEQ ID NO: 22) and H6-TripUB IEPD↓EP (SEQ ID NO: 32) with GrB-H6 C228F in the protease:fusion protein ratio of 1:500 in a total volume of 200 µl at both 21° C. and 37° C.

Description of lanes A-O:

A: Molecular weight marker

B: H6-TripUB IEPD↓SP (SEQ ID NO: 22), 0 hours incubation

C: 24 µg H6-TripUB IEPD↓SP (SEQ ID NO: 22)+0.048 µg GrB-H6 C228F, 21° C., 4 hours D: 24 µg H6-TripUB IEPD↓SP (SEQ ID NO: 22)+0.048 µg GrB-H6 C228F, 21° C., 24 hours E: 24 µg H6-TripUB IEPD↓SP (SEQ ID NO: 22)+0.048 µg GrB-H6 C228F, 21° C., 48 hours F: 24 µg H6-TripUB IEPD↓SP (SEQ ID NO: 22)+0.048 µg GrB-H6 C228F, 37° C., 4 hours G: 24 µg H6-TripUB IEPD↓SP (SEQ ID NO: 22)+0.048 µg GrB-H6 C228F, 37° C., 24 hours H: 24 µg H6-TripUB IEPD↓SP (SEQ ID NO: 22)+0.048 µg GrB-H6 C228F, 37° C., 48 hours I: H6-TripUB IEPD↓EP, 0 hours incubation J: 36 µg H6-TripUB IEPD↓EP (SEQ ID NO: 32)+0.072 µg GrB-H6 C228F, 21° C., 4 hours K: 36 µg H6-TripUB IEPD↓EP (SEQ ID NO: 32)+0.072 µg GrB-H6 C228F, 21° C., 24 hours L: 36 µg H6-TripUB IEPD↓EP (SEQ ID NO: 32)+0.072 µg GrB-H6 C228F, 21° C., 48 hours M: 36 µg H6-TripUB IEPD↓EP (SEQ ID NO: 32)+0.072 µg GrB-H6 C228F, 37° C., 4 hours N: 36 µg H6-TripUB IEPD↓EP (SEQ ID NO: 32)+0.072 µg GrB-H6 C228F, 37° C., 24 hours O: 36 µg H6-TripUB IEPD↓EP (SEQ ID NO: 32)+0.072 µg GrB-H6 C228F, 37° C., 48 hours The intact, non-cleaved H6-TripUB IEPD↓SP (SEQ ID NO: 22) is shown in lane B (1), while the cleavages at 21° C. and 37° C. are shown in lanes C-E (2) and lanes F-H (3), respectively. There is almost no difference in the two temperatures. After 48 hours approximately 40% has been cleaved at 21° C. Non-cleaved H6-TripUB IEPD↓EP (SEQ ID NO: 32) is shown in lane I (4), while the cleavage reactions at 21° C. and 37° C. are shown in lanes J-L (5) and lanes M-O (6), respectively. Again almost no difference between the two temperature, and after 48 hours at 21° C. approximately 35-40% has been cleaved. i.e. the GrB-H6 C228F cleaves both substrates equally well.

FIG. 19, Panel B shows samples from the incubations of H6-TripUB IEPD↓EG (SEQ ID NO: 32) and H6-TripUB IEPD↓EP (SEQ ID NO: 32) with GrB-H6 C228F in the protease:fusion protein ratio of 1:500 in a total volume of 200 µl at both 22° C. and 37° C.

Description of lanes A-O:

A: Molecular weight marker

B: H6-TripUB IEPD↓EG (SEQ ID NO: 33), 0 hours incubation

C: 40 µg H6-TripUB IEPD↓EG (SEQ ID NO: 33)+0.08 µg GrB-H6 C228F, 23° C., 6 hours D: 40 µg H6-TripUB IEPD↓EG (SEQ ID NO: 33)+0.08 µg GrB-H6 C228F, 23° C., 24 hours E: 40 μg H6-TripUB IEPD↓EG (SEQ ID NO: 33)+0.08 μg GrB-H6 C228F, 23° C., 50 hours F: 40 μg H6-TripUB IEPD↓EG (SEQ ID NO: 33)+0.08 μg GrB-H6 C228F, 37° C., 6 hours G: 40 μg H6-TripUB IEPD↓EG (SEQ ID NO: 33)+0.08 μg GrB-H6 C228F, 37° C., 24 hours H: 40 μg H6-TripUB IEPD↓EG (SEQ ID NO: 33)+0.08 μg GrB-H6 C228F, 37° C., 50 hours I: H6-TripUB IEPD↓EP (SEQ ID NO: 32), 0 hours incubation J: 38 μg H6-TripUB IEPD↓EP (SEQ ID NO: 32)+0.08 μg GrB-H6 C228F, 23° C., 6 hours K: 38 μg H6-TripUB IEPD↓EP (SEQ ID NO: 32)+0.08 μg GrB-H6 C228F, 23° C., 24 hours L: 38 μg H6-TripUB IEPD↓EP (SEQ ID NO: 32)+0.08 μg GrB-H6 C228F, 23° C., 50 hours M: 38 μg H6-TripUB IEPD↓EP (SEQ ID NO: 32)+0.08 μg GrB-H6 C228F, 37° C., 6 hours N: 38 μg H6-TripUB IEPD↓EP (SEQ ID NO: 32)+0.08 μg GrB-H6 C228F, 37° C., 24 hours O: 38 μg H6-TripUB IEPD↓EP (SEQ ID NO: 32)+0.08 μg GrB-H6 C228F, 37° C., 50 hours The intact, non-cleaved H6-TripUB IEPD↓EG (SEQ ID NO: 33) is shown in lane B (1), while the cleavages at 21° C. and 37° C. are shown in lanes C-E (2) and lanes F-H (3), respectively. There is almost no difference in the two temperatures, and after only 6 hours the cleavage has been completed. Non-cleaved H6-TripUB IEPD↓LEP (SEQ ID NO: 32) is shown in lane I (4), while the cleavage reactions at 21° C. and 37° C. are shown in lanes J-L (5) and lanes M-O (6), respectively. As in FIG. 19 Panel A after 50 hours at 21° C. approximately 40% has been cleaved. Surprisingly the GrB-H6 C228F cleaves the IEPD↓EG (SEQ ID NO: 86) substrate much better than IEPD↓SP (SEQ ID NO: 85) and IEPD↓EP (SEQ ID NO: 87).

Figure 20:
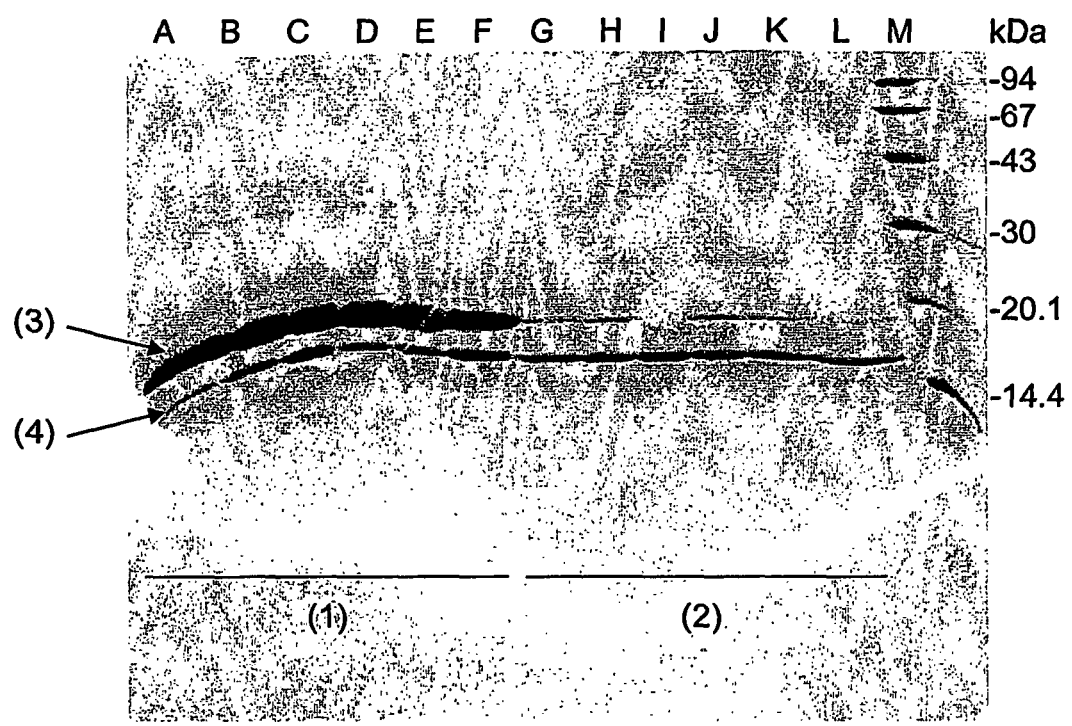

FIG. 20 shows samples from the incubation of either H6-TripUB IQAD↓SP (SEQ ID NO: 26) or H6-TripUB IQAD↓SG (SEQ ID NO: 27) with the six different preparations of immobilized GrB-H6 C228F, experiment A-F, described in Example 9.

Description of lanes A-M:

A: H6-TripUB IQAD↓SP (SEQ ID NO: 26)+immobilized GrB-H6 C228F, experiment A

B: H6-TripUB IQAD↓SP (SEQ ID NO: 26)+immobilized GrB-H6 C228F, experiment B

C: H6-TripUB IQAD↓SP (SEQ ID NO: 26)+immobilized GrB-H6 C228F, experiment C

D: H6-TripUB IQAD↓SP (SEQ ID NO: 26)+immobilized GrB-H6 C228F, experiment D

E: H6-TripUB IQAD↓SP (SEQ ID NO: 26)+immobilized GrB-H6 C228F, experiment E

F: H6-TripUB IQAD↓SP (SEQ ID NO: 26)+immobilized GrB-H6 C228F, experiment F

G: H6-TripUB IQAD↓SG (SEQ ID NO: 27)+immobilized GrB-H6 C228F, experiment A

H: H6-TripUB IQAD↓SG (SEQ ID NO: 27)+immobilized GrB-H6 C228F, experiment B

I: H6-TripUB IQAD↓SG (SEQ ID NO: 27)+immobilized GrB-H6 C228F, experiment C

J: H6-TripUB IQAD↓SG (SEQ ID NO: 27)+immobilized GrB-H6 C228F, experiment D

K: H6-TripUB IQAD↓SG (SEQ ID NO: 27)+immobilized GrB-H6 C228F, experiment E

L: H6-TripUB IQAD↓SG (SEQ ID NO: 27)+immobilized GrB-H6 C228F, experiment F

M: Molecular weight marker

The incubation with H6-TripUB IQAD↓SP (SEQ ID NO: 26) are shown in lanes A-F (1), while the H6-TripUB IQAD↓SG (SEQ ID NO: 27) incubations are shown in lanes G-L (2). The band representing non-cleaved fusion protein (H6-TripUB IQAD↓SP (SEQ ID NO: 26) or H6-TripUB IQAD↓SG (SEQ ID NO: 27)) is marked by (3) and the position of the bands for the correctly cleaved products are marked by (4).

EXAMPLES

Example 1

Design and Construction of Human Granzyme B Expression Vectors

In order to prepare inactive pro-Granzyme B constructs, a sequence encoding activated human Granzyme B (E.C. 3.4.21.79), i.e. from Ile21 (Ile16 in chymotrypsinogen numbering) to Tyr247, was cloned into a pT7 cloning vector containing a hexa-His tag (H6) C-terminally (pT7 C-term H6), resulting in the expression vector pT7-IEGR-GrB-H6. The sequence, MGSIEGR (SEQ ID NO: 88), containing the blood clotting factor $X_a$ ($FX_a$) recognition sequence IEGR was thereby placed just N-terminally to Ile21 in Granzyme B providing a $FX_a$ cleavage site between Arg (R) and Ile21. The resulting fusion protein pro-Granzyme B containing the $FX_a$ recognition sequence and the C-terminal hexa-His tag is in the following referred to as pro-IEGR-GrB-H6 and is shown in SEQ ID NO:1.

In order to form self-activating pro-Granzyme B proteins, the expression vectors pT7-IEPD-GrB-H6 and pT7-IEAD-GrB-H6 were constructed, wherein the $FX_a$ recognition sequence of IEGR (SEQ ID NO: 89) was substituted with the Granzyme B recognition sites IEPD (SEQ ID NO: 63) or IEAD (SEQ ID NO: 62), respectively. The resulting self-activating GrB proteins are in the following referred to as pro-IEPD-GrB-H6 and pro-IEAD-GrB-H6, respectively and are shown in SEQ ID NO:2 and SEQ ID NO:3. The design and cloning of the vectors is outlined in the following section.

The presence of a free cysteine at amino acid position 228 (using the established standard chymotrypsinogen amino acid numbering system) in human Granzyme B, and in particular in the above described Granzyme B proteins, pro-IEGR-GrB-H6, pro-IEPD-GrB-H6 (SEQ ID NO: 2), and pro-IEAD-GrB-H6 (SEQ ID NO: 3), has the potential to cause complications during the refolding process described in Example 2, decrease stability of the activated enzyme and provide higher non-enzymatic reactivity towards disulfide containing substrates. Therefore a number of recombinant mutant proteins based on pro-IEPD-GrB-H6 (SEQ ID NO: 2) were generated in which the Cys228 amino acid residue (chymotrypsinogen amino acid numbering) was substituted with serine (S), alanine (A), threonine (T), valine (V), or phenylalanine (F) by site-directed mutation of the construct pT7-IEPD-GrB-H6, giving the expression vectors pT7-IEPD-GrB-H6 C228S, pT7-IEPD-GrB-H6 C228A, pT7-IEPD-GrB-H6 C228T, pT7-IEPD-GrB-H6 C228V, and pT7-IEPD-GrB-H6 C228F, respectively. The resulting mutant proteins are in the following referred to as pro-IEPD-GrB-H6 C228S (SEQ ID NO 4), pro-IEPD-GrB-H6 C228A (SEQ ID NO 5), pro-IEPD-GrB-H6 C228T (SEQ ID NO 6), pro-IEPD-GrB-H6 C228V (SEQ ID NO 7), and pro-IEPD-GrB-H6 C228F (SEQ ID NO 8), respectively, and collectively referred to as the pro-IEPD-GrB-H6 C228X mutants. All of these mutants were constructed as self-activating Granzyme B proteases.

Construction of the pT7 C-Term H6 Cloning Vector

The cloning vector pT7 C-term H6, was constructed by ligation of the DNA fragment made from the oligonucleotide primers H6 C-term fw (SEQ ID NO: 9) and H6 C-term rev (SEQ ID NO: 10) into an NcoI and EcoRI cut vector, pT7 (Christensen J H et al., 1991), using standard procedures.

Cloning of Human Granzyme B into pT7 C-Term H6 Cloning Vector

The expression vector pT7-IEGR-GrB-H6, was constructed by ligation of the BamHI and EcoRI restricted DNA fragment GrB EcoRI amplified from a mixture of cDNA, isolated from human bone marrow, human leukocyte, human lymphnodes, and lymphoma (Raji) cells (Clontech Laboratories, Inc cat #7181-1, 7182-1, 7164-1, 7167-1) (with the oligonucleotide primers GrBfw (SEQ ID NO: 11) and GrBrev EcoRI (SEQ ID NO: 12)) into a BamHI and EcoRI cut vector, pT7 C-term H6, using standard procedures. Outlines of the resulting nucleotide sequence of GrB EcoRI, is given as SEQ ID NO: 13.

Construction of Expression Vectors for Self-Activating Human Granzyme B, Pro-IEPD-GrB-H6 and Pro-IEAD-GrB-H6

The expression vectors pT7-IEPD-GrB-H6 and pT7-IEAD-GrB-H6 encoding the self-activating pro-Granzyme B proteins, were constructed by using the QuikChange™ Site-Directed Mutagenesis Kit (STRATAGENE, Catalog #200518) according to the manufacturers' protocol. The expression vector pT7-IEGR-GrB-H6 was used as template. The oligonucleotide primers GrB GR-PD fw and GrB GR-PD rev (SEQ ID NO: 14 and 15) were used for construction of pT7-IEPD-GrB-H6 and the oligonucleotide primers GrB GR-AD fw and GrB GR-AD rev (SEQ ID NO: 16 and 17) were used for construction of pT7-IEAD-GrB-H6.

Construction of Expression Vectors for the Self-Activating Pro-IEPD-GrB-H6 C228X Mutants The expression vectors pT7-IEPD-GrB-H6 C228X encoding the self-activating pro-GrB-H6 C228X (SEQ ID NO: 4, 5, 6, 7 and 8) mutant proteins, were all constructed by using the QuikChange™ Site-Directed Mutagenesis Kit (STRATAGENE, Catalog #200518) according to the manufacturers' protocol. The expression vector pT7-IEPD-GrB-H6 was used as template. The degenerated oligonucleotide primers GrB SAT fw and GrB SAT rev (SEQ ID NO: 18 and 19) were used for construction of pT7-IEPD-GrB-H6 C228S, pT7-IEPD-GrB-H6 C228A, and pT7-IEPD-GrB-H6 C228S, where D=A, G, or T and H=T, C, or A in the GrB SAT fw and GrB SAT rev primer sequences shown in Table 1. The degenerated oligonucleotide primers GrB VF fw and GrB VF rev (SEQ ID NO: 20 and 21) were used for construction of pT7-IEPD-GrB-H6 C228V and pT7-IEPD-GrB-H6 C228F, where K=G or T and M=A or C in the GrB VF fw and GrB VF rev primer sequences shown in Table 1.

TABLE 1

Oligonucleotide primers

| Primer | Nucleotide sequence | SEQ ID NO. |
|---|---|---|
| H6 C-term fw | 5'-CATGGACGGAAGCTTGAATTCACATCACCATCACCATCACTAACGC-3' | 9 |
| H6 C-term rev | 5'-AATTGCGTTAGTGATGGTGATGGTGATGTGAATTCAAGCTTCCGCT-3' | 10 |
| GrBfw | 5'-CATGGGATCCATCGAGGGTAGGATCATCGGGGGACATGAG-3' | 11 |
| GrBrev EcoRI | 5'-GCGTGAATTCAGGTACCGTTTCATGGTTTTCTTTATCC-3' | 12 |
| GrB GR-PD fw | 5'-TCCATCGAGCCGGATATCATCGGGGGACATGAG-3' | 14 |
| GrB GR-PD rev | 5'-CCCCGATGATATCCGGCTCGATGGATCCCATATG-3' | 15 |
| GrB GR-AD fw | 5'-TCCATCGAGGCTGATATCATCGGGGGACATGAG-3' | 16 |
| GrB GR-AD rev | 5'-CCCCGATGATATCAGCCTCGATGGATCCCATATG-3' | 17 |
| GrB SAT fw | 5'-TCCACGAGCADCCACCMAGTCTCAAG-3' | 18 |
| GrB SAT rev | 5'-AGACTTTGGTGGHGGCTCGTGGAGGC-3' | 19 |
| GrB VF fw | 5'-TCCACGAGCCKTCACCAAAGTCTCAAG-3' | 20 |
| GrB VF rev | 5'-AGACTTTGGTGAMGGCTCGTGGAGGC-3' | 21 |

Example 2

Expression and Refolding of Self-Activating Human Granzyme B $FX_a$ Activatable Recombinant Pro-IEGR-GrB-H6

The $FX_a$ activatable recombinant pro-Granzyme B fusion protein pro-IEGR-GrB-H6 (SEQ ID NO:1) was produced by growing and expressing the expression vector pT7-IEGR-GrB-H6 prepared in Example 1 in *E. coli* BL21 cells in a medium scale (3×1 liter) as described by Studier F W et al. (1990). Exponentially growing cultures at 37° C. were at $OD_{600}$=0.8 infected with bacteriophage ACE6 at a multiplicity of approximately 5. Cultures were grown at 37° C. and 50 min after infection 0.1 g/L rifampicin (dissolved as 0.1 g/mL in methanol) was added. After another three hours at 37° C. the cells were harvested by centrifugation. The cells were lysed by osmotic shock and sonification and total cellular protein was extracted into phenol (adjusted to pH 8 with Trisma base). The protein was precipitated from the phenol phase by addition of 2.5 volumes of ethanol and centrifugation. The protein pellet was dissolved in a buffer containing 6 M guanidinium chloride, 50 mM Tris-HCl pH 8, and 100 mM dithiothreitol. Following gel-filtration on Sephadex™ G-25 Fine (Amersham Biosciences) into 8 M Urea, 0.5 M NaCl, 50 mM Tris-HCl pH 8, and 5 mM 2-mercaptoethanol, the crude protein preparation was applied onto a $Ni^{2+}$-activated NTA-agarose column ($Ni^{2+}$-NTA-agarose, Quiagen).

Upon application of the crude protein extract onto the $Ni^{2+}$-NTA-agarose column, the fusion protein, pro-IEGR-GrB-H6 was purified from the majority of *E. coli* and λ phage proteins by washing with one column volume of the loading buffer followed by one column volume of 8 M Urea, 0.5 M NaCl, 50 mM sodium phosphate pH 6.3 and 5 mM 2-mercaptoethanol, ½ column volume of 6 M guanidinium chloride, 50 mM Tris-HCl pH 8, and 5 mM 2-mercaptoethanol and finally ½ column volume of 8 M Urea, 0.5 M NaCl, 50 mM Tris-HCl pH 8, and 3 mM reduced glutathione.

The pro-IEGR-GrB-H6 fusion protein was refolded on the $Ni^{2+}$-NTA-agarose column using the cyclic refolding procedure described by Thøgersen et al. (International Patent Application WO 9418227). The gradient manager profile is described in the below Table 2 with 0.5 M NaCl, 50 mM Tris-HCl pH 8, 2 mM reduced glutathione, and 0.2 mM oxidized glutathione as buffer A and 6 M urea, 0.5 NaCl, 50 mM Tris-HCl pH 8, and 3 mM reduced glutathione as buffer B.

TABLE 2

| Step | Time (min) | Flow (mL/min) | % A | % B |
|---|---|---|---|---|
| 1 | 0 | 2 | 100 | 0 |
| 2 | 45 | 2 | 100 | 0 |
| 3 | 46 | 2 | 0 | 100 |
| 4 | 52 | 2 | 0 | 100 |
| 5 | 60 | 2 | 100 | 0 |
| 6 | 105 | 2 | 100 | 0 |
| 7 | 106 | 2 | 4 | 96 |
| 8 | 113 | 2 | 4 | 96 |
| 9 | 120 | 2 | 100 | 0 |
| 10 | 165 | 2 | 100 | 0 |
| 11 | 166 | 2 | 8 | 92 |
| 12 | 172 | 2 | 8 | 92 |
| 13 | 180 | 2 | 100 | 0 |
| 14 | 225 | 2 | 100 | 0 |
| 15 | 226 | 2 | 10 | 90 |
| 16 | 232 | 2 | 10 | 90 |
| 17 | 240 | 2 | 100 | 0 |
| 18 | 285 | 2 | 100 | 0 |
| 19 | 286 | 2 | 12 | 88 |
| 20 | 292 | 2 | 12 | 88 |
| 21 | 300 | 2 | 100 | 0 |
| 22 | 345 | 2 | 100 | 0 |
| 23 | 346 | 2 | 14 | 86 |
| 24 | 352 | 2 | 14 | 86 |
| 25 | 360 | 2 | 100 | 0 |
| 26 | 405 | 2 | 100 | 0 |
| 27 | 406 | 2 | 16 | 84 |
| 28 | 412 | 2 | 16 | 84 |
| 29 | 420 | 2 | 100 | 0 |
| 30 | 465 | 2 | 100 | 0 |
| 31 | 466 | 2 | 18 | 82 |
| 32 | 472 | 2 | 18 | 82 |
| 33 | 480 | 2 | 100 | 0 |
| 34 | 525 | 2 | 100 | 0 |
| 35 | 526 | 2 | 20 | 80 |
| 36 | 532 | 2 | 20 | 80 |
| 37 | 540 | 2 | 100 | 0 |
| 38 | 585 | 2 | 100 | 0 |
| 39 | 586 | 2 | 22 | 78 |
| 40 | 592 | 2 | 22 | 78 |
| 41 | 600 | 2 | 100 | 0 |
| 42 | 645 | 2 | 100 | 0 |
| 43 | 646 | 2 | 24 | 76 |
| 44 | 652 | 2 | 24 | 76 |
| 45 | 660 | 2 | 100 | 0 |
| 46 | 705 | 2 | 100 | 0 |
| 47 | 706 | 2 | 30 | 70 |
| 48 | 713 | 2 | 30 | 70 |
| 49 | 720 | 2 | 100 | 0 |
| 50 | 765 | 2 | 100 | 0 |
| 51 | 766 | 2 | 35 | 65 |
| 52 | 772 | 2 | 35 | 65 |
| 53 | 780 | 2 | 100 | 0 |
| 54 | 825 | 2 | 100 | 0 |
| 55 | 826 | 2 | 40 | 60 |
| 56 | 832 | 2 | 40 | 60 |
| 57 | 840 | 2 | 100 | 0 |
| 58 | 885 | 2 | 100 | 0 |
| 59 | 886 | 2 | 45 | 55 |
| 60 | 892 | 2 | 45 | 55 |
| 61 | 900 | 2 | 100 | 0 |
| 62 | 945 | 2 | 100 | 0 |
| 63 | 946 | 2 | 50 | 50 |
| 64 | 952 | 2 | 50 | 50 |
| 65 | 960 | 2 | 100 | 0 |
| 66 | 1005 | 2 | 100 | 0 |
| 67 | 1006 | 2 | 55 | 45 |
| 68 | 1012 | 2 | 55 | 45 |
| 69 | 1020 | 2 | 100 | 0 |
| 70 | 1065 | 2 | 100 | 0 |
| 71 | 1066 | 2 | 60 | 40 |
| 72 | 1072 | 2 | 60 | 40 |
| 73 | 1080 | 2 | 100 | 0 |
| 74 | 1125 | 2 | 100 | 0 |
| 75 | 1126 | 2 | 60 | 40 |
| 76 | 1132 | 2 | 60 | 40 |
| 77 | 1140 | 2 | 100 | 0 |
| 78 | 1185 | 2 | 100 | 0 |
| 79 | 1186 | 2 | 60 | 40 |
| 80 | 1192 | 2 | 60 | 40 |
| 81 | 1200 | 2 | 100 | 0 |
| 82 | 1245 | 2 | 100 | 0 |
| 83 | 1246 | 2 | 65 | 35 |
| 84 | 1252 | 2 | 65 | 35 |
| 85 | 1260 | 2 | 100 | 0 |
| 86 | 1305 | 2 | 100 | 0 |
| 87 | 1306 | 2 | 65 | 35 |
| 88 | 1312 | 2 | 65 | 35 |
| 89 | 1319 | 2 | 100 | 0 |
| 90 | 1364 | 2 | 100 | 0 |
| 91 | 1365 | 2 | 65 | 35 |
| 92 | 1371 | 2 | 65 | 35 |
| 93 | 1378 | 2 | 100 | 0 |
| 94 | 1423 | 2 | 100 | 0 |

After completion of the cyclic refolding procedure, the pro-IEGR-GrB-H6 (SEQ ID NO: 1) fusion protein was eluted from the $Ni^{2+}$-NTA-agarose column with a buffer containing 0.5 M NaCl, 50 mM Tris-HCl pH 8, and 10 mM EDTA pH 8.

After elution from the $Ni^{2+}$-NTA column the pro-IEGR-GrB-H6 (SEQ ID NO: 1) protein was diluted with 1 volumes of 50 mM Tris-HCl pH 8.0 before the pH was adjusted to 7 with HCl. The protein was then applied onto a SP Sepharose™ Fast Flow (Amersham Biosciences) ion exchange column. The protein was eluted over 10 column volumes with a linear gradient from 250 mM NaCl, 50 mM Tris-HCl pH 7.0 to 1 M NaCl, 50 mM Tris-HCl pH 7.0. Samples from the elution profile appear as a single distinct band in SDS-PAGE analysis and migrate with the anticipated molecular weight of 27.4 kDa for monomeric pro-IEGR-GrB-H6 (SEQ ID NO: 1).

Self-Activating Pro-IEPD-GrB-H6 and Pro-IEAD-GrB-H6

The self-activating recombinant Granzyme B fusion proteins pro-IEPD-GrB-H6 (SEQ ID NO:2) and pro-IEAD-GrB-H6 (SEQ ID NO:3) were produced by expression from the vectors pT7-IEPD-GrB-H6 and pT7-IEAD-GrB-H6 prepared in Example 1, where the expression, refolding, and purification was performed essentially as described for pro-IEGR-GrB-H6 above.

The self activation of the two enzymes, pro-IEPD-GrB-H6 (SEQ ID NO: 2) and pro-IEAD-GrB-H6 (SEQ ID NO: 3) was followed as described in Example 3 below.

Self-Activating Pro-IEPD-GrB-H6 C228X Mutants

All the pro-IEPD-GrB-H6 C228X mutants (SEQ ID NOS. 4, 5, 6, 7 and 8) were expressed from the pT7-IEPD-GrB-H6 C228X expression vectors essentially as described for the expression of pro-IEGR-GrB-H6 above. Refolding of the pro-IEPD-GrB-H6 C228X mutants were also done essentially as described for pro-IEGR-GrB-H6 above, and activation on a cation exchange column was done as described above for pro-IEPD-GrB-H6 and pro-IEAD-GrB-H6.

Purification and complete activation of the self-activating pro-IEPD-GrB-H6 C228X mutants (SEQ ID NOs: 4, 5, 6, 8 and 8) was done in only four hours by applying the refolded protein, still in the pro-form, to a cation exchange column, SP Sepharose™ Fast Flow (Amersham Biosciences), washing for four hours with 250 mM NaCl, 50 mM TrisHCl, pH 7.0, and finally eluting the activated protein with 750 mM NaCl, 50 mM TrisHCl, pH 7.0. After elution the activated mutants are referred to as GrB-H6 C228S, GrB-H6 C228A, GrB-H6 C228T, GrB-H6 C228V, and GrB-H6 C228F. Expression levels of the pro-IEPD-GrB-H6 C228X mutants (SEQ ID NOs: 4, 5, 6, 7 and 8) were similar to the pro-IEPD-GrB-H6 expression level. However, refolding efficiency differed by op to 90% relative to that of pro-IEPD-GrB-H6 (SEQ ID NO: 2). One mutant, pro-IEPD-GrB-H6 C228S (SEQ ID NO: 4), had a very low refolding efficiency and was therefore not analyzed further. This is contrary to what would be expected as the obvious conservative choice for substitution of a Cysteine residue would be Serine, since Serine most closely resembles Cysteine of all the amino acids naturally occurring in proteins, both in size, hydrophilicity and chemically.

The refolding efficiency of three of the other mutants, pro-IEPD-GrB-H6 C228A (SEQ ID NO: 5), pro-IEPD-GrB-H6 C228T (SEQ ID NO: 6), and pro-IEPD-GrB-H6 C228V (SEQ ID NO: 7) was similar to that of pro-IEPD-GrB-H6 (SEQ ID NO: 8).

A highly interesting finding was that higher protein recovery after refolding and purification was obtained for the pro-IEPD-GrB-H6 C228F mutant (SEQ ID NO: 8), wherein Cysteine had been replaced with Phenylalanine, than was the case for non-mutated pro-IEPD-GrB-H6 (SEQ ID NO: 2) comprising the Cys228 amino acid residue. Thus, when 70 mg, estimated by Bradford assay (Coomassie® Plus Protein Assay Reagent Kit, Pierce Biotechnology) using bovine serum albumin as protein standard, of either the pro-IEPD-GrB-H6 C228F (SEQ ID NO: 8) or the non-mutated pro-IEPD-GrB-H6 (SEQ ID NO: 2) was applied to the above described refolding and purification procedure, the final yield (protein recovery) was found to be 1.5% and 0.5%, respectively. This clearly shows that the mutated pro-IEPD-GrB-H6 C228F (SEQ ID NO: 8) provides for improved final protein recovery yields. The reasoning for the lower recovery yield may be that when the non-mutated pro-IEPD-GrB-H6 protein (SEQ ID NO: 2) was applied for purification and activation by cation exchange chromatography the protein apparently tended to precipitate and thus reduced the final yield (recovery) of active enzyme. No significant precipitation was observed for pro-IEPD-GrB-H6 C228F (SEQ ID NO: 8). Therefore, substitution of Cysteine 228 with Phenylalanine appears to be favourable for Granzyme B, in particular for self-activating Granzyme B. This is highly surprising, as the amino acid Phenylalanine is chemically very dissimilar to Cysteine and would not normally be the choice for a Cysteine substitution.

In the following examples we therefore focused on the C228F mutant, pro-IEPD-GrB-H6 C228F (SEQ ID NO: 8), along with pro-IEGR-GrB-H6 for comparison.

Example 3

Activation of Pro-IEGR-GrB-H6 Fusion Protein Using Purified Bovine Factor $X_a$ and Self-Activation of Pro-IEPD-GrB-H6 and Pro-IEAD-GrB-H6

Activation of Pro-IEGR-GrB-H6 by Factor Xa

A sample of monomeric inactive pro-IEGR-GrB-H6 produced as described in Example 2, was taken directly from the eluate from the SP Sepharose ion exchange. One mg of pro-IEGR-GrB-H6 (in app. 10 ml) was activated by the addition of 50 μg $FX_a$ (50 μl of 1 mg/ml) and incubated at room temperature for several days. The degree of cleavage/activation of pro-IEGR-GrB-H6 by $FX_a$, resulting in GrB-H6, was estimated by SDS PAGE.

Figure 1:
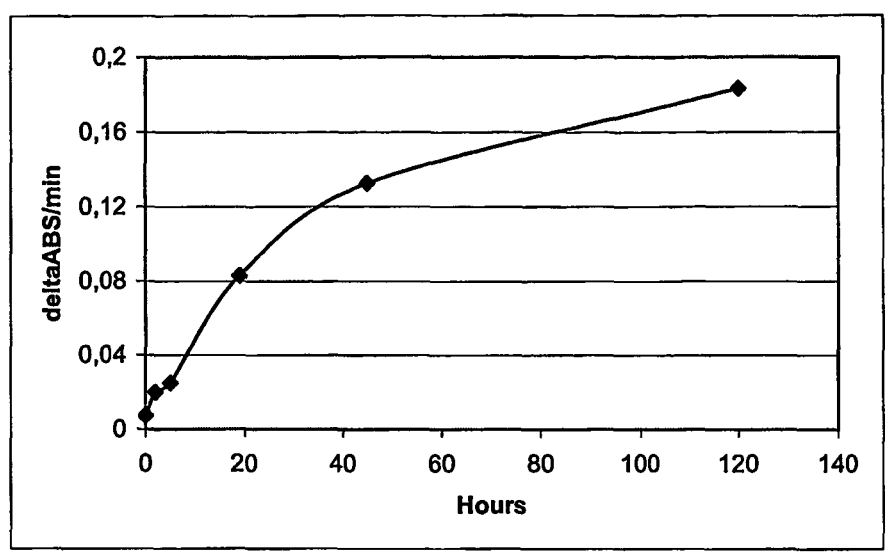
FIG. 1 shows the activity of an incubation of GrB-H6 with $FX_a$ followed for several days using the following colorimetric assay: 500 µl buffer (100 mM NaCl, 50 mM Tris-HCl pH 8.0), 4 µl 100 mM Ac-IEPD-pNA and 5 µl GrB-H6. A mixture of 100 µl GrB-H6 (approximately 10 µg) with 1 µl $FX_a$ (1 mg/ml) was kept at 4° C. during the incubation, and the activity was measured after 0 hours, 2 hours, 5 hours, 19 hours, 2 days and 5 days.

In addition, the Granzyme B activity during an incubation of pro-IEGR-GrB-H6 with $FX_a$ was followed for several days using the following colorimetric assay: 500 μl buffer (100 mM NaCl, 50 mM Tris-HCl pH 8.0), 4 μl 100 mM Ac-IEPD-pNA, and 5 μl incubation mixture. The incubation mixture was prepared by mixing 100 μl pro-IEGR-GrB-H6 (approximately 10 μg) with 1 μl $FX_a$ (1 mg/ml) and kept at 4° C. during the incubation. The results are summarised in Table 3 and FIG. 1.

TABLE 3

| Time | Time (hours) | $\Delta OD_{405}$/min |
|---|---|---|
| 0 hours | 0 | 0.0073 |
| 2 hours | 2 | 0.0200 |
| 5 hours | 5 | 0.0250 |
| 19 hours | 19 | 0.0829 |
| 2 days | 45 | 0.1325 |
| 5 days | 120 | 0.1832 |

To remove the added $FX_a$ the incubation mixture was loaded onto a SP Sepharose™ Fast Flow (Amersham Biosciences) ion exchange column washed in 250 mM NaCl, 50 mM Tris-HCl pH 7.0. The $FX_a$ did not bind to the column material, while the resulting GrB-H6 was eluted from the column with 750 mM NaCl, 50 mM Tris-HCl pH 7.0.

Colorimetric Activity Measurements

To determine whether the added $FX_a$ had been properly removed from the incubation mixture, both the GrB-H6 and the $FX_a$ activity was measured before and after removal of the added $FX_a$ using a colorimetric assay with the substrates S2222 (N-Benzoyl-L-isoleucyl-L-glutamyl-glycyl-L-arginine-p-nitroaniline, Chromogenix, Italy, cat. no. S2222) and Ac-IEPD-pNA (N-acetyl-L-isoleucyl-L-glutamyl-L-prolyl-L-aspartyl-p-nitroaniline, Calbiochem, La Jolla, USA, cat. no. 368067), where the absorbance was measured at 405 nm for approximately 3 minutes, and the $\Delta OD_{405}$/min was calculated. $FX_a$ activity was measured using the following mix: 500 μl buffer, 25 μl 3 mM S2222, and 5 μl $FX_a$. GrB-H6 activity was measured using the following mix: 500 μl buffer, 2 μl 100 mM Ac-IEPD-pNA, and 5 μl GrB-H6.

The buffer used was either 100 mM NaCl, 50 mM Tris-HCl pH 8.0 or 100 mM HEPES pH 7.4. An example using the 100 mM NaCl, 50 mM Tris-HCl pH 8.0 buffer is shown below in Table 3, where the top fraction from the SP Sepharose eluate after $FX_a$ removal was used:

TABLE 4

| Before $FX_a$ removal ($\Delta OD_{405}$/min) | | After $FX_a$ removal ($\Delta OD_{405}$/min) | |
| --- | --- | --- | --- |
| GrB activity | $FX_a$ activity | GrB activity | $FX_a$ activity |
| 0.1401 | 0.0139 | 0.2213 | 0.0001 |

As can be seen from the above Table 4, the added $FX_a$ was completely removed from the activation mixture by ion exchange on SP Sepharose™ Fast Flow column. The same result was obtained with the buffer comprising 100 mM HEPES pH 7.4.

Self-Activation of Pro-IEPD-GrB-H6 and Pro-IEAD-GrB-H6

Recombinant self-activating human Granzyme B derivatives IEPD-GrB-H6 and IEAD-GrB-H6 were produced as described in Example 2 by using the expression vectors pT7-IEPD-GrB-H6 and pT7-IEAD-GrB-H6 described in Example 1. The IEAD-GrB-H6 and IEPD-GrB-H6 proteins were eluted from the SP Sepharose columns and stored at 4° C. for 2 days before the activity of the respective top fractions were determined by using a colorimetric assay. For this purpose the following was mixed: 500 µl buffer (100 mM HEPES pH 7.5), 2 µl 100 mM Ac-IEPD-pNA, and 5 µl protein solution. The change in absorption was then determined at 405 nm during 3 min. The activity was further determined after additional incubation for 1 and 2 days at 4° C. The results are summarised in Table 5.

TABLE 5

| Protein | | $\Delta OD_{405}$/min |
| --- | --- | --- |
| IEAD-GrB-H6 | 2 days | 0.1372 |
| IEPD-GrB-H6 | 2 days | 0.1284 |
| IEAD-GrB-H6 | 3 days | 0.1607 |
| IEPD-GrB-H6 | 3 days | 0.1375 |
| IEAD-GrB-H6 | 4 days | 0.1983 |
| IEPD-GrB-H6 | 4 days | 0.1351 |

As can be seen from the Table 5, the self-activating derivatives pro-IEPD-GrB-H6 (SEQ ID NO: 2) and pro-IEAD-GrB-H6 (SEQ ID NO: 3) were activated without addition of any previously activated Granzyme B and the self-activation was not completed until after a least three or four days at 4° C.

Example 4

Granzyme B Activity Determined on Small Chromogenic Peptide Substrate

The activity of the activated and purified GrB-H6 was measured in different buffers using the Ac-IEPD-pNA substrate: 500 µl buffer, 2 µl 100 mM Ac-IEPD-pNA, and 5 µl GrB-H6. The $\Delta OD_{405}$/min was calculated from the first 0.75 min unless otherwise noted.

TABLE 6

| Buffer | Approximate amount Of GrB-H6 added (µg) | Activity ($\Delta OD_{405}$/min) |
| --- | --- | --- |
| TN pH 8.1 | 1 | 0.2213 (1 min) |
| TN pH 7.0 | 1 | 0.2794 |
| TN pH 7.4 | 1 | 0.2930 |
|  |  | 0.2624 |
|  | 0.5 | 0.0835 |
|  |  | 0.1082 |
|  | 0.2 | 0.0245 (3 min) |
| TN pH 7.4 + 0.1% TWEEN20 | 0.5 | 0.0887 |
|  | 0.2 | 0.0303 (3 min) |
| TN pH 7.4 + 5 mM $Ca^{2+}$ | 0.5 | 0.1401 |
| TN pH 7.4 + 5 mM $Mg^{2+}$ | 0.5 | 0.1491 |
| 100 mM HEPES pH 7.5 | 0.5 | 0.2350 |
| 100 mM HEPES pH 7.5 + 5 mM $Ca^{2+}$ | 0.5 | 0.2425 |
| 100 mM HEPES pH 7.2 | 0.5 | 0.1970 |
| 100 mM HEPES pH 7.4 | 0.5 | 0.2273 |
|  |  | 0.2328 |
| 100 mM HEPES pH 7.4 + 50 mM KCl | 0.5 | 0.2167 |
| 100 mM HEPES pH 7.4 + 50 mM NaCl | 0.5 | 0.1993 |
|  |  | 0.1938 |
| 100 mM NaCl, 50 mM Tris-HCl pH 7.4 | 0.5 | 0.1682 |
| 50 mM NaCl, 25 mM Tris-HCl pH 7.4 | 0.5 | 0.1948 |
| 100 mM KCl, 50 mM Tris-HCl pH 7.4 | 0.5 | 0.1662 |

TN = 100 mM NaCl, 50 mM Tris-HCl

As can be seen from the above Table 6, 100 mM HEPES pH 7.4-7.5 was the best buffer for GrB-H6 activity of the buffers evaluated.

In a later pH scanning experiment performed with GrB-H6 C228F the optimum pH for activity towards the substrate Ac-IEPD-pNA was found to be in the range of pH 7.5-7.8 in 100 mM HEPES.

To estimate the steady state kinetic parameters $K_M$ and $k_{cat}$, the same colorimetric assay as described above was used with a total volume of 500 µl in the assay cuvette. The assay buffer was 100 mM HEPES pH 7.75, and both GrB-H6 and GrB-H6 C228F were used in a concentration of 20 nM in each measurement. To construct a Lineweaver-Burk plot the following substrate concentrations were used: 5, 40, 150, 300, and 600 µM. The obtained results are shown in Table 7 below:

TABLE 7

|  | GrB-H6 | GrB-H6 C228F |
| --- | --- | --- |
| $K_M$ (µM) | 66.9 | 27.0 |
| $k_{cat}$ ($s^{-1}$) | 5.03 | 4.85 |
| $k_{cat}/K_M$ ($10^4$ $s^{-1}M^{-1}$) | 7.5 | 18.0 |

The obtained values for $K_M$, $k_{cat}$ and $k_{cat}/K_m$ shown in the above Table 7 for GrB-H6 and GrB-H6 C228F are very similar to the values found for a recombinant rat GrB (Harris J. L. et al., 1998.)

Example 5

Estimation of the Specificity of GrB-H6 and GrB-H6 C228F and the Stability of GrB-H6 C228F The Specificity of GrB-H6 and GrB-H6 C228F The specificity of both the GrB-H6 and the GrB-H6 C228F protease was examined using the chromogenic substrates Ac-LEED-pNA, Ac-VEID-pNA, Ac-YVAD-pNA, and Ac-DEVD-pNA, in addition to the Ac-IEPD-pNA substrate applied in Example 4. The activity assay was again carried out in 500 µl 100 mM HEPES pH 7.75 with a substrate concentration of 400 µM. For each measurement 1 µg of protease was added to the assay cuvette. All measurements were done in triplicate, and the activities obtained were normalized by setting the activity measured on Ac-IEPD-pNA to 100%. The results are shown in FIG. 2. It can be seen that the GrB-H6 protease is at least as specific as the GrB-H6 C228F protease.

The Stability of GrB-H6 C228F

In order to determine the stability of the GrB-H6 C228F protease, samples of GrB-H6 C228F was incubated in 100 mM HEPES pH 7.4 for 15 days at 4° C., 23° C. and 37° C. The 100 mM HEPES buffer was chosen in order to examine any auto-cleavage and degradation, but no significant "cannibalism" was observed as assessed by SDS PAGE (see FIG. 3A). The hydrolytic activity towards the chromogenic substrate Ac-IEPD-pNA was also measured during this incubation period, see FIG. 3B.

The GrB-H6 C228F protease is remarkably stable at 4° C. and 23° C. The activity only falls slightly with approximately 10% at 23° C. during the 15 days, and almost no degradation fragments are visible in the gel. Even at 37° C. there is still about 20% activity left after 15 days, and only very few degradation fragments show up in the gel.

It has also been found that the GrB-H6 C228F protease on a short time scale of 10 minutes is stable up to 50° C. (not shown here). In this experiment a sample of the protease was incubated for 10 minutes at a given temperature and then returned to room temperature by 10 minutes incubation at 23° C. The activity towards Ac-IEPD-pNA was then measured at 23° C. Up to the incubation temperature of 50° C. the protease can revert back to almost 100% activity after incubation at to room temperature (23° C.), but after exposure to a temperature above 50° C. the protease can no longer revert to an active form, and only very little activity can be detected.

Example 6

Design and Construction of Expression Vectors for Fusions Proteins Containing a Recognition Sequence Cleavable by GrB-H6 and GrB-H6 C228F In order to prepare suitable fusion proteins as substrates for GrB-H6 and GrB-H6 C228F, the FX$_a$ recognition sequence in the FX$_a$ cleavable fusion proteins H6-FX-TripBUB, H6-IEGR-RAP, H6Ubi-IEGR-ApoA1, and H6-FX-TN123 (encoded by pT7H6-FX-TripBUB, pT7H6-FX-RAP, pT7H6Ubi-FX-ApoA1, and pT7H6-FX-TN123, respectively) was changed from either IEGR (SEQ ID NO: 89) or IQGR (SEQ ID NO: 90) to IEPD (SEQ ID NO: 63), giving the constructs H6-TripUB IEPD↓SP (SEQ ID NO. 22), H6-IEPD-RAP (SEQ ID NO. 23), H6Ubi-IEPD-ApoA1 (SEQ ID NO. 24), and H6-IEPD-TN123 (SEQ ID NO. 25).

In the construct H6-TripUB IEPD↓SP (SEQ ID NO: 22) the Granzyme B recognition sequence is IEPD↓SP, where ↓ indicates the cleavage site. This recognition sequence is located between the H6 and the TripUB moiety of the construct, where the two residues, SP, C-terminal to the scissile bond are the N-terminal part of the TripUB moiety.

The recognition sequence in the following H6-TripUB fusion proteins (termed the H6-TripUB variants) is indicated as the last part of their name, as XXXX↓YY, wherein XXXX is the part of the Granzyme B recognition sequence between the hexa-His moiety H6 and the TripUB moiety, and wherein the YY residues are a part of the TripUB moiety.

The IEPD↓SP (SEQ ID NO: 85) cleavage site in the H6-TripUB IEPD↓SP (SEQ ID NO: 22) construct was changed to eight other cleavage sites to give the following variants: H6-TripUB IQAD↓SP (SEQ ID NO. 26), H6-TripUB IQAD↓SG (SEQ ID NO. 27), H6-TripUB VGPD↓SP (SEQ ID NO. 28), H6-TripUB VGPD↓FG (SEQ ID NO. 29), H6-TripUB IEPD↓TQ (SEQ ID NO. 30), H6-TripUB IEPD↓IV (SEQ ID NO. 31), H6-TripUB IEPD↓EP (SEQ ID NO. 32), and H6-TripUB IEPD↓EG (SEQ ID NO. 33), where ↓ indicates the cleavage site. In six of these eight constructs the P$_1$' and P$_2$'-sites (both part of the TripUB moiety) of the fusion protein were changed, namely in H6-TripUB IQAD↓SG (SEQ ID NO: 27), H6-TripUB VGPD↓FG (SEQ ID NO: 29), H6-TripUB IEPD↓TQ (SEQ ID NO: 30), H6-TripUB IEPD↓IV (SEQ ID NO: 31), H6-TripUB IEPD↓EP (SEQ ID NO: 32), and H6-TripUB IEPD↓ EG (SEQ ID NO: 33).

Construction of Fusion Protein Expression Vectors

The expression vector pT7H6-TripUB IEPD↓SP was constructed by using the QuikChange™ Site-Directed Mutagenesis Kit (STRATAGENE, Catalog #200518) according to the manufacturers' protocol with the vector pT7H6-FX-TripBUB (International Patent Application WO 9856906) as template and the oligonucleotide primers: TripUB GrB fw (SEQ ID NO: 34) and TripUB GrB rev (SEQ ID NO: 35).

The expression vector pT7H6-IEPD-RAP was constructed by site-directed mutagenesis as described above with the vector pT7H6-FX-RAP (Nykjr et al., 1992) as template and the oligonucleotide primers: RAP GrB fw (SEQ ID NO: 36) and RAP GrB rev (SEQ ID NO: 37).

The expression vector pT7H6Ubi-IEPD-ApoA1 was constructed by site-directed mutagenesis as described above with the vector pT7H6Ubi-FX-ApoA1 (International Patent Application WO0238609) as template and the oligonucleotide primers: Mut-GrB fw (SEQ ID NO: 38) and Mut-GrB rw (SEQ ID NO: 39).

The expression vector pT7H6-IEPD-TN123 was constructed by site-directed mutagenesis as described above with the vector pT7H6-FX-TN123 (Holtet et al., 1997) as template and the oligonucleotide primers: TN GrB fw (SEQ ID NO: 40) and TN GrB rev (SEQ ID NO: 41).

The expression vector pT7H6-TripUB IQAD↓SP was constructed by using site-directed mutagenesis as described above with the vector pT7H6-FX-TripBUB (WO 9856906) as template and the oligonucleotide primers: PC7-TripUB GR-AD fw (SEQ ID NO: 42) and PC7-TripUB GR-AD rev (SEQ ID NO: 43).

The expression vector pT7H6-TripUB IQAD↓SG was constructed by using site-directed mutagenesis as described above with the vector pT7H6-TripUB IQAD↓SP as template and the oligonucleotide primers: PC7-TripUB P-G fw (SEQ ID NO: 44) and PC7-TripUB P-G rev (SEQ ID NO: 45).

The expression vector pT7H6-TripUB VGPD↓SP was constructed by using site-directed mutagenesis as described above with the vector pT7H6-TripUB IEPD↓SP as template and the oligonucleotide primers: DNATrip IE-VG fw (SEQ ID NO: 46) and DNATrip IE-VG rev (SEQ ID NO: 47).

The expression vector pT7H6-TripUB VGPD↓FG was constructed by using site-directed mutagenesis as described above with the vector pT7H6-TripUB VGPD↓SP as template and the oligonucleotide primers: DNATrip SP-FG fw (SEQ ID NO: 48) and DNATrip SP-FG rev (SEQ ID NO: 49).

The expression vector pT7H6-TripUB IEPD↓TQ was constructed by a PCR reaction with the vector pT7H6-TripUB IEPD↓SP as template and the oligonucleotide primers: Trip IEPD-TQ (SEQ ID NO: 50) and UB3 (SEQ ID NO: 52). The resulting PCR product was digested with BamHI and HindIII and ligated into a BamHI-HindIII cut pT7H6(GS)3 vector (Christensen J. H et al. 1991).

The expression vector pT7H6-TripUB IEPD↓IV was constructed by a PCR reaction with the vector pT7H6-TripUB IEPD↓SP as template and the oligonucleotide primers: Trip IEPD-IV (SEQ ID NO: 51) and UB3 (SEQ ID NO: 52). The resulting PCR product was digested with BamHI and HindIII and ligated into a BamHI-HindIII cut pT7H6(GS)3 vector (Christensen J. H et al. 1991).

The expression vector pT7H6-TripUB IEPD↓EP was constructed by using site-directed mutagenesis as described above with the vector pT7H6-TripUB IEPD↓SP as template and the oligonucleotide primers: TripUB EP fw (SEQ ID NO: 53) and TripUB EP rev (SEQ ID NO: 54).

The expression vector pT7H6-TripUB IEPD↓EG was constructed by using site-directed mutagenesis as described above with the vector pT7H6-TripUB IEPD↓EP as template and the oligonucleotide primers: TripUB EG fw (SEQ ID NO: 55) and TripUB EG rev (SEQ ID NO: 56).

TABLE 8

Oligonucleotide primers

| Primer | Nucleotide sequence | SEQ ID NO. |
|---|---|---|
| TripUB GrB fw | 5'-GTGGATCCATCGAGCCTGACTCTCCTGGTACCGAGCC-3' | 34 |
| TripUB GrB rev | 5'-GGTACCAGGAGAGTCAGGCTCGATGGATCCACTACCAC-3' | 35 |
| RAP GrB fw | 5'-CGGATCCATCGAGCCTGACTACTCGCGGGAGAAG-3' | 36 |
| RAP GrB rev | 5'-CCCGCGAGTAGTCAGGCTCGATGGATCCGTGATG-3' | 37 |
| Mut-GrB fw | 5'-CGTGGTGGATCCATCGAGCCGGACGGTGGAGATGAACCCCCC-3' | 38 |
| Mut-GrB rw | 5'-GGGGGGTTCATCTCCACCGTCCGGCTCGATGGATCCACCACG-3' | 39 |
| TN GrB fw | 5'-GGATCCATCGAGCCTGACGGCGAGCCACCAACC-3' | 40 |
| TN GrB rev | 5'-GGCTCGCCGTCAGGCTCGATGGATCCGTGATGG-3' | 41 |
| PC7TripUB GR-AD fw | 5'-GGATCCATCCAGGCAGACTCTCCTGGTACCGAG-3' | 42 |
| PC7TripUB GR-AD rev | 5'-GTACCAGGAGAGTCTGCCTGGATGGATCCACTAC-3' | 43 |
| PC7TripUB P-G fw | 5'-GGATCCATCCAGGCAGACTCTGGTGGTACCGAGCCAC-3' | 44 |
| PC7TripUB P-G rev | 5'-CTCGGTACCACCAGAGTCTGCCTGGATGGATCCACTAC-3' | 45 |
| DNATrip IE-VG fw | 5'-GTAGTGGATCAGTCGGGCCTGACTCTCCTGGTAC-3' | 46 |
| DNATrip IE-VG rev | 5'-GAGAGTCAGGCCCGACTGATCCACTACCACTACC-3' | 47 |
| DNATrip SP-FG fw | 5'-GGCCTGACTTTGGTGGTACCGAGCCACCAAC-3' | 48 |
| DNATrip SP-FG rev | 5'-GGCTCGGTACCACCAAAGTCAGGCCCGACTG-3' | 49 |
| Trip IEPD-TQ | 5'-GGGAAAGGATCCATCGAGCCTGACACCCAGAAGCCCAAGAAGATTGTAAATG-3' | 50 |
| Trip IEPD-IV | 5'-GGGAAAGGATCCATCGAGCCTGACATTGTAAATGCCAAGAAAGATGTTGTGAAC-3' | 51 |
| UB3 | 5'-CGCAAGCTTGCATGCTTAGGATCCACCACGAAGTCTCAA-3' | 52 |
| TripUB EP fw | 5'-CGAGCCTGACGAGCCTGGTACCGAGCCAC-3' | 53 |
| TripUB EP rev | 5'-CGGTACCAGGCTCGTCAGGCTCGATGGATC-3' | 54 |
| TripUB EG fw | 5'-CCTGACGAGGGTGGTACCGAGCCACCAAC-3' | 55 |
| TripUB EG rev | 5'-GCTCGGTACCACCCTCGTCAGGCTCGATG-3' | 56 |

Example 7

Expression, Purification and Refolding of Fusion Proteins Containing a Recognition Sequence Cleavable by GrB-H6 and GrB-H6 C228F Expression of the Fusion Proteins To prepare the chimeric fusion proteins H6-TripUB IEPD↓SP (SEQ ID NO: 22), H6-IEPD-RAP (SEQ ID NO: 23), H6-IEGR-RAP, H6Ubi-IEPD-ApoA1 (SEQ ID NO: 24), H6Ubi-IEGR-ApoA1, H6-IEPD-TN123 (SEQ ID NO: 25) and the H6-TripUB variants, the expression vectors pT7H6-TripUB IEPD↓SP, pT7H6-IEPD-RAP, pT7H6-FX-RAP, pT7H6Ubi-IEPD-ApoA1, pT7H6Ubi-IEGR-ApoA1, pT7H6-IEPD-TN123, pT7H6-TripUB IQAD↓SP, pT7H6-TripUB IQAD↓SG, pT7H6-TripUB VGPD↓SP, pT7H6-TripUB VGPD↓FG, pT7H6-TripUB IEPD↓TQ, pT7H6-TripUB IEPD↓IV, pT7H6-TripUB IEPD↓EP, and pT7H6-TripUB IEPD↓EG (the last eight termed H6-TripUB variants) were grown in a medium scale (3 liter; 2×TY medium, 5 mM $MgSO_4$ and 0.1 mg/ml ampicillin) in E. coli BL21 cells, as described by Studier F W et al. (1990). Exponentially growing cultures at 37° C. were at $OD_{600}$=0.8 infected with bacteriophage λCE6 at a multiplicity of approximately 5. Cultures were grown at 37° C. for another four hours and the cells harvested by centrifugation. Cells were re-suspended in 100 ml of 750 mM NaCl, 100 mM Tris-HCl pH 8, and 1 mM EDTA pH 8. Phenol (150 ml adjusted to pH 8 with Trisma base) was added to each, and the mixtures were sonicated to extract total protein. After clarification by centrifugation (25 minutes at 10.000 g) crude protein fractions were precipitated from the phenol phases by addition of 2.5 volumes of 96% ethanol and centrifugation. Protein pellets were dissolved in 75 ml 6 M guanidinium chloride, 50 mM Tris-HCl pH 8, and 100 mM dithiothreitol (DTT).

Purification of H6-TripUB IEPD↓SP (SEQ ID NO: 22), H6-IEPD-RAP (SEQ ID NO: 23), H6-IEGR-RAP, H6Ubi-IEPD-ApoA1 (SEQ ID NO: 24), H6Ubi-IEGR-ApoA1 and H6-TripUB Variants (SEQ ID NO: 25)

Following gel-filtration on Sephadex™ G-25 Fine (Amersham Biosciences) into 8 M Urea, 500 mM NaCl, 50 mM Tris-HCl pH 8, and 10 mM 2-mercaptoethanol, the crude protein preparations of the H6-IEPD-TripUB and H6-IEPD-RAP (SEQ ID NO: 23) fusion proteins were applied by batch adsorption onto $Ni^{2+}$ activated NTA-agarose ($Ni^{2+}$-NTA-agarose, Quiagen) columns (usually 50-75 ml column volume) for purification (Hochuli E et al., 1988). The column was washed with the following:
1. 2× column volume 8 M urea, 500 mM NaCl, 50 mM Tris-HCl pH 8, and 10 mM 2-mercaptoethanol
2. 1× column volume 8 M urea, 500 mM NaCl, 50 mM sodium-phosphate pH 6.3, and 10 mM 2-mercaptoethanol
3. 1× column volume 6 M guanidinium chloride, and 50 mM Tris-HCl pH 8, and 10 mM 2-mercaptoethanol
4. 2× column volume 500 mM NaCl, and 50 mM Tris-HCl pH 8

The purified fusion proteins were then eluted with 500 mM NaCl, 50 mM Tris-HCl pH 8, and 10 mM EDTA.

Purification and Refolding of H6-IEPD-TN123 Fusion Proteins

Following gel-filtration on Sephadex™ G-25 Fine (Amersham Biosciences) into 8 M Urea, 500 mM NaCl, 50 mM Tris-HCl pH 8, and 10 mM 2-mercaptoethanol, the crude protein preparations of the H6-IEPD-TN123 (SEQ ID NO: 25) fusion proteins were applied by batch adsorption to $Ni^{2+}$ activated NTA-agarose ($Ni^{2+}$-NTA-agarose, Quiagen) columns (usually 50-75 ml column volume) for purification and in vitro refolding. The column was washed with the following:
1. 2× column volume 8 M urea, 500 mM NaCl, 50 mM Tris-HCl pH 8, and 10 mM 2-mercaptoethanol
2. 1× column volume 8 M urea, 500 mM NaCl, 50 mM sodium-phosphate pH 6.3, and 10 mM 2-mercaptoethanol
3. 1× column volume 6 M guanidinium chloride, 50 mM Tris-HCl pH 8, and 10 mM 2-mercaptoethanol Each fusion protein was then subjected to the iterative refolding procedure as described for plasminogen kringle 4 by Thøgersen et al. (International Patent Application WO 9418227). After completion of the refolding procedure each refolded fusion protein was then eluted from the $Ni^{2+}$-NTA-agarose in 500 mM NaCl, 50 mM Tris-HCl pH 8, 10 mM EDTA.

Fractions of each refolded fusion protein was gel filtrated into 50 mM NaCl, 25 mM sodium acetate pH 5.0, and 1 mM $CaCl_2$, and was further purified by ion exchange chromatography on SP Sepharose™ Fast Flow (Amersham Biosciences, 1.6 (i.d.) by 20 centimeter column) using a salt gradient from 50 mM NaCl, 25 mM sodium acetate pH 5.0 and 1 mM $CaCl_2$ to 1 M NaCl, 25 mM sodium acetate pH 5.0, 1 mM $CaCl_2$.

The final purification of each correctly folded fusion protein product was then accomplished by gel-filtration into 25 mM NaCl, 10 mM Tris-HCl pH 8, and 1 mM $CaCl_2$ followed by ion exchange chromatography on Q Sepharose™ Fast Flow (Amersham Biosciences, 1.6 (i.d.) by 20 centimeter column) using a salt gradient from 25 mM NaCl, 10 mM Tris-HCl pH 8, and 1 mM $CaCl_2$ to 500 mM NaCl, 10 mM Tris-HCl pH 8, and 1 mM $CaCl_2$.

Example 8

Cleavage of Prepared Fusion Proteins by GrB-H6, GrB-H6 C228F and FXa

Cleavage of H6-TripUB IEPD↓SP by GrB-H6

The fusion protein H6-TripUB IEPD↓SP (SEQ ID NO: 22) (prepared as described in Example 7) eluted from the $Ni^{2+}$-NTA-agarose column was gel filtrated into 100 mM HEPES pH 7.5 and 200 μl samples of the top-fraction was incubated at room temperature with either 0, 1 or 10 μl of activated GrB-H6 (approximately 0, 0.2 and 2 μg GrB-H6).

Samples for SDS PAGE were taken after 12, 19, and 24 hours of incubation, and gels are shown in FIGS. 4 and 5.

Only the correctly cleaved product appear in lanes C-D in FIG. 4 and lanes C-G in FIG. 5, and the longer the incubation time, the more cleavage product appears in the lanes, both for the addition of 1 and 10 μl GrB-H6. The simple band pattern observed is explained in FIG. 6. From this it is clear that GrB-H6 cleaved H6-TripUB IEPD↓SP (SEQ ID NO: 22) specifically at a single site. Cleavage at the correct site after the IEPD sequence is confirmed in lane E in FIG. 4, where the construct H6-FX-TripUB, containing the $FX_a$ recognition site IQGR in place of the GrB recognition site IEPD (SEQ ID NO: 63), was cleaved by $FX_a$ giving a product of the same size as the GrB-H6 cleaved H6-TripUB IEPD↓SP (SEQ ID NO: 22).

The effect of temperature and addition of $Ni^{2+}$ and NTA on the cleavage of H6-TripUB IEPD↓SP by GrB-H6

With the H6-TripUB IEPD↓SP (SEQ ID NO: 22) fusion protein the following nine incubations (Table 9) were set up using 200 μl H6-TripUB IEPD↓SP (SEQ ID NO: 22) and 5 μl GrB-H6 (approximately 1 μg GrB-H6) for each incubation.

TABLE 9

| 1 | No addition | 23° C. |
|---|---|---|
| 2 | 4.2 mM $Ni^{2+}$ | |
| 3 | 4.2 mM $Ni^{2+}$ + 5 mM NTA | |
| 4 | No addition | 37° C. |
| 5 | 4.2 mM $Ni^{2+}$ | |
| 6 | 4.2 mM $Ni^{2+}$ + 5 mM NTA | |
| 7 | No addition | 42° C. |
| 8 | 4.2 mM $Ni^{2+}$ | |
| 9 | 4.2 mM $Ni^{2+}$ + 5 mM NTA | |

Samples for SDS PAGE were taken after 2, 7 and 22 hours of incubation, see FIGS. 7, 8 and 9.

It was contemplated that the $Ni^{2+}$ ions would bind the N-terminal hexa-His tail (H6) of the fusion protein and facilitate access to the cleavage site recognized by GrB-H6. In addition the $Ni^{2+}$ ions would also bind the C-terminal hexa-His tail of the GrB-H6 construct. The addition of NTA was made to shield the $Ni^{2+}$ ions in solution in a similar fashion as on the $Ni^{2+}$-NTA agarose beads, i.e. to simulate the conditions on the $Ni^{2+}$-NTA agarose column.

FIG. 7 shows the incubations at 23° C., FIG. 8 at 37° C. and FIG. 9 at 42° C. When no $Ni^{2+}$ or NTA was added, the H6-TripUB IEPD↓SP fusion protein was cleaved similar to what is seen in FIGS. 4 and 5, though after 22 hours it seems that incubation at 37° C. is the most optimal of the three temperatures tested.

With the addition of 4.2 mM $Ni^{2+}$ some protein precipitated at the higher temperatures of 37° C. and 42° C., but no precipitation was seen at 23° C. Because of this no further cleavage of the fusion protein is seen in the gel after 2 hours incubation at these two temperatures, where it seems that both some H6-TripUB IEPD↓SP (SEQ ID NO: 22) and GrB-H6 precipitated. At 23° C. more fusion protein was cleaved after 22 hours than with no addition of $Ni^{2+}$.

The observed precipitation problem was eliminated by the addition of 5 mM NTA to the incubations. After 22 hours of incubation at 23° C. more fusion protein had been cleaved than with no $Ni^{2+}$ or NTA addition, so the addition of $Ni^{2+}$ and NTA seems to speed up the cleavage reaction. By further increasing the temperature to 37° C. and 42° C. an even greater increase in the rate of cleavage is seen. After 22 hours of incubation at 37° C. almost all the fusion protein was cleaved to the correct product. A little less was cleaved at 42° C. after 22 hours.

Comparing the rate of cleavage initially estimated in the experiments shown in FIGS. 4 and 5, to the rate of cleavage observed here, it is clear that the addition of $Ni^{2+}$ and NTA as well as the incubation at 37° C. dramatically speeds up the specific cleavage of H6-TripUB IEPD↓SP (SEQ ID NO: 22) by GrB-H6.

Cleavage of H6-IEPD-RAP by GrB-H6

The fusion protein H6-IEPD-RAP (SEQ ID NO: 23) (prepared as described in Example 7) eluted from the $Ni^{2+}$-NTA-agarose column was gel filtrated into 100 mM HEPES pH 7.4 and 200 µl samples of the top-fraction was incubated at room temperature with either 0, 1 or 10 µl of activated GrB-H6 (approximately 0, 0.2 and 2 µg GrB-H6). Samples for SDS PAGE were taken after 5, 23 and 26 hours of incubation, see FIG. 10.

After only 5 hours incubation with either 1 or 10 µl GrB-H6 as described above all the H6-IEPD-RAP (SEQ ID NO: 23) was cleaved to give the final product. It is also clear that there is at least one internal cleavage site in RAP, but this internal site was cleaved much slower than the IEPD sequence, though. That GrB-H6 cleaved off the H6 correctly at the IEPD sequence (SEQ ID NO: 63) can be seen by comparing the size of the product with purified samples of H6-FX-RAP cleaved partly (lane H) or completely (lane I) by $FX_a$ to give the final RAP product. In these lanes the degradation products from any internal cleavage by $FX_a$ had been removed by purification.

Comparison of H6-IEPD-RAP Cleavage by GrB-H6 and H6-IEGR-RAP Cleavage by $FX_a$

The cleavage of H6-IEPD-RAP (SEQ ID NO: 23) by GrB-H6 was compared with the cleavage of H6-IEGR-RAP by $FX_a$. Both H6-IEPD-RAP (SEQ ID NO: 23) and H6-IEGR-RAP were in 100 mM HEPES pH 7.4 and the following incubations were set up at room temperature, 23° C., with the protease:fusion protein ratio 1:1000:

1. 400 µl (app. 500 µg) H6-IEGR-RAP+0.5 µl $FX_a$ (1 mg/ml) (app. 0.5 µg)
2. 400 µl (app. 400 µg) H6-GrB-RAP+2 µl GrB-H6 (app. 0.4 µg)

Samples were taken for SDS PAGE after 0, ½, 1, 3, 5, 7 and 27 hours of incubation, see FIG. 11.

It is clear that both fusion proteins were cleaved very rapidly by their respective protease. After only ½ hour almost all of the fusion protein had been cleaved to give the correct product for both incubations.

However, for the H6-IEGR-RAP+$FX_a$ incubation all of the fusion protein had been degraded to give a variety of smaller fragments after 27 hours, and there is no correctly cleaved product left.

In the H6-IEPD-RAP (SEQ ID NO: 23)+GrB-H6 incubation degradation fragments are also seen, but not as many as for the H6-IEGR-RAP+$FX_a$ incubation. There seems to be only one GrB-sensitive site in RAP out of 19 possible sites (19 Asp residues in the RAP product), while there are several $FX_a$ sensitive sites (26 possible sites, 26 Arg residues). This slows down the degradation of H6-IEPD-RAP (SEQ ID NO: 23) by GrB-H6, whereby quite a lot of correctly cleaved product (app. 25%) is still present after 27 hours of incubation.

In summary the correct cleavage of the RAP fusion protein by GrB-H6 is just as fast as by $FX_a$, but the degradation of the RAP fusion protein by GrB-H6 is much slower than the degradation by $FX_a$. In this example the GrB-H6 protease is therefore superior to $FX_a$, and it shows that GrB-H6 is a very specific protease.

Comparison of H6Ubi-IEPD-ApoA1 Cleavage by GrB-H6 C228F and H6Ubi-IEGR-ApoA1 Cleavage by $FX_a$ For the cleavage reactions of H6Ubi-IEPD-ApoA1 (SEQ ID NO: 24)+GrB-H6 C228F and H6Ubi-IEGR-ApoA1+$FX_a$, the protease:substrate ratio was again 1:1000, and they were carried out at 23° C. in 100 mM HEPES pH 7.75:

1. 250 µl (app. 400 µg) H6Ubi-IEPD-ApoA1+0.4 µg GrB-H6 C228F
2. 250 µl (app. 350 µg) H6Ubi-IEGR-ApoA1+0.35 µg $FX_a$ Samples were taken for SDS PAGE after 0, 1, 3, 6, 24 and 48 hours of incubation at 23° C., see FIG. 12.

The GrB substrate, H6Ubi-IEPD-ApoA1, is approximately 100% cleaved after only 6 hours incubation at 23° C., whereas only a small fraction of the $FX_a$ substrate, H6Ubi-IEGR-ApoA1, has been cleaved after 6 hours. It is also seen that $FX_a$ requires more than 48 hours to complete the cleavage of the $FX_a$ substrate.

In the above two examples both the GrB-H6 and the GrB-H6 C228F protease is, as mentioned, superior to $FX_a$, since it either cleaves much faster (in the case of H6Ubi-X-ApoA1) or more specific (in the case of H6-X-RAP) than the purified, bovine $FX_a$ (where X denotes the recognition sites IEPD (SEQ ID NO: 63) or IEGR (SEQ ID NO: 89)). With these two examples it is demonstrated that GrB-H6 and GrB-H6 C228F can both cleave off a short N-terminal tag like the hexa-His tail (the H6 in H6-IEPD-RAP (SEQ ID NO: 23)) and cleave between two protein domains which are very closely connected by a short linker sequence comprising the GrB cleavage site adjacent to the polypeptide of interest (here the ApoA1 in H6Ubi-IEPD-ApoA1, with the linker sequence GGSIEPD, wherein IEPD is the GrB recognition site). It was verified that GrB-H6 and GrB-H6 C228F produced the correctly cleaved products by N-terminal sequencing in both the above cases.

Cleavage of H6-IEPD-TN123 by GrB-H6

The fusion protein H6-IEPD-TN123 (SEQ ID NO: 25) (prepared as described in Example 7) eluted from the Q Sepharose was after final purification gel filtrated into 100 mM HEPES pH 7.5, and 200 µl samples of the top-fraction was incubated at room temperature with either 0, 1 or 10 µl of activated GrB-H6 (approximately 0, 0.2 and 2 µg GrB-H6) both with and without 5 mM $CaCl_2$ present. Samples for SDS PAGE from the incubations without $CaCl_2$ were taken after 12, 19 and 24 hours as well as 5 days of incubation. See FIGS. 4, 5 and 13. Samples for SDS PAGE from the incubations both with and without $CaCl_2$ were taken after approximately 20 and 48 hours of incubation, see FIG. 14.

Without Ca$^{2+}$:

The samples showed a distinct band pattern when H6-IEPD-TN123 (SEQ ID NO: 25) was cleaved by GrB-H6 with no Ca$^{2+}$ present, as seen in FIGS. 4, 5 and 13. The H6-IEPD-TN123 (SEQ ID NO: 25) was cleaved correctly at the IEPD sequence, but also just as rapidly at an internal site of the sequence AQPD. The band pattern is explained in FIG. 15. That H6-IEPD-TN123 (SEQ ID NO: 25) was cleaved at the correct IEPD↓ site can be seen from lane J in FIG. 4, where murine H6-FX-TN123 had been cleaved by FX$_a$ giving a product of the same size as the product from GrB-H6 cleavage of H6-IEPD-TN123 (SEQ ID NO: 25) with no internal cleavage, i.e. the lowest band of the four bands in the pattern.

When the samples were reduced as in lanes B-D and L-N in FIG. 13 a different band pattern appears. This pattern is also explained in FIG. 15 and supports the notion of the specific internal cleavage site AQPD.

With Ca$^{2+}$:

FIG. 11 shows incubations of H6-IEPD-TN123 (SEQ ID NO: 25) with GrB-H6, where 5 mM CaCl$_2$ were added to some of the incubations. Here only two bands appear when Ca$^{2+}$ is present (lanes E and G), while four bands appear when no Ca$^{2+}$ is present, as described for FIGS. 4, 5, 13 and 15. This shows that by adding Ca$^{2+}$ to the incubation the internal cleavage site AQPD (SEQ ID NO: 84) in Tetranectin (TN123) can be made inaccessible to GrB-H6. This is because the AQPD sequence (SEQ ID NO: 84) is located in a loop, where the Q and D residues participates in the binding of Ca$^{2+}$-ions in Tetranectin. Thereby only the correct cleavage at the specific IEPD site in the fusion protein occurs, and the internal cleavage site in TN123 is "turned off" by the addition of Ca$^{2+}$.

Cleavage of H6-TripUB Variants

Each of the fusion proteins eluted from the Ni$^{2+}$-NTA-agarose column were gel filtrated into 100 mM HEPES pH 7.4 and fractions of approximately the same concentration of the five different H6-TripUB variants were used. The five variants were H6-TripUB IEPD↓SP (SEQ ID NO: 22), H6-TripUB IQAD↓SP (SEQ ID NO: 26), H6-TripUB IQAD↓SG (SEQ ID NO: 27), H6-TripUB VGPD↓SP (SEQ ID NO: 28) and H6-TripUB VGPD↓FG (SEQ ID NO: 29). Of each fusion protein 200 μl was incubated at room temperature, 23° C., with 5 μl of activated GrB-H6 (approximately 1 μg GrB-H6). The protease:fusion protein ratio was thereby 1:500. Samples for SDS PAGE were taken after 2, 6, 24 and 48 hours of incubation and gels are shown in FIGS. 16 and 17.

In FIG. 16 are shown the samples of H6-TripUB IEPD↓SP (SEQ ID NO: 22), H6-TripUB IQAD↓SP (SEQ ID NO: 26) and H6-TripUB IQAD↓SG (SEQ ID NO: 27). After 48 hours incubation approximately ⅔ of the original amount of non-cleaved H6-TripUB IEPD↓SP (SEQ ID NO: 22) had been correctly cleaved. In comparison the cleavage of the sequence IQAD↓SP, though, was much slower than cleavage of the IEPD↓SP sequence (SEQ ID NO: 85) in H6-TripUB IEPD↓SP (SEQ ID NO: 22). No product is visible after 2 hours incubation and only a small amount had been cleaved after 48 hours incubation. From the H6-TripUB IQAD↓SG (SEQ ID NO: 27) samples it is evident that the cleavage was much faster than for both H6-TripUB IEPD↓SP (SEQ ID NO: 22) and H6-TripUB IQAD↓SP (SEQ ID NO: 26). Already after 2 hours incubation the majority of the fusion protein had been cleaved to give the correct product. The single mutation of Pro (P) to Gly (G) in the P2' site in the recognition sequence was enough for this dramatic change in the cleavage rate.

In FIG. 17 are shown the samples from the H6-TripUB VGPD↓SP (SEQ ID NO: 28) and H6-TripUB VGPD↓FG (SEQ ID NO: 29) incubations. The cleavage of the VGPD↓SP sequence was almost as fast as for H6-TripUB IEPD↓SP (SEQ ID NO: 22) in FIG. 16. A small amount of product had formed after 2 hours and approximately half the amount of fusion protein had been cleaved after 48 hours. A dramatic change in reaction rate occurred when the P1' and P2' sites were changed from SP to FG in H6-TripUB VGPD↓SP (SEQ ID NO: 28). After only 2 hours incubation all the fusion protein had been correctly cleaved.

FIG. 18 shows the samples of the cleavage of H6-TripUB IEPD↓TQ (SEQ ID NO: 30) and H6-TripUB IEPD↓IV (SEQ ID NO: 31) compared to H6-TripUB IEPD↓SP (SEQ ID NO: 22). The two constructs H6-TripUB IEPD↓TQ (SEQ ID NO: 30) and H6-TripUB IEPD↓IV (SEQ ID NO: 31) are deletion mutants of the Trip part of H6-TripUB IEPD↓SP (SEQ ID NO: 22), where the first 7 residues are deleted in H6-TripUB IEPD↓TQ (SEQ ID NO: 30) and the first 13 residues deleted in H6-TripUB IEPD↓IV (SEQ ID NO: 31). Here the protease:fusion protein ratio was also 1:500, and the reactions were performed at 23° C. Samples for SDS PAGE was taken after 4, 24, and 96 hours of incubation.

From the gel shown in FIG. 18 it is clear that the cleavage of both H6-TripUB IEPD↓TQ (SEQ ID NO: 30) and H6-TripUB IEPD↓IV (SEQ ID NO: 31) is much faster than for H6-TripUB IEPD↓SP (SEQ ID NO: 22). As is shown in the following FIG. 19 this may be because of the Pro in the P2' site of H6-TripUB IEPD↓SP (SEQ ID NO: 22).

FIG. 19, Panel A shows the cleavage of H6-TripUB IEPD↓SP (SEQ ID NO: 22) and H6-TripUB IEPD↓EP (SEQ ID NO: 32), while Panel B shows the cleavage of H6-TripUB IEPD↓EP (SEQ ID NO: 32) and H6-TripUB IEPD↓EG (SEQ ID NO: 33). Here the protease:fusion protein ratio is again 1:500 and the cleavage reaction mixes were incubated both at 23° C. and at 37° C. For the gel in Panel A samples for SDS PAGE were taken after 0, 4, 24 and 48 hours, and for the gel in Panel B after 0, 6, 24 and 50 hours.

From these gels it is clear that a Pro in the P2' site is disadvantageous for the rate of cleavage by GrB-H6 C228F. A surprise, though, is that the GrB-H6 C228F is able to cleave the substrate containing the IEPD↓EP site (SEQ ID NO: 87). It cleaves this site with the same low efficiency as the IEPD↓SP site (SEQ ID NO: 85), but an acidic residues like Glu (E) in the P$_1$' site is infamous for abolishing cleavage by most serine proteases, for example purified, bovine FX$_a$.

If we now consider the P$_1$'P$_2$' sites of IEPD↓SP (SEQ ID NO: 85), IQAD↓SP (SEQ ID NO: 91), IQAD↓SG (SEQ ID NO: 92), IEPD↓EP (SEQ ID NO: 87), and IEPD↓EG (SEQ ID NO: 86) it shows that the change in the P$_2$' site from Proline to Glycine enhances the cleavage dramatically. This preference for G in the P$_2$' position was also found by Harris J L et al., 1998 for wt rat GrB using peptide substrates displayed on phage particles. Again GrB-H6 C228F shows a surprisingly effective cleavage of at the IEPD↓EG site (SEQ ID NO: 86) in spite of the E in P$_1$', which is, as mentioned above, is well-known in the art for obstructing cleavage by most serine proteases. At a protease to substrate ratio of 1:500 it takes less than 5 hours for GrB-H6 C228F to complete the cleavage of H6-TripUbi IEPD↓EG. In this respect the GrB-H6 C228F is again superior to FX$_a$.

In addition to these observations it is also important to note that even after 48 hours incubation with GrB-H6 or GrB-H6 C228F no internal cleavage took place in any of the H6-TripUB variants, showing that GrB-H6 and GrB-H6 C228F cleaves very specifically at the engineered recognition sites, even though the TripUB sequence contains 7 other Asp (D) residues.

Example 9

Immobilization of Granzyme B

In order to be able to easily remove the Granzyme B enzyme from the cleavage mixture the GrB-H6 C228F variant was used for immobilization onto a gel matrix in six experiments as described in the following.

The immobilization was performed in 0.3 M $NaHCO_3$/NaOH, pH 8.6 using the divinyl sulfone activated matrix called Mini-Leak (Kem-En-Tec). Two levels of activation were used; 2-5 millimoles and 10-50 millimoles vinyl groups per liter sedimented beads, respectively, and for each level of activation three experiments with different protein concentration and with or without PEG 20000 present was performed. The six experiments are summarized in Table 10. For the immobilization GrB-H6 C228F in 0.3 M $NaHCO_3$/NaOH; pH 8.6 was used at a protein concentration of 4 mg/ml, as estimated from a Bradford assay using bovine serum albumin as protein standard. The enzymatic activity of the GrB-H6 C228F solution was measured as described example 4 using the buffers 0.3 M $NaHCO_3$/NaOH; pH 8.6 and 30% PEG 20000; 0.3 M $NaHCO_3$ as assay buffers. The immobilization was performed by mixing drained gel, protein solution, and buffers to provide the volumes and concentrations listed in Table 10 followed by mixing at room temperature for 48 hours.

TABLE 10

| Experiment | Activation level (mM) | Protein concentration (mg/ml) | % PEG 20000 | Efficiency (%) |
|---|---|---|---|---|
| A | 2-5 | 0.75 | 0 | 10 |
| B | 2-5 | 0.75 | 9 | 18 |
| C | 2-5 | 2 | 0 | 10 |
| D | 10-50 | 0.75 | 0 | 16 |
| E | 10-50 | 0.75 | 9 | 10 |
| F | 10-50 | 2 | 0 | 10 |

Excess active groups were blocked by addition of 600 µl 0.2 M ethanol amine, pH 9.0 after draining the gel by centrifugation and removal of the supernatant, followed by mixing at room temperature over night. Non-bound protein was removed by washing the gel three times with 1 M NaCl (centrifugation followed by removal of the supernatant) and finally the gel was washed with 250 mM NaCl; 50 mM Tris-HCl, pH 8.0. The enzymatic activity of the immobilized GrB-H6 C228F was estimated by weighing out drained gel matrix, mixing with 300 µl of a substrate solution containing 100 mM HEPES, pH 7.75; 400 µM Ac-IEPD-pNA (Calbiochem) and then measure $OD_{405\,nm}$ of the supernatant after a certain time of incubation to determine $\Delta OD_{405\,nm}$/min per ml of substrate solution per g of drained gel. The enzymatic activity of immobilized GrB-H6 C228F was used to determine the coupling efficiency as a percentage of the calculated enzymatic activity if all applied enzyme was coupled and active.

The coupling efficiency is also listed in Table 10, and there is no significant difference in coupling efficiency between the two activation levels and the efficiency is also within the same range for the two protein concentration, so the highest coupling level is obtained when using a high protein concentration in the immobilization mixture. It can not be deduced whether addition of PEG 20000 to the coupling mixture is favourable for the immobilization and it was not evaluated for the high protein concentration.

The stability of the immobilized GrB-H6 C228F against denaturation with urea and guanidinium chloride (GdmCl) was determined for the two immobilizations with high protein concentration (experiment C and F). The gel matrix from experiment C and F was each aliquoted into three small spin columns and incubated with either 8 M urea; 0.5 M NaCl; 50 mM Tris-HCl, pH 8.0 (Urea), with 6 M guanidinium chloride; 50 mM Tris-HCl, pH 8.0 (GdmCl), or with 100 mM HEPES, pH 7.75 (HEPES) for 30 minutes at room temperature before it was washed and equilibrated in 100 mM HEPES, pH 7.75. The enzymatic activity of the immobilized GrB-H6 C228F was then determined as described above.

The enzymatic activities obtained are shown below in Table 11. Denaturation with urea seems to be favourable for the immobilized GrB-H6 C228F as the enzymatic activity is increased after incubation compared to incubation with the non-denaturing HEPES buffer, whereas denaturation with guanidinium chloride seems to have an effect that slightly decreases the enzymatic activity.

TABLE 11

| Experiment | Buffer | Enzymatic activity[a] |
|---|---|---|
| C | Urea | 99 |
|   | GdmCl | 89 |
|   | HEPES | 91 |
| F | Urea | 104 |
|   | GdmCl | 78 |
|   | HEPES | 90 |

[a]$\Delta OD_{405}$/min per ml of substrate solution per g of drained gel

Functionality of the immobilized GrB-H6 C228F was demonstrated by cleavage of the fusion proteins H6-TripUB IQAD↓SP (SEQ ID NO: 26) and H6-TripUB IQAD↓SG (SEQ ID NO: 27) prepared as described in Example 6. Cleavage experiments were performed with 50 µl of each gel matrix from the six immobilization experiments. The gel matrix was re-suspended in 200 µl of a buffer containing 100 mM HEPES, pH 7.75, and was incubated with 100 µl protein solution of each of the two fusion proteins at room temperature over night with shaking. Samples of the supernatant were withdrawn and analyzed by non-reducing SDS-PAGE, see FIG. 20.

For all twelve cleavage experiments the fusion proteins are cleaved to give a single product corresponding to TripUbi moiety from which the H6 fusion partner has been cleaved off. As expected, slightly more fusion protein is cleaved by the gel matrix from experiment C and F that should have the highest coupling levels. The cleavage efficiency was not evaluated.

REFERENCES

Christensen J. H. et al. (1991), FEBS Letters, 281(1-2): 181-184.

Nykjær A. et al. (1992), Journal of Biological Chemistry, 267(21): 14543-14548.

Holtet T. L. et al. (1997), Protein Science, 6: 1511-1515

Studier F. W. et al. (1990), Methods in Enzymology, 185: 60-89

Hochuli E. et al. (1988), Biotechnology, 1321-1325

Harris et al. (1998), Journal of Biological Chemistry 273(42): 27364-27373.

Casciola-Rosen et al. (1999), Journal of Experimental Medicine 190(6): 815-825.

Thøgersen et al. (1994), International Patent Application WO 9418227

Sun J. et al. (2001), Journal of Biological Chemistry 276(18): 15177-15184.

The invention claimed is:

1. A method for the preparation of a polypeptide of interest in authentic form, said method comprising the steps of:
(i) providing a fusion protein comprising, from its N-terminal to its C-terminal, (a) a fusion partner, (b) a Granzyme B protease recognition site comprising a Granzyme B protease cleavage site that is cleavable by human Granzyme B protease, and wherein the recognition site comprises an amino acid sequence of the general formula

P4 P3 P2 P1 ↓ (SEQ ID NO: 59)

wherein
P4 is amino acid I or V,
P3 is amino acid E, Q or M,
P2 is X, where X denotes any amino acid,
P1 is amino acid D, and
↓ is said Granzyme B protease cleavage site, and (c) the polypeptide of interest, wherein said cleavage site is adjacent to the polypeptide of interest, and
(ii) cleaving the fusion protein with Granzyme B protease at said cleavage site to yield said polypeptide of interest in authentic form.

2. The method according to claim 1 wherein the N-terminus of the polypeptide of interest is adjacent to the cleavage site and the penultimate amino acid at the N-terminus of the polypeptide of interest is glycine.

3. The method according to claim 1, wherein the polypeptide of interest is selected from the group consisting of an enzyme, a polypeptide hormone, a single chain antibody variable region fragment, and apolipoprotein A.

4. The method according to claim 3, wherein the enzyme is Granzyme B.

5. The method according to claim 1, wherein the fusion partner is an affinity-tag.

6. The method according to claim 5, wherein the affinity-tag is selected from the group consisting of a polyhistidine-tag, a polyarginine-tag, a FLAG-tag, a Strep-tag, a c-myc-tag, a S-tag, a calmodulin-binding peptide, a cellulose-binding peptide, a chitin-binding domain, a glutathione S-transferase-tag, and a maltose binding protein.

7. The method according to claim 1, wherein the fusion protein is cleaved with a Granzyme B protease selected from the group consisting of human Granzyme B protease, mouse Granzyme B protease and rat Granzyme B protease.

8. The method according to claim 1, wherein the Granzyme B protease is in an immobilised form.

9. The method according to claim 8, wherein the Granzyme B protease is immobilised via the C-terminus.

10. The method according to claim 8, wherein the Granzyme B protease is immobilised via a lysine amino acid residue.

11. The method according to claim 6, wherein the affinity-tag is a polyhistidine-tag, and wherein the fusion protein is contacted with said Granzyme B protease in the presence of $Ni^{2+}$ ions and Nitrilotriacetic Acid (NTA).

12. The method according to claim 11, wherein the concentration of $Ni^{2+}$ is in the range of 1-20 mM, and the concentration of NTA is in the range of 1-20 mM.

13. A method of cleaving a fusion protein comprising contacting said fusion protein with the human Granzyme B protease variant wherein the Cystein residue no. 228 (chymotrypsinogen numbering) is mutated to Phenylalanine.

14. A method for the preparation of a polypeptide of interest in authentic form, said method comprising the steps of:
(i) providing a fusion protein comprising, from its N-terminal to its C-terminal, (a) a fusion partner, (b) a Granzyme B protease recognition site comprising a Granzyme B protease cleavage site that is cleavable by human Granzyme B, wherein the recognition site comprises an amino acid sequence selected from the group consisting of ICPD↓ (SEQ ID NO: 61), IEAD↓(SEQ ID NO: 62), IEPD↓(SEQ ID NO: 63), IETD↓(-SEQ ID NO: 64), IQAD↓(SEQ ID NO: 65), ISAD↓(SEQ ID NO: 66), ISSD↓(SEQ ID NO: 67), ITPD↓(SEQ ID NO: 68), VAPD↓(SEQ ID NO: 69), VATD↓(SEQ ID NO: 70), VCTD↓(SEQ ID NO: 71), VDPD↓(SEQ ID NO: 72), VDSD↓(SEQ ID NO: 73), VEKD↓(SEQ ID NO: 74), VEQD↓(SEQ ID NO: 75), VGPD↓(SEQ ID NO: 76), VEID↓(-SEQ ID NO: 77), VRPD↓(SEQ ID NO: 78), VTPD↓(SEQ ID NO: 79), LEED↓(SEQ ID NO: 80), LEID↓(SEQ ID NO: 81), LGND↓(SEQ ID NO: 82), LGPD↓(SEQ ID NO: 83), and AQPD↓(SEQ ID NO: 84), and wherein ↓ is said Granzyme B protease cleavage site, and the polypeptide of interest, wherein said cleavage site is adjacent to the polypeptide of interest, and
(ii) cleaving the fusion protein with Granzyme B protease at said cleavage site to yield said polypeptide of interest in authentic form.

15. The method according to claim 14, wherein the polypeptide of interest is selected from the group consisting of an enzyme, a polypeptide hormone, a single chain antibody variable region fragment, and apolipoprotein A.

16. The method according to claim 15, wherein the enzyme is Granzyme B.

17. The method according to claim 14, wherein the fusion partner is an affinity-tag.

18. The method according to claim 17, wherein the affinity-tag is selected from the group consisting of a polyhistidine-tag, a polyarginine-tag, a FLAG-tag, a Strep-tag, a c-myc-tag, a S-tag, a calmodulin-binding peptide, a cellulose-binding peptide, a chitin-binding domain, a glutathione S-transferase-tag, and a maltose binding protein.

19. The method according to claim 14, wherein the fusion protein is cleaved with a Granzyme B protease selected from the group consisting of human Granzyme B protease, mouse Granzyme B protease and rat Granzyme B protease.

20. The method according to claim 14, wherein the Granzyme B protease is in an immobilised form.

21. The method according to claim 20, wherein the Granzyme B protease is immobilised via the C-terminus.

22. The method according to claim 20, wherein the Granzyme B protease is immobilised via a lysine amino acid residue.

23. The method according to claim 17, wherein the affinity-tag is a polyhistidine-tag, and wherein the fusion protein is contacted with said Granzyme B protease in the presence of Ni2+ ions and Nitrilotriacetic Acid (NTA).

24. The method according to claim 23, wherein the concentration of Ni2+ is in the range of 1-20 mM, and the concentration of NTA is in the range of 1-20 mM.

* * * * *